US008703142B2

(12) United States Patent
Diamond et al.

(10) Patent No.: US 8,703,142 B2
(45) Date of Patent: *Apr. 22, 2014

(54) METHODS TO BYPASS CD4+ CELLS IN THE INDUCTION OF AN IMMUNE RESPONSE

(75) Inventors: David C. Diamond, West Hills, CA (US); Adrian Ion Bot, Valencia, CA (US)

(73) Assignee: Mannkind Corporation, Valencia, CA (US)

( * ) Notice: Subject to any disclaimer, the term of this patent is extended or adjusted under 35 U.S.C. 154(b) by 1390 days.

This patent is subject to a terminal disclaimer.

(21) Appl. No.: 11/323,520

(22) Filed: Dec. 29, 2005

(65) Prior Publication Data

US 2008/0124352 A1 May 29, 2008

Related U.S. Application Data

(60) Provisional application No. 60/640,821, filed on Dec. 29, 2004.

(51) Int. Cl.
*A61K 39/00* (2006.01)
*A61K 48/00* (2006.01)

(52) U.S. Cl.
USPC .................. 424/184.1; 424/204.1; 424/208.1; 424/278.1; 514/44 R

(58) Field of Classification Search
None
See application file for complete search history.

(56) References Cited

U.S. PATENT DOCUMENTS

| | | | |
|---|---|---|---|
| 4,708,871 A | 11/1987 | Geysen et al. |
| 6,656,471 B1 | 12/2003 | Sastry et al. |
| 6,709,844 B1 | 3/2004 | Levy et al. |
| 6,861,234 B1 | 3/2005 | Simard et al. |
| 6,977,074 B2 | 12/2005 | Kundig et al. |
| 6,994,851 B1 | 2/2006 | Kundig et al. |
| 7,232,682 B2 | 6/2007 | Simard et al. |
| 7,252,824 B2 | 8/2007 | Simard et al. |
| 2003/0138808 A1 | 7/2003 | Simard et al. |
| 2003/0180949 A1 | 9/2003 | Levy et al. |
| 2003/0215425 A1 | 11/2003 | Simard et al. |
| 2003/0220239 A1 | 11/2003 | Simard et al. |
| 2003/0228634 A1 | 12/2003 | Simard et al. |
| 2004/0180354 A1 | 9/2004 | Simard et al. |
| 2004/0203051 A1 | 10/2004 | Simard et al. |
| 2005/0069982 A1 | 3/2005 | Simard et al. |
| 2005/0079152 A1* | 4/2005 | Bot et al. ............... 424/85.1 |
| 2005/0118186 A1 | 6/2005 | Chiang et al. |
| 2005/0130920 A1 | 6/2005 | Simard et al. |
| 2005/0142144 A1 | 6/2005 | Simard et al. |
| 2005/0221440 A1 | 10/2005 | Simard et al. |
| 2005/0260234 A1 | 11/2005 | Simard et al. |
| 2005/0287068 A1 | 12/2005 | Bot et al. |
| 2006/0008468 A1 | 1/2006 | Chiang et al. |
| 2006/0057673 A1 | 3/2006 | Liu et al. |
| 2006/0063913 A1 | 3/2006 | Liu et al. |
| 2006/0094661 A1 | 5/2006 | Liu et al. |
| 2006/0153844 A1 | 7/2006 | Kundig et al. |
| 2006/0153858 A1 | 7/2006 | Kundig et al. |
| 2006/0159689 A1 | 7/2006 | Chiang et al. |
| 2006/0159694 A1 | 7/2006 | Chiang et al. |
| 2006/0165711 A1 | 7/2006 | Bot et al. |
| 2006/0269521 A1 | 11/2006 | Levy et al. |
| 2007/0003563 A1 | 1/2007 | Bot et al. |
| 2007/0004662 A1 | 1/2007 | Qiu et al. |
| 2007/0049533 A1 | 3/2007 | Liu et al. |
| 2007/0060518 A1 | 3/2007 | Liu et al. |
| 2007/0060524 A1 | 3/2007 | Liu et al. |
| 2007/0184062 A1 | 8/2007 | Simard et al. |
| 2007/0269464 A1 | 11/2007 | Simard |
| 2008/0014211 A1 | 1/2008 | Bot et al. |

FOREIGN PATENT DOCUMENTS

| | | |
|---|---|---|
| WO | WO 99/02183 | 1/1999 |
| WO | WO 0172123 A1 | 10/2001 |
| WO | WO 02062368 | 8/2002 |
| WO | WO 2004/18666 | 3/2004 |
| WO | WO 2004/22709 | 3/2004 |
| WO | WO 2004/112825 | 12/2004 |
| WO | WO 2004112825 A2 | 12/2004 |
| WO | WO 2005/002621 | 1/2005 |
| WO | WO 2005002621 | 1/2005 |

OTHER PUBLICATIONS

Mena et al (2001) Immunology and Cell Biology. vol. 79: 87-89.*
Kan-Mitchell et al (2004) Journal of Immunology. 172: 5249-5261.*
Krieg et al (1998) Trends in Microbiology. 6 (1): 23-27.*
Kan-Mitchell et al. The HIV-1 HLA-A2-SLYNTVATL is a help-independent CTL epitope. J Immunol. May 1, 2004;172(9):5249-61.*
Altmann, D.M. & Blyth, W.A. (1985) *J. Gen. Virol.* 66: 1297-1303.
Buckland, M.S. & Pinching, A.J. (2004) Intern. J¹ of STD & AIDS 15: 574-583.
Carmichael, A. et al. (1993) *J Exp Med.* Feb. 1;177(2): 249-56.
Garber, D. et al. (2004) *The Lancet Infectious Diseases* 4: 397-413.
Geysen et al. (1984) *Proc. Natl. Acad. Sci. USA* 81: 3998-4002.
Geysen et al. (1986) *Molecular Immunology* 23: 709-715.
Rammensee, H.-G., et al. "MHC Ligands and Peptide Motifs," Springer-Verlag, Germany, 1997 Landes Bioscience, Austin, Texas.
Kiepiela et al. (2004) *Nature*, vol. 432: 769-775.
Klein, M.R. et al. (1995) *J Exp Med.* 181(4): 1365-72.

(Continued)

*Primary Examiner* — Michelle S Horning
(74) *Attorney, Agent, or Firm* — Davis Wright Tremaine LLP; Sheila R. Gibson; Wenhua Yu

(57) ABSTRACT

Embodiments of the invention disclosed herein relate to methods and compositions for bypassing the involvement of CD4+ cells when generating antibody and MHC class I-restricted immune responses, controlling the nature and magnitude of the response, and promoting effective immunologic intervention in viral pathogenesis. More specifically, embodiments relate to immunogenic compositions for vaccination particularly therapeutic vaccination, against HIV and other microbial pathogens that impact functioning of the immune system, their nature, and the order, timing, and route of administration by which they are effectively used.

45 Claims, 4 Drawing Sheets

(56) References Cited

OTHER PUBLICATIONS

Koup et al. (1994) *Nature* 370(6489): 416.
Koup et al. (1994) *J Virol*. 68(7): 4650-5.
Koup, et al. (1994) *J Exp Med*. 180(3): 779-82.
Lohr, H.F., et al. (2002) *Clin. Exp. Immunol*. 130: 107-104.
Murakami, H., et al. (2004) *Clin. Exp. Immunol*. 137: 559-565.
Musey, L., et al. (1997) *New Eng J Medicine*. 337(18): 1267-1274.
Osorio, Y., et al. (2002) *Ocul. Immunol. Inflamm*. 10: 105-116.
Rinaldo, C., et al. (1995) *J. Viral*. 69(9): 5838-5842.
Roberts, J.P. (2004) *The Scientist* 18: 26-27.
Rowland-Jones, S. L., et al. (1993) *The Lancet* 341: 860-861.
Rowland-Jones, S., et al. (1995) *Nature Medicine* 1(1): 59-64.
Walker, B. D., et al. (1987) *Nature* 328: 345-348.
Wilson, C.C., et al. (2003) *J. Immunol*. 171: 5611-5623.
Xu, M. et al. (2004) *J. Immunol*. 173: 1232-1239.
Zheng, B.J., et al. (2004) *J. Viral Hepat*. 11: 217-224.
U.S. Appl. No. 09/560,465, filed Nov. 7, 2001. Title: Epitope Synchronization in Antigen Presenting Cells.
U.S. Appl. No. 09/561,571, filed Apr. 28, 2000, entitled Epitope Clusters.
U.S. Appl. No. 09/561,572, filed Apr. 28, 2000, entitled Expression Vectors Encoding Epitopes of Target-Associated Antigens.
U.S. Appl. No. 09/999,186, filed Nov. 7, 2001, entitled Methods of Commercializing an Antigen.
U.S. Appl. No. 09/988,320, filed Dec. 10, 1997. Title: Method of Inducing a CTL Response.
U.S. Appl. No. 60/363,131, filed Mar. 7, 2002. Title: HLA-Transgenic Murine Tumor Cell Line.
U.S. Appl. No. 60/337,017, filed Nov. 7, 2001. Title: Epitope Sequences.
U.S. Appl. No. 60/282,211, filed Apr. 6, 2001. Title: Epitope Sequences.
U.S. Appl. No. 11/772,811, filed Dec. 10, 1997. Title: Anti-neovasculature Preparations for Cancer.
U.S. Appl. No. 60/834,074, filed Jul. 28, 2006. Title: Broad-Range Tyrosinase CTL Epitope.
U.S. Appl. No. 11/418,497, filed May 3, 2006. Title: Method of Inducing a CTL Response.
U.S. Appl. No. 11/418,397, filed May 3, 2006. Title: Method of Inducing a CTL Response.
Berinstein, et al. "Induction of CD8+ T cell responses to melanoma with tumor-antigen expressing canary pox vectors," Retrieved from URL: http://www.sabin.org/PDF/wc2004.pdf.
Beust Von, et al., "Improving the therapeutic index of CpG oligodeoxynucleotides by intralymphatic administration," *European Journal of Immunology*. 35(6): 1869-1876, Jun. 2005.
Boehmer Von, et al., "The manipulation of immunity," *EMBO Reports, Nature Publishing Group*. 5(8): 766-771, Jul. 2004.
Gelman, et al., "Toll-like receptor ligands directly promote activated CD4+ T cell survival," *Journal of Immunology*. 172(10): 6065-6073, May 2004.
Giri, et al., "DNA vaccines against human immunodeficiency virus type 1 in the past decade," *Clinical Microbiology Reviews*. 17(2): 370-389, Apr. 2004.
Johansen, et al.,"Direct intralymphatic injection of peptide vaccines enhances immunogenicity," *European Journal of Immunology*. 35(2): 568-574, Feb. 2005.
Maloy, et al., "Intralymphatic immunization enhances DNA vaccination," *Proceedings of the National Academy of Sciences of the United States of America*. 98(6): 3299-3303, Mar. 2001.
Okuda, et al., "DNA vaccination followed by macromolecular multicomponent peptide vaccination against HIV-1 induces strong antigen-specific immunity," Vaccine, Butterworth Scientific. 15(10): 1049-1056, Jul. 1997.
Pulendran, et al., "Modulating vaccine responses with dendritic cells and Toll-like receptors," Immunological Reviews. 199: 227-250, Jun. 2004.
Schwarz, et al., "Role of toll-like receptors in costimulating cytotoxic T cell responses," *European Journal of Immunology*. 33(6): 1465-1470, Jun. 2003.
Tagawa, et al., "Phase I study of intranodal delivery of a plasmid DNA vaccine for patients with Stage IV melanoma," *Cancer*. 98(1): 144-154, Jul. 2003.
Woodberry, et al., "Prime boost vaccination strategies: CD8 T cell numbers, protection, and TH1 bias," *Journal of Immunology*. 170(5): 2599-2604, Mar. 2003.
International Search Report, PCT/US2005/047442, filed Dec. 30, 2005.

\* cited by examiner

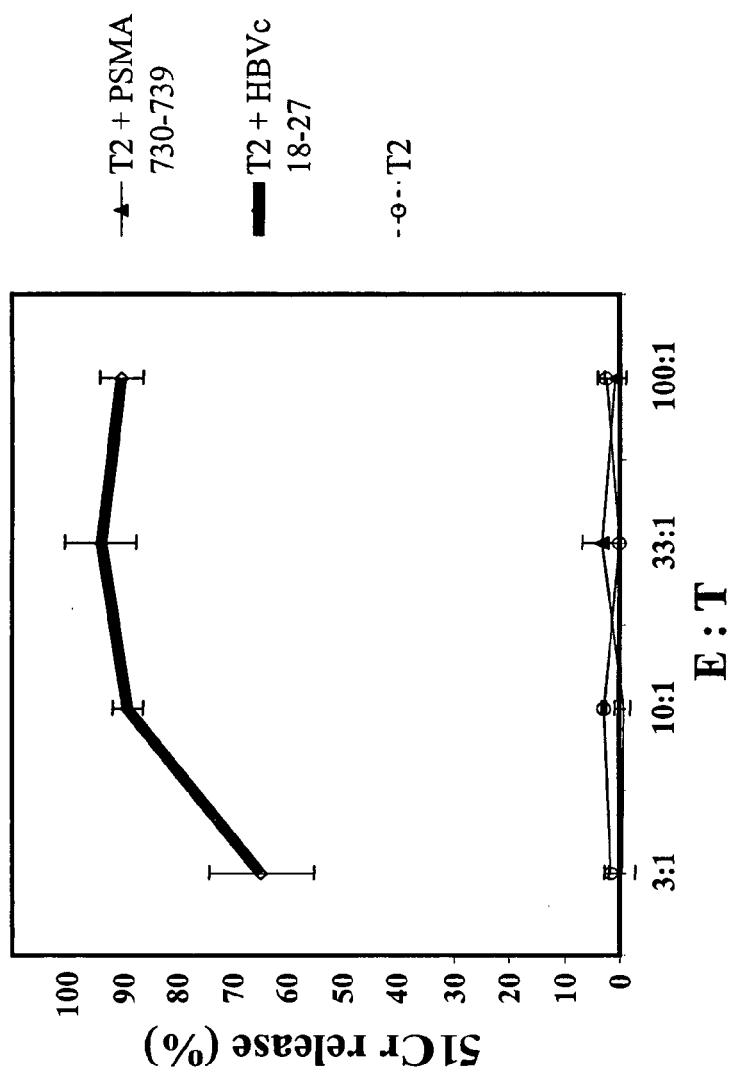
Fig. 1: Response to HBVc 18-27

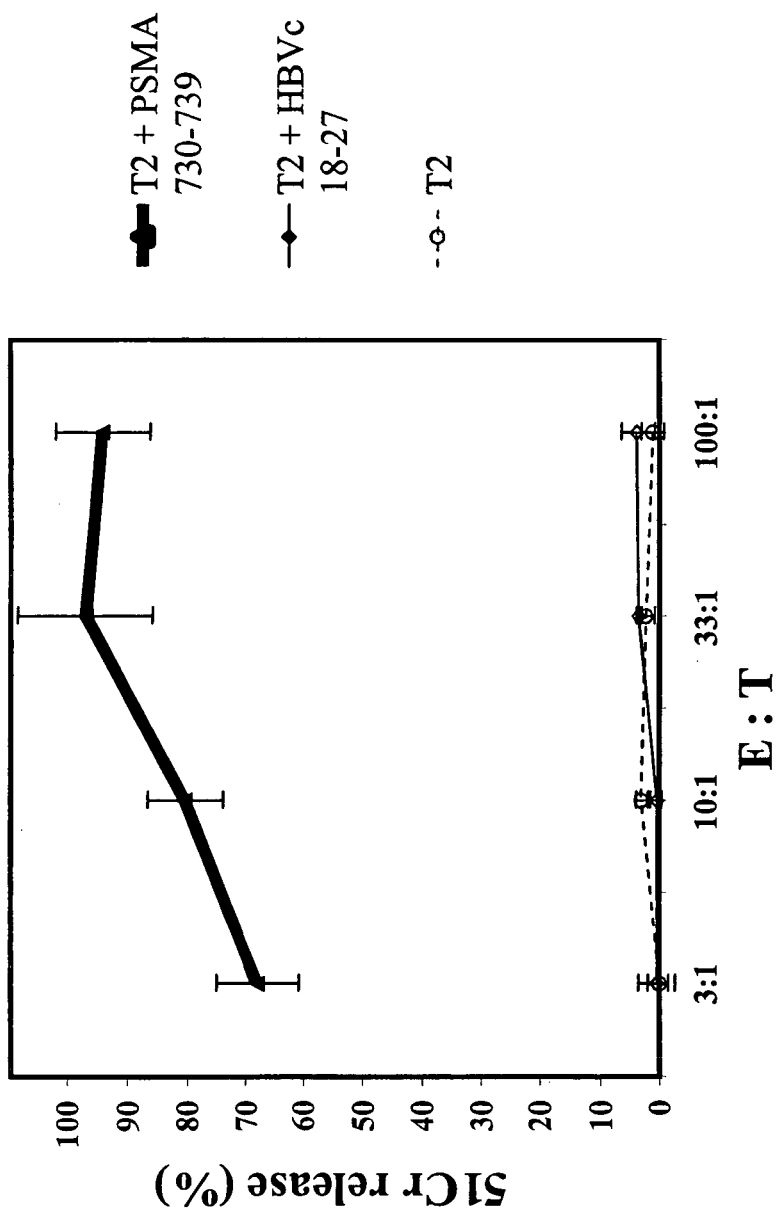
Fig. 2: Response to PSMA 730-739

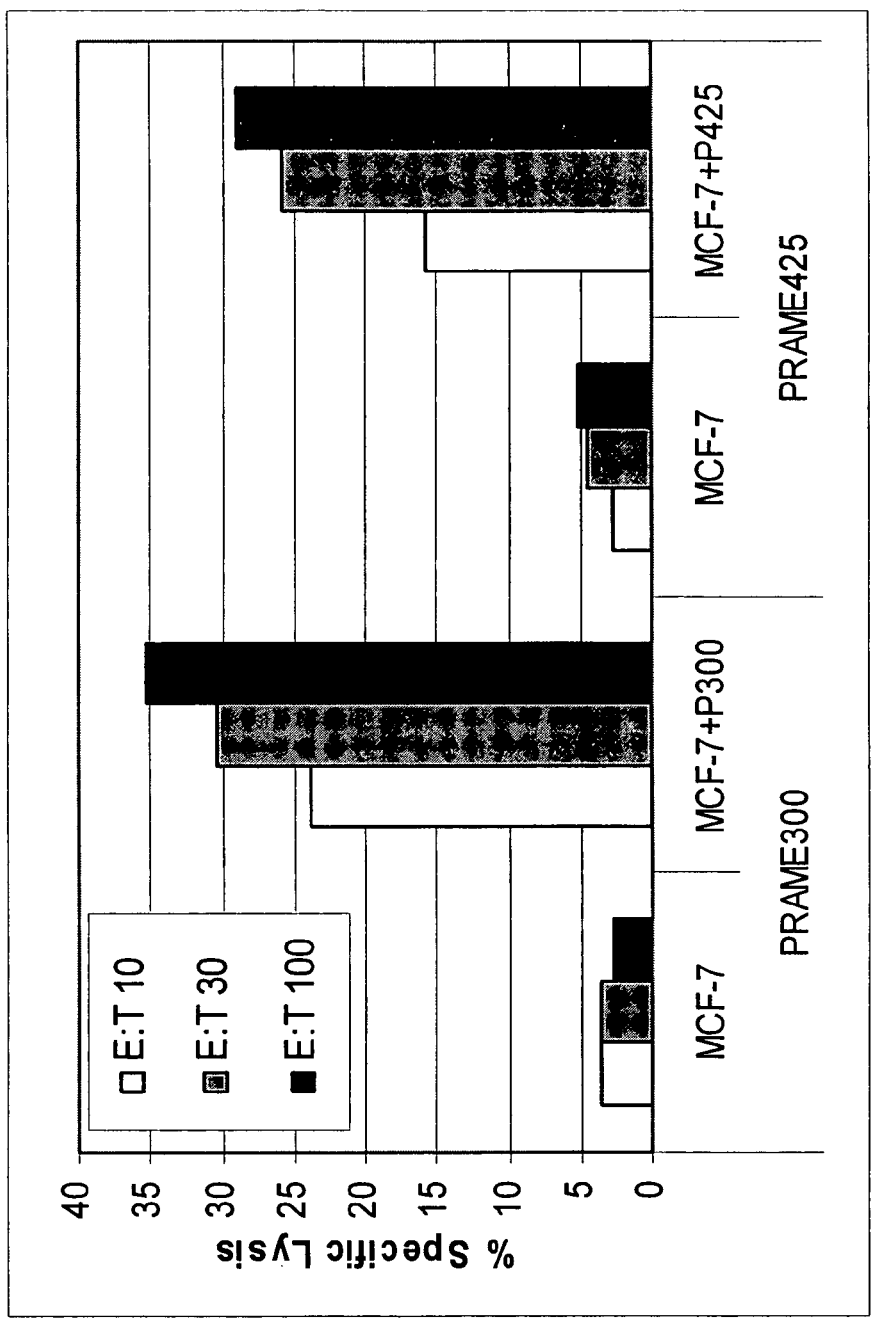
Fig. 3: Repsonse to PRAME 300-309 and 425-433

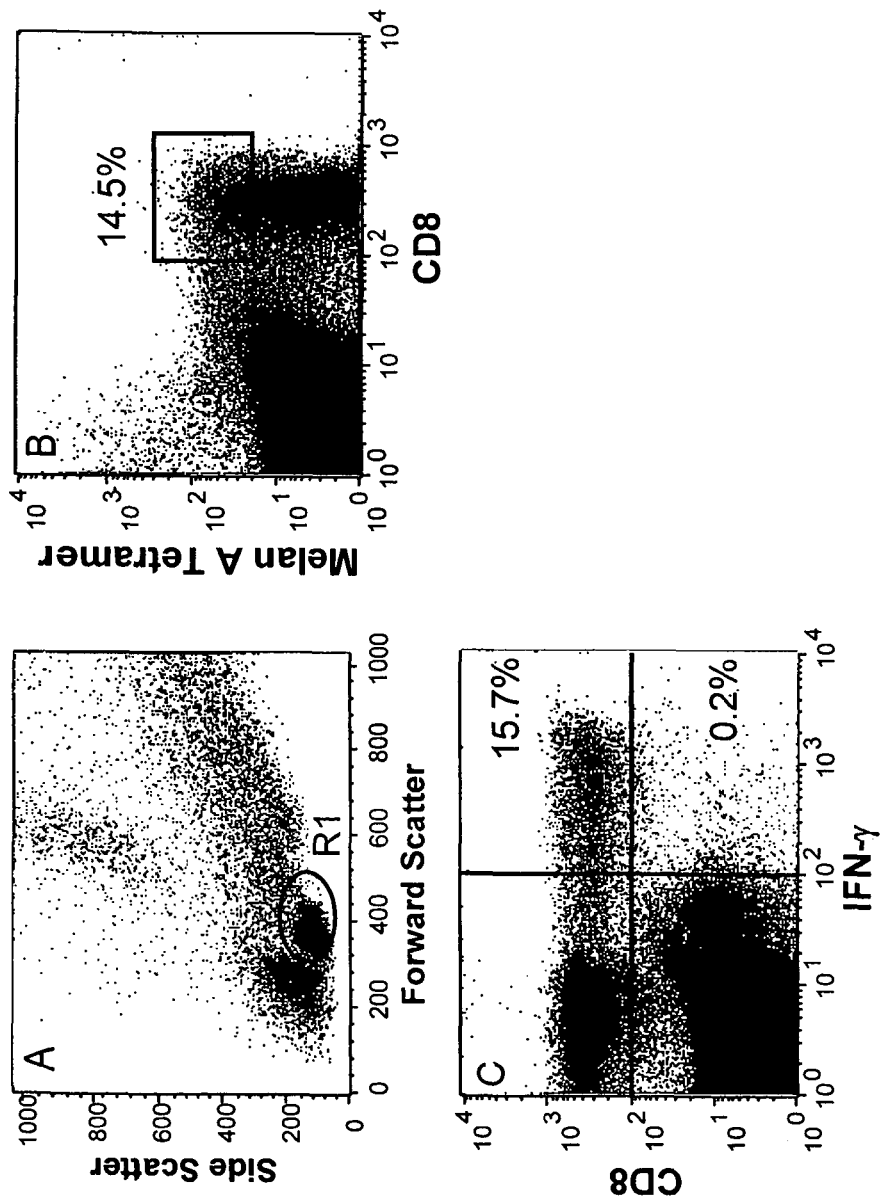
Figure 4: CTLs are specifically activated by antigen

METHODS TO BYPASS CD4+ CELLS IN THE INDUCTION OF AN IMMUNE RESPONSE

CROSS REFERENCE TO RELATED APPLICATIONS

This application claims priority under 35 U.S.C. §119(e) to U.S. Provisional Application No. 60/640,821, filed on Dec. 29, 2004, entitled METHODS TO BYPASS CD4+ CELLS IN THE INDUCTION OF AN IMMUNE RESPONSE; the disclosure of which is incorporated herein by reference in its entirety.

SEQUENCE LISTING

The present application includes a Sequence Listing provided in electronic format on duplicate copies of a CD-ROM marked "Copy 1" and "Copy 2." The duplicate copies of the CD-ROM each contain a file entitled MANNK.048A.txt created on Apr. 17, 2006 which is 76185.6 bytes in size. The information on these duplicate CD-ROMs is incorporated herein by reference in its entirety.

BACKGROUND OF THE INVENTION

1. Field of the Invention

Embodiments of the invention disclosed herein relate to methods and compositions for bypassing the involvement of $CD4^+$ cells when generating antibody and MHC class I-restricted immune responses, controlling the nature and magnitude of the response, and promoting effective immunologic intervention in viral pathogenesis. More specifically, embodiments relate to immunogenic compositions for vaccination particularly therapeutic vaccination, against HIV and other microbial pathogens that impact functioning of the immune system, their nature, and the order, timing, and route of administration by which they are effectively used.

2. Description of the Related Art

The Major Histocompatibility Complex and T Cell Target Recognition

T lymphocytes (T cells) are antigen-specific immune cells that function in response to specific antigen signals. B lymphocytes and the antibodies they produce are also antigen-specific entities. However, unlike B lymphocytes, T cells do not respond to antigens in a free or soluble form. For a T cell to respond to an antigen, it requires the antigen to be bound to a presenting molecule known as a major histocompatibility complex (MHC) antigen/protein/marker.

MHC proteins provide the means by which T cells distinguish healthy "self" cells from foreign or infected (non-self) cells. MHC molecules are a category of immune receptors that present potential peptide epitopes to be monitored subsequently by the T cells. There are two types of MHC, class I MHC and class II MHC. $CD4^+$ T cells interact with class II MHC proteins and predominately have a helper phenotype while $CD8^+$ T cells interact with class I MHC proteins and predominately have a cytolytic phenotype, but each of them can also exhibit regulatory, particularly suppressive, function. Both classes of MHC protein are transmembrane proteins with a majority of their structure on the external surface of the cell. Additionally, both classes of MHC have a peptide binding cleft on their external portions. It is in this cleft that small fragments of proteins, native or foreign, are bound and presented to the extracellular environment.

The antigen receptor of T cells, or T cell receptor (TCR), recognizes the complex formed by peptide and MHC marker by binding to it. The MHC is highly polymorphic with the result that the specificity exhibited by a TCR is dependent on both the peptide and the MHC marker in the recognized complex. This requirement is called MHC restriction. T cell immune responses are induced when T cells recognize peptide-MHC marker complexes displayed by cells called professional antigen presenting cells (pAPCs). Effector functions, such as cytolytic activity or cytokine secretion, are actuated when T cells subsequently recognize peptide-MHC marker complexes on other cells of the body.

HIV

Human Immunodeficiency Virus (HIV) is a member of the Lentivirus genus of the Retroviridae family. This family of viruses is known for latency, persistent viremia, infection of the nervous system, and weak host immune responses. HIV has high affinity for $CD4^+$ T lymphocytes and monocytes. HIV binds to $CD4^+$ T-cells at the cell surface and becomes internalized. The virus replicates by generating a DNA copy by reverse transcriptase. Viral DNA becomes incorporated into the host DNA, enabling further replication. HIV is the causative agent of acquired immune deficiency syndrome, AIDS.

Despite more than 20 years of HIV related research, infection with HIV remains a major public health concern. Globally, more than 42 million people are infected, including about 5 million newly infected in the year 2003 (Garber, D. et al., *The Lancet Infectious Diseases* 4:397-413, 2004). The most common clinical manifestations of HIV are due to progressive immunodeficiency caused by a selective loss of $CD4^+$ lymphocytes (Buckland, M. S. & Pinching, A. J. *Intern. J of STD & AISA* 15:574-583, 2004). Both $CD4^+$ and $CD8^+$ T-cells are important in the control of viral, including HIV, replication. Activated $CD4^+$ T-helper cells produce cytokines and interact with cell-surface receptors that prompt B cells to produce antibodies, and they interact indirectly (via antigen presenting cells) or directly with $CD8^+$ T lymphocytes to induce differentiation into cytotoxic cells. HIV grows far better in activated cells than in cells at rest (Roberts, J. P. *The Scientist* 18:26-27, 2004). Consequently, the very cells central in orchestrating the fight against viral pathogens, $CD4^+$ T-cells, may then be lost by apoptosis, cytolysis, or cell mediated cytotoxicity. The result is an ineffective immune response due to the prompt deletion of activated T cells, with expected repercussions on induction, expansion and differentiation of $CD8^+$ T cells and B cells recognizing viral antigens. Initially, the rate of production of $CD4^+$ T cells is greater than peripheral destruction, and so antibody production and generation of an expanded repertoire of $CD8^+$ T-cells to kill virally infected targets proceeds correctly. Over time, the rapid mutation rate of HIV, poor immunogenic characteristics of HIV proteins, and the scale of HIV replication overwhelm the host immune system. Since $CD4^+$ T cells are required to support the pool of HIV-specific $CD8^+$ T-cells, the loss of HIV-specific $CD4^+$ cells leads to a loss of HIV-specific $CD8^+$ T-cells. Immune containment of HIV infection fails and clinical progression to AIDS ensues.

Most infected patients do not exhibit overt clinical manifestations of the disease for six to ten years following initial infection. However a small group remain long-term non-progressors (LTNP), and remain free of disease for ten or more years. They exhibit lower viral loads and stable $CD4^+$ cell counts which have in part been attributed to cell-mediated immunity. The nature of viral suppression in this group has been the focus of much research. There has been a great deal of effort made to understand the characteristics of LTNP and the mechanism by which the disease-free state is achieved, so that better therapeutics and prophylactics may be designed.

Therapeutics

Morbidity and mortality associated with HIV infection have been dramatically reduced with the advent of antiretroviral therapy targeting two key enzymes: reverse transcriptase and protease. However, beneficial effects can be variable, prolonged treatment induces considerable toxicity, and effectiveness is undermined by the emergence of drug-resistant mutations. Also, the high cost of antiretroviral therapies limits access and availability in developing countries. Thus, alternative, less costly strategies capable of effecting sustained viral suppression are desperately needed.

Therapeutic immunization as a treatment for HIV infection may prove to be such an alternative. However, several critical aspects of HIV infection present novel challenges to the development of an effective vaccine. These properties include viral particles that are difficult to neutralize with antibodies; selective infection, destruction, and impaired regeneration of $CD4^+$ T-helper cells; rapid virus evolution providing escape from cellular and humoral immune responses; and high viral genetic diversity, distribution, and prevalence (Garber, D. et al., *The Lancet Infectious Diseases* 4:397-413, 2004). Also, it has been recently suggested that a vaccine-primed immune system might be more susceptible to infection. Boosting the HIV specific helper cells, an outcome of vaccination, may be giving the virus more targets to infect. Since more conventional vaccination strategies depend on co-induction of T helper (Th) cells, it is expected that their efficacy is low or the overall effect detrimental in a setting where Th cell function is impaired by HIV (Roberts, J. P. *The Scientist* 18:26-27, 2004).

The immune system may effectively eliminate virus-infected cells during the clinical course of HIV-1 infection using virus-specific major histocompatibility complex (MHC) class-I restricted CTL activity (Koup, et al. *J Exp Med.* 180 (3):779-82, 1994; Koup et al. "*Nature*, 370 (6489): 416, 1994; and Koup et al., *J. Virol.* 68 (7):4650-5, 1994). There is evidence that suggests HIV-1-specific CTL activity is important for controlling viral spread during the clinical course of HIV-1 infection (Klein, 1995; Koup, 1994), for maintaining low levels of viral load during the asymptomatic phase (Musey, 1997; Rinaldo, 1995; Koup, 1994; Walker, 1987), and possibly for complete elimination of virus-infected cells, as implied from the observation of HIV-exposed, but virus-negative, children and women (Rowland-Jones, 1995; Rowland-Jones, 1993). Furthermore, observations from cross-sectional studies have shown the absence, or severely decreased levels, of HIV-1-specific CTL responses during advanced stages of HIV-1 infection (Carmichael, 1993). Taken together, recent vaccine strategy has focused on eliciting antiviral $CD8^+$ T cell responses to control the level of HIV replication in vivo (Garber, D. et al., *The Lancet Infectious Diseases* 4:397-413, 2004). Rationale for potential efficacy of $CD8^+$ T-cell-based AIDS vaccine is that reduction of the level of setpoint viral load may slow the rate of progression to AIDS and eliminate active reservoirs of infection.

Other Pathogens

HIV is not the only pathogen for which activation or expansion of $CD4^+$ cells is associated with pathological processes. For example corneal scarring incident to herpes simplex virus (HSV) infection is attributable to the action of $CD4^+$ T cells and the cytokines they produce. (Osorio, Y. et al., *Ocul. Immunol. Inflamm.* 10: 105-116, 2002; Altmann, D. M. & Blyth, W. A. *J. Gen. Virol.* 66:1297-1303, 1985; Xu, M. et al., *J. Immunol.* 173:1232-1239, 2004). HIV is also not the only pathogen for which impairment of the $CD4^+$ T cell response results in failure to mount a more effective immune response, persistence of infection, and greater morbidity or mortality. Failure of dendritic cells (DC) to increase class II MHC expression, and thus productively interact with $CD4^+$ T cells, contributes to the persistence of Hepatitis B virus (HBV) infection (Zheng, B. J., et al., *J. Viral Hepat.* 11:217-224, 2004; Lohr, H. F., et al., *Clin. Exp. Immunol.* 130:107-104, 2002). Similarly impaired DC-$CD4^+$ T cell interactions are involved in the poor immune responses to and persistence of infection by Hepatitis C virus (HCV) (Murakami, H., et al. *Clin. Exp. Immunol.* 137:559-565, 2004).

Embodiments described herein relate to methods and compositions that alleviate or overcome the above-described challenges associated with the treatment of microbial infections, including those associated with HIV, herpes simplex virus (HSV), HBV, HCV, hepatitis G virus (HGV), human papilloma virus (HPV), cytomegalovirus (CMV), influenza virus, human T-cell leukemia virus (HTLV), Respiratory syncytial virus (RSV), Epstein Barr virus (EBV), measles virus, and Ebola virus, for example.

SUMMARY OF THE INVENTION

Embodiments of the present invention generally relate to a general manner of eliciting the induction, expansion and/or differentiation of the $CD8^+$ T cell population while eliciting only a modest or no $CD4^+$ T helper response (in a fashion independent of $CD4^+$ T helper response). Some embodiments include methods and compositions for inducing, entraining, and/or amplifying, the immune response to MHC class I-restricted HIV epitopes.

Some embodiments relate to methods of generating an immune response, including methods of immunization, that can include the steps of delivering to a lymphatic system of a mammal a composition that includes an immunogen, which immunogen includes a class I MHC-restricted epitope or a B cell epitope, wherein the immunogen does not include an effective class II MHC-restricted epitope; administering an immunopotentiator to the mammal; and obtaining or detecting an epitope-specific immune response without substantial activation or expansion of $CD4^+$ cells. The term "effective class II MHC-restricted epitope" as used herein can mean a peptide sequence that can be processed from the natural antigen and presented by a class II MHC molecule expressed by the species or individual in question so as to generate a class II restricted immune response. In preferred embodiments the epitope can be an HIV, HSV, HBV, HCV, HGV, HPV, CMV, influenza virus, HTLV, respiratory syncytial virus (RSV), EBV, measles virus, and Ebola virus epitope or an epitope associated with a target antigen for any disease in which avoidance of $CD4^+$ cell activation or expansion can be advantageous. Preferably, the immunogen and the immunopotentiator can be co-administered to the lymphatic system. Furthermore, in some preferred aspects the composition can include a first immunogen that includes a class I MHC-restricted epitope and a second immunogen that includes a B cell epitope, for example. Preferably, the first immunogen and the second immunogen can be the same. The method can further include co-administering a first immunogen that includes or encodes the class I MHC-restricted epitope with the immunopotentiator, and subsequently delivering a second immunogen that includes the epitope, in the form of an epitopic peptide, to the lymphatic system of the mammal. The interval between the administering step and the delivering step can be at least about seven days, for example. The first immunogen can include a nucleic acid encoding the epitope. The immunopotentiator can include, for example, a DNA molecule that includes a CpG sequence. The nucleic acid can include a DNA molecule that includes a CpG sequence which constitutes the immunopotentiator. The immunopotentiator can include, for example, a dsRNA. The first immunogen can include a polypeptide. In preferred embodiments the delivery to the lymphatic system can include delivery to a lymph node or a lymph vessel.

Some embodiments relate to methods that can include administering intranodally an adjuvant and peptide. Also, some other embodiments relate to inducing a response, and amplifying the response with peptide without requiring adjuvant for amplification. In some aspects, the amplification step can include the delivery of an immunogen along with a biological response modifier, such as an adjuvant. Preferably, in some aspects the amplification can be accomplished without adjuvant. Also, in some instances the amplification step can be performed without the delivery of any MHC class II restricted epitopes, thereby minimizing or avoiding any CD4$^+$ cells.

Also, some embodiments relate to methods of immunization, which can include, for example, a step for potentiating an immune response; a step for exposing the lymphatic system to a class I MHC-restricted epitope or a B cell epitope; and obtaining an epitope-specific immune response without substantial activation or expansion of CD4$^+$ cells.

Further embodiments relate to methods of immunization that include delivering to a mammal a first composition that includes an immunogen, which immunogen can include or encode at least a portion of a first antigen; administering a second composition that includes an amplifying peptide directly to a lymphatic system of the mammal, wherein the peptide corresponds to an epitope of said first antigen, wherein the first composition and the second composition are not the same, and inducing a cytotoxic T lymphocyte response without a T helper response. In some aspects, the immunogen can be an HIV, HSV, HBV, HCV, HPV, CMV, influenza virus, HTLV, respiratory syncytial virus (RSV), EBV, measles virus, or Ebola virus immunogen (or an immunogen that includes a sequence related to more than one of the same) and/or an immunogen associated with any disease in which avoidance of CD4$^+$ cell activation or expansion can be advantageous.

Preferably, the first antigen can be an HIV antigen. The first composition can include a nucleic acid encoding the antigen, the antigen or an immunogenic fragment thereof, or a nucleic acid capable of expressing the epitope in a pAPC, for example. The nucleic acid can be delivered as a component of a protozoan, bacterium, virus, viral vector, or the like. In some aspects the first composition can include an immunogenic polypeptide and an immunopotentiator. Preferably, the immunopotentiator can be a T1 biasing cytokine, for example, IL-12, IFN-gamma, or the like. Also, the immunopotentiator can be a T1 biasing toll-like receptor ligand. The adjuvant can be an immunostimulatory sequence. The adjuvant can include RNA. The immunogenic polypeptide can be an amplifying peptide. The immunogenic polypeptide can be the first antigen. The immunogenic polypeptide can be delivered as a component of a protozoan, bacterium, virus, viral vector, virus-like particle, or the like. The adjuvant can be delivered as a component of a protozoan, bacterium, virus, viral vector, virus-like particle, or the like. The second composition can be adjuvant-free and immunopotentiator-free. The delivering step can include direct administration to the lymphatic system of the mammal. In some aspects the direct administration to the lymphatic system of the mammal can include direct administration to a lymph node or lymph vessel. The direct administration can be to two or more lymph nodes or lymph vessels. The lymph node can be, for example, inguinal, axillary, cervical, or tonsillar lymph nodes. The method can further include obtaining an effector T cell response to the first antigen, and the effector T cell response can include production of a pro-inflammatory cytokine, including, for example, gamma-IFN or TNFα (alpha). The effector T cell response can include the production of a T cell chemokine, for example, RANTES or MIP-1α. The epitope can be a housekeeping epitope or an immune epitope, for example. The terms "housekeeping epitope" and "immune epitope" are defined in U.S. Publication No. 2003-0215425, which is incorporated herein by reference in its entirety. The delivering step or the administering step can include a single bolus injection, repeated bolus injections, or a continuous infusion, for example. The infusion can have a duration of between about 8 hours to about 7 days, for example. The method can include an interval between termination of the delivering step and beginning the administering step, wherein the interval is at least about seven days, between about 7 and about 14 days, or from about 14 to about 75 days, or over about 75 days for example. The method can be used for treating AIDS. The first antigen can be a target-associated antigen. The target can be an HIV infected cell, for example. Additionally, the method can be used to treat other viral infections or any disease where avoidance of CD4$^+$ cell activation or expansion can be advantageous. Examples of viral infections include those caused by HSV, HBV, HCV, HPV, CMV, influenza virus, HTLV, respiratory syncytial virus (RSV), EBV, measles virus, or Ebola virus. The effector T cell response can be detected by at least one indicator, for example, a cytokine assay, an Elispot assay, a cytotoxicity assay, a tetramer assay, a DTH-response, a clinical response, decrease pathogen titre, pathogen clearance, amelioration of a disease symptom, or the like. The effector T cell response can be a cytotoxic T cell response.

Some embodiments relate to methods of generating an immune response, including methods of immunization against HIV, HSV, HBV, HCV, HPV, CMV, influenza virus, HTLV, EBV, respiratory syncytial virus (RSV), measles virus, Ebola virus, or any disease where avoidance of CD4$^+$ cell activation or expansion can be advantageous. The methods can include, for example, delivering to a mammal a first composition that includes a a first antigen, an immunogenic fragment thereof, or a nucleic acid encoding the either of the same; and administering a second composition that includes a peptide, directly to the lymphatic system of the mammal, wherein the peptide corresponds to an epitope of the first antigen. The method can further include obtaining an effector T cell response to the antigen.

Some embodiments relate to methods of augmenting an existing antigen-specific immune response that includes administering a composition that includes a peptide, directly to the lymphatic system of a mammal, wherein the peptide corresponds to an epitope of said antigen, and wherein said composition was not used to induce the immune response; and obtaining augmentation of an HIV antigen-specific immune response. The augmentation can include sustaining the response over time, reactivating quiescent T cells, including CD8$^+$ cells. The augmentation can include expanding the population of HIV antigen-specific T cells. In some aspects the composition does not include an immunopotentiator, while in others it does include an immunopotentiator. The antigen-specific immune response can be, for example, an HIV, HSV, HBV, HCV, HPV, CMV, influenza virus, HTLV, respiratory syncytial virus (RSV), EBV, measles virus, or Ebola virus antigen-specific immune response, or antigen-specific immune response associated with any other disease where avoidance of CD4+ cell activation or expansion can be advantageous. Preferably, it is an HIV antigen-specific immune response.

Further embodiments relate to methods of immunization that include, for example, delivering to a mammal a first composition that includes an HIV immunogen, which immunogen includes or encodes at least a portion of a first antigen and at least a portion of a second antigen; and administering a second composition that includes a first peptide, and a third composition that includes a second peptide, directly to the lymphatic system of the mammal, wherein the first peptide corresponds to an epitope of said first antigen, and wherein the second peptide corresponds to an epitope of said second antigen, wherein the first composition is not the same as the second or third compositions. The method can further include obtaining an effector T cell response to the antigen. The second and third compositions each can include the first and the second peptides. It should be understood that in some embodiments the HIV immunogen mentioned above can be replaced by an HSV immunogen, an HBV immunogen, an HCV immunogen, an HPV immunogen, a CMV immunogen, an influenza virus immunogen, an HTLV immunogen, an RSV immunogen, an EBV immunogen, or a measles virus immunogen, an Ebola virus immunogen, or an immunogen associated with any other disease where avoidance or minimization of CD4+ activation or expansion can be advantageous.

Some embodiments relate to methods of immunization against HIV that include, for example, administering a series of immunogenic doses directly into the lymphatic system of a mammal wherein the series includes at least 1 entraining dose and at least 1 amplifying dose, and wherein the entraining dose includes a nucleic acid encoding an immunogen and wherein the amplifying dose is free of any virus, viral vector, replication-competent vector, or the like. The method can include about 1-6 entraining doses, for example, or even more than 6, for example, 1-7, 1-8, 1-9, 1-10 or more. The method can include administering a plurality of entraining doses, wherein the doses are administered over a course of one to about seven days. The entraining doses, amplifying doses, or entraining and amplifying doses can be delivered in multiple pairs of injections, wherein a first member of a pair is administered within about 1, 2, 3, 4 or 5 days and preferably within about 4 days of a second member of the pair, and wherein an interval between first members of different pairs is at least about, 6, 7, 8, 9, 10, 11, 12, 13, 14, 15, 16, 17, 18, 19 or 20 days, for example. Preferably, an interval between first members of different pairs is at least about 14 days, for example. The interval between a last entraining dose and a first amplifying dose can be between about 1 and about 150 days, about 3 and about 125 days, and preferably about 7 and about 100 days, for example. The method can further include obtaining an antigen-specific immune response. It should be understood that in some embodiments, the above-mentioned methods of immunization against HIV can be modified to generate an immune response, including immunization against HSV, HBV, HCV, HPV, CMV, influenza virus, HTLV, RSV, EBV, measles virus, Ebola virus, or against any other disease where avoidance or minimization of CD4+ activation or expansion can be advantageous.

Also, some embodiments relate to sets of immunogenic compositions for inducing an immune response in a mammal that includes about 1-6 or more entraining doses and at least one amplifying dose, wherein the entraining doses includes a nucleic acid encoding an HIV immunogen, and wherein the amplifying dose includes a peptide epitope, and wherein the epitope is presented by pAPC expressing the nucleic acid. In some aspects, the sets of compositions can include more than 6 entraining doses, for example, about 1-7, 1-8, 1-9, 1-10 or more. In some aspects at least one dose further can include an adjuvant, for example, RNA. The entraining and amplifying doses can be in a carrier suitable for direct administration to the lymphatic system, for example a lymph node. The nucleic acid can be a plasmid. The epitope can be a class I MHC epitope. The MHC can be any MHC, including, for example, those listed in Tables 1-4, including combinations of the same, while other embodiments specifically exclude any one or more of the MHCs or combinations thereof. Tables 3-4 include frequencies for the listed HLA antigens. Preferably, the HLA can be, for example, HLA-A2, HLA-B7, and the like. The immunogen can include an epitope array, which can include, for example, a liberation sequence. The term "liberation sequence" as used herein is defined in U.S. Publication No. 2003-0228634, published on Dec. 11, 2003, which is incorporated herein by reference in its entirety. The immunogen can be a target-associated antigen, for example, an antigen from an HIV infected cell. The immunogen can be a fragment of a target-associated antigen that includes an epitope cluster. It should be understood that in some embodiments the nucleic acid encoding the HIV immunogen mentioned above, can be replaced by a nucleic acid encoding one or more of the following: an HSV immunogen, an HBV immunogen, an HCV immunogen, an HPV immunogen, a CMV immunogen, an influenza virus immunogen, an HTLV immunogen, an RSV immunogen, an EBV immunogen, or a measles virus immunogen, an Ebola virus immunogen, or an immunogen associated with any other disease where avoidance or minimization of CD4+ activation or expansion can be advantageous.

Further embodiments relate to sets of immunogenic compositions for inducing a class I MHC-restricted immune response in a mammal, which methods can include, for example, 1-6, or more, entraining doses and at least one amplifying dose, wherein the entraining doses include an HIV immunogen (or other immunogen as described above or elsewhere herein) or a nucleic acid encoding an immunogen (or encoding another immunogen as described above or elsewhere herein) and an immunopotentiator, and wherein the amplifying dose includes a peptide epitope, and wherein the epitope is presented by pAPC. In some aspects, the sets of compositions can include more than 6 entraining doses, for example, about 1-7, 1-8, 1-9, 1-10 or more. The nucleic acid encoding the HIV immunogen further can include an immunostimulatory sequence which serves as the immunopotentiating agent. The immunogen can be, for example, a virus or replication competent vector that includes or induces an immunopotentiating agent. The immunogen can be, for example, a bacterium, bacterial lysate, purified cell wall component, or the like, wherein the bacterial cell wall component is capable of functioning as the immunopotentiating agent. The immunopotentiating agent can be, for example, a TLR ligand, an immunostimulatory sequence, a CpG-containing DNA, a dsRNA, an endocytic-Pattern Recognition Receptor (PRR) ligand, a lipopolysacharide (LPS), a *quillaja saponin*, tucaresol, a pro-inflammatory cytokine, and the like.

Some embodiments relate to methods of immunization, which methods can include the step of delivering to a mammal a first composition that includes a first immunogen, the first immunogen including or encoding at least a portion of a first antigen; and subsequently administering a second composition that includes an epitopic peptide directly to the lymphatic system of the mammal, wherein the peptide corresponds to a class I MHC-restricted epitope of the first antigen, wherein the second composition is not the same as the first composition such that an epitope-specific immune response is amplified without substantial activation or expansion of CD4+ T cells. In some aspects, the delivering step can further include the delivery of an immunopotentiator or adjuvant.

Also, some embodiments relate to methods of generating an immune response against a disease-related antigen in which it is advantageous to minimize the expansion of CD4+ lymphocytes. The methods can include delivering to an animal a first immunogen and an immunopotentiator, the first immunogen including or encoding at least a first portion of a first antigen, wherein the at least a portion of a first antigen does not include a class II MHC restricted epitope for an MHC expressed by the animal; and administering, preferably after the delivering step, an epitopic peptide directly to a lymphatic system of the animal, wherein the peptide corresponds to a class I MHC-restricted epitope of the first antigen, wherein the epitopic peptide is not the same as the first immunogen. The animal can be, for example, a human or a non human, preferably a mammal. In some aspects the animal can be, for example, a feline, a canine, an avian such as for example, a chicken or a turkey, a bovine, an equine, other livestock or farm animals, or any other animal. In some embodiments, the at least a portion of a first antigen can include a class II restricted epitope.

In some embodiments the term "corresponds" can mean that the peptide has the wild-type or native epitope sequence from the antigen or that the peptide is cross-reactive or an analog of the wild-type epitope sequence. Examples of such cross-reactive and analogs, including how to make the same, are found in U.S. Patent Publication No. 2003-0220239, published on Dec. Nov. 27, 2003; U.S. patent application Ser. No. 11/155,929, filed on Jun. 17, 2005, entitled NY-ESO-1 PEPTIDE ANALOGS; and U.S. patent application Ser. No. 11/156,253, filed on Jun. 17, 2005, entitled SSX-2 PEPTIDE ANALOGS; each of which is incorporated herein by reference in its entirety.

The disease is caused by, for example, HIV, HSV, HBV, HCV, HGV, EBV, HPV, CMV, influenza virus, HTLV, RSV, EBV, measles virus, Ebola virus, and the like. The first immunogen and the immunopotentiator can be delivered to a lymphatic system of the animal, for example to a lymph node or a lymph vessel. The first immunogen and the immunopotentiator can be delivered to a same location on or in the animal. Also, they can be delivered simultaneously, for example at the same time or within about 1-2 minutes of each other or over a period of time together. They can be delivered within more than 2 minutes, for example, within about 3, 4, 5, 6, 7, 8, 9, or 10 minutes, within 15, 30, 45 or 60 minutes of each other, within 1, 2, 3, 4, 5, 6, 7, 8, 9, 10, 11 or 12 hours, or within the same day. Further, the epitopic peptide can be delivered to a lymphatic system of the animal, for example to a lymph node or a lymph vessel. The first immunogen and the immunopotentiator can be delivered as part of a same composition.

The at least a portion of a first antigen can include, for example, a whole antigen, less than the full-length of a whole antigen, a contiguous fragment of less than 80%, 70%, 60%, 50%, %, 40%, 30%, 20% or 10% of the whole antigen, one or more class I T cell epitope, B cell epitope, or combinations thereof, a chimeric molecule that includes more than one class I T cell epitope, B cell epitope, or combinations thereof, and the like. The first immunogen can encode the at least a portion of a first antigen and can include an immunostimulatory sequence that serves as the immunopotentiator. The first immunogen can encode one or more epitopes, wherein the one or more epitopes are class I restricted T cell epitopes or B cell epitopes. The first immunogen can encode a chimeric nucleic acid sequence that includes more than one class I T cell epitope, B cell epitope, or a combination thereof. The immunogen as used in the delivering step can also be any other immunogen, including those described elsewhere herein and in the listed and incorporated references.

The administering step can be performed subsequent to the delivering step, for example, about 1, 2, 3, 4, 5, or 6 days after, preferably about 7, 8, 9, 10, 11, 12, 13, 14, 15, 20, 25, 30 days or more after the delivering step.

Also, in some instances, the at least a first portion of a first antigen does not include or encode any MHC class II restricted epitope for the species of the animal, or does not include or encode any human class II restricted epitope. The first immunogen further can include or encodes at least a second portion of the first antigen, wherein the at least a second portion of the first antigen does not include a class II MHC restricted epitope for an MHC expressed by the animal. The first immunogen can encode the at least a first portion a first antigen and the at least a second portion of the first antigen. The first immunogen further can include or encode one or more additional portions of the first antigen, wherein the one or more additional portions of the first antigen do not include a class II MHC restricted epitope for an MHC expressed by the animal. The first immunogen further can include or encode at least a first portion of a second antigen. The delivering step further can include delivering a second immunogen that includes or encoding at least a first portion of a second antigen, wherein the at least a first portion of a second antigen does not include a class II MHC restricted epitope for an MHC expressed by the animal. The methods further can include detecting or obtaining an epitope-specific immune response without substantial activation or expansion of CD4+ T cells. The detection or determination of obtaining can be done by any suitable method.

In some embodiments, "substantial" can be used in the context of "substantial activation or expansion" of, for example, CD4+ T cells. In this context, "substantial activation or expansion" generally indicates a level of activation or expansion that would reach a level of physiological significance or disease significance beyond mere detectability. For example, if a population of CD4+ T cells activated or expanded at a level above the detection cutoff, but below a level that would change the characteristics of the population to function as a target population for infectious agents or to fulfill other functions of the population, but below a level that would produce a clinically relevant change in the characteristics, it is understood that the population has not experienced substantial activation or expansion.

Also, some embodiments relate to methods of generating an immune response against an HIV infection. The methods can include the steps of delivering to an animal a composition that includes a nucleic acid encoding first immunogen and that includes an immunostimulatory sequence that can serve as an immunopotentiator, the nucleic acid encoding at least a first portion of a first HIV antigen, wherein the at least a portion of a first antigen does not include a class II MHC restricted epitope for an MHC expressed by the animal; and administering, preferably subsequent to the delivering step, an epitopic peptide directly to a lymphatic system of the animal, wherein the peptide corresponds to a class I MHC-restricted epitope of the at least a first portion of a first HIV antigen, wherein the epitopic peptide is not the same as the first immunogen. In some embodiments, the at least a portion of a first HIV antigen can include a class II restricted epitope. The first HIV antigen can be, for example, gag, pol, env, tat, gp120, gp160, gp41, nef, gag p, gp, gag p24, rt, and the like.

The nucleic acid can encode one or more of SEQ ID NOs:1-531, preferably one or more of SEQ ID NOs:1-6, or any other HIV epitope.

Further, some embodiments relate to methods of generating an immune response against a cell infected by an HIV. The methods can include delivering to patient a composition that includes a nucleic acid encoding one or more of SEQ ID NOs:1-531, preferably one or more of SEQ ID NOs:1-531, and an adjuvant, the nucleic acid can encode at least a first portion of a first HIV antigen, wherein the at least a portion of a first antigen does not include a class II MHC restricted epitope for an MHC expressed by the patient, wherein the adjuvant can any adjuvant, preferably a CpG, a dsRNA poly IC, or a TLR mimic; and administering, preferably after the delivering step, one or more epitopic peptides directly to a lymph node of the patient, wherein the peptide is one that was encoded by the nucleic acid or is an analog thereof. In some embodiments, the at least a portion of a first HIV antigen can include a class II restricted epitope.

Some embodiments relate to sets of immunogenic compositions, which can include, for example, any of the compositions described herein, including as exemplified in the examples. Some embodiments relate to one or more immunogenic products, which can include, for example, one or more immunogens, viruses, vectors, antigens, peptides, epitopes, or combinations thereof. Also, some embodiments relate to kits that include one or more of the following: an immunogenic composition as described or exemplified herein, sets of such compositions, products, or sets of products, any other material, substance or composition of matter described herein, instructions for use, delivery vehicles, and combinations of any of the same.

Other embodiments relate to sets of immunogenic compositions for inducing an immune response in a mammal including 1 to 6 or more entraining doses and at least one amplifying dose, wherein the entraining doses can include a nucleic acid encoding an immunogen, and wherein the amplifying dose can include a peptide epitope, and wherein the epitope can be presented or is presentable by pAPC expressing the nucleic acid. The one dose further can include an adjuvant, for example, RNA. The entraining and amplifying doses can be in a carrier suitable for direct administration to the lymphatic system, a lymph node and the like. The nucleic acid can be a plasmid. The epitope can be a class I HLA epitope, for example, one listed in Tables 1-4. The HLA preferably can be HLA-A2. The immunogen can include an epitope array, which array can include a liberation sequence. The immunogen can consist essentially of a target-associated antigen. The target-associated antigen can be a tumor-associated antigen, a microbial antigen, any other antigen, and the like. The immunogen can include a fragment of a target-associated antigen that can include an epitope cluster.

Further embodiments can include sets of immunogenic compositions for inducing a class I MHC-restricted immune response in a mammal including 1-6 entraining doses and at least one amplifying dose, wherein the entraining doses can include an immunogen or a nucleic acid encoding an immunogen and an immunopotentiator, and wherein the amplifying dose can include a peptide epitope, and wherein the epitope can be presented by pAPC. The nucleic acid encoding the immunogen further can include an immunostimulatory sequence which can be capable of functioning as the immunopotentiating agent. The immunogen can be a virus or replication-competent vector that can include or can induce an immunopotentiating agent. The immunogen can be a bacterium, bacterial lysate, or purified cell wall component. Also, the bacterial cell wall component can be capable of functioning as the immunopotentiating agent. The immunopotentiating agent can be, for example, a TLR ligand, an immunostimulatory sequence, a CpG-containing DNA, a dsRNA, an endocytic-Pattern Recognition Receptor (PRR) ligand, an LPS, a *quillaja saponin*, tucaresol, a pro-inflammatory cytokine, and the like. In some preferred embodiments for promoting multivalent responses the sets can include multiple entraining doses and/or multiple amplification doses corresponding to various individual antigens, or combinations of antigens, for each administration. The multiple entrainment doses can be administered as part of a single composition or as part of more than one composition. The amplifying doses can be administered at disparate times and/or to more than one site, for example.

BRIEF DESCRIPTION OF THE DRAWINGS

FIG. 1: shows the cytolytic response to an HBV epitope induced by intranodal administration of peptide plus poly (IC).

FIG. 2: shows the cytolytic response to a PSMA model epitope induced by intranodal administration of peptide plus poly(IC).

FIG. 3: shows the cytolytic response to a pair of PRAME model epitopes induced by intranodal administration of peptide plus poly(IC).

FIG. 4: shows the specific susceptibility of $CD8^{\pm}$ lymphocytes to in vitro activation subsequent to immunization.

DETAILED DESCRIPTION OF THE PREFERRED EMBODIMENT

Some embodiments disclosed herein relate to methods and compositions for bypassing the involvement of $CD4^+$ cells when generating antibody and MHC class I-restricted immune responses, controlling the nature and magnitude of the response, and promoting effective immunologic intervention in viral pathogenesis, or in other settings in which avoidance of CD4+ cell activation or expansion can be advantageous. More specifically, some embodiments relate to immunogenic compositions for vaccination, particularly therapeutic vaccination against HIV, HSV, HBV, HCV, HPV, CMV, influenza virus, HTLV, RSV, EBV, measles virus, Ebola virus and other microbial pathogens that impact functioning of the immune system, their nature, and the order, timing, and route of administration by which they are effectively used. Some embodiments relate to methods of generating an immune response against HIV, HSV, HBV, HCV, HPV, CMV, influenza virus, HTLV, RSV, EBV, measles virus, Ebola virus and other microbial pathogens while minimizing, limiting or preventing adverse effects associated with the activation or expansion of $CD4^+$ cells. Various examples of viruses and microbes are provided in Tables 5-7 and in the other references mentioned herein which are incorporated by reference in their entirety. Other embodiments relate to methods for expanding the $CD8^+$ and/or antibody response while mitigating any ill effect caused by the activation or expansion of the $CD4^+$ subset. Further embodiments relate to methods for expanding the $CD8^+$ and/or antibody response while overcoming any impairment of $CD4^+$ T cell responses. Also, some embodiments relate to methods of amplifying an anti-HIV $CD8^+$ T cell and/or antibody response while causing little or no effect on, or expansion of $CD4^+$ cells. Such embodiments can also be particularly useful in situations where an antigen is prone to generating undesired $CD4^+$ T regulatory cells, or in which $CD4^+$ T cells contribute to an immunopathology.

Methods and compositions disclosed herein are useful in the generation of an immune response or a therapeutic response to HIV, HSV, HBV, HCV, HPV, CMV, influenza virus, HTLV, RSV, EBV, measles virus, Ebola virus which can be accomplished in a manner that avoids concerns that the immunization process itself will promote spread of the infection and exacerbate progression of related disease and in addition, in a manner that does not require a fully functional Th cell population.

Some embodiments relate to a two-stage immunization protocol for the generation of a CTL response. In the first stage an immune response comprising a memory CTL response to one or more class I MHC-restricted epitopes of the target antigen can be established. Typically this can be accomplished by intranodal administration of a naked DNA plasmid capable of expression of an appropriate antigen in a professional antigen presenting cell (pAPC). In other preferred embodiments immunogen can be combined with an appropriate toll-like receptor (TLR) ligand such as a CpG oligonucleotide or synthetic dsRNA (polyI:C). Intralymphatic administration however, is not an essential feature of this first stage of the protocol, and more conventional routes of administration can be used. In preferred embodiments the term "immunogen" can be defined as a molecule capable of inducing an immune response against an antigen, a vector expressing such a molecule, or a composition comprising one or more such molecules or vectors.

The magnitude of the response at this stage is not crucial. Quite modest responses suffice, although moderate and strong responses can also occur, and thus, the involvement of $CD4^+$ responses can be tolerated at this stage of the procedure without destroying the usefulness of the complete protocol. $CD4^+$ responses can generally be avoided by use of immunogens that do not comprise or express class II MHC-restricted epitopes, or at least not ones that can be presented by the class II MHC alleles expressed by a particular subject.

Immunogens that do contain potentially problematic class II MHC-restricted epitopes can be modified, for example, by deletion, mutation, or any other modification of the epitope(s) so as to inhibit or prevent processing, transport, and/or MHC-binding of the class II epitope. The immunopotentiator used in the first stage generally can be one that acts primarily on pAPC, for example, dendritic cells, and not directly on lymphocytes. Thus, they will not be a major cause of activation or proliferation of $CD4^+$ lymphocytes. Intranodal administration can further reduce any generalized effects of these agents.

In the second stage of this protocol one or more epitopic peptides corresponding to the epitope(s) immunized against in the first stage, can be administered directly to the lymphatic system. In preferred embodiments the term "epitopic peptide" can mean a peptide that comprises, consists essentially of, or consists of an epitope. The peptide(s) can be used without any immunopotentiator or other adjuvant, although immunopotentiators or other adjuvants optionally can be used. In preferred embodiments administration can be directly to a lymph node, and in the case of multiple peptides it can be preferred that only a single peptide be administered to any particular lymph node on any particular occasion, although in some aspects the more than one or all peptides can be administered to the same lymph node. In some embodiments, for example those promoting a multivalent response and in which multiple amplifying peptides are used, it can be advantageous that only a single peptide be administered to any particular lymph node on any particular occasion. Thus, one peptide can be administered to the right inguinal lymph node and a second peptide to the left inguinal lymph node at the same time, for example. Additional peptides can be administered to other lymph nodes even if they were not sites of induction as it is not essential that initiating and amplifying doses be administered to the same site due to migration of T lymphocytes. Alternatively any additional peptides can be administered about one or two days later to the same lymph node(s), preferably, about three, four, five or six days later to the same lymph node(s) used for the previously administered amplifying peptides since the time interval between induction and amplification is not a crucial parameter, although in preferred embodiments the time interval can be greater than about a week, for example, about seven, eight, nine, ten, eleven, twelve, thirteen, fourteen or more days later. Segregation of administration of amplifying peptides generally can be of less importance if their MHC-binding affinities are similar, but grows in importance as the affinities become more disparate. Incompatible formulations of various peptides can also make segregated administration preferable. Where the MHC-binding affinities of the various peptides are similar, it can be less preferred that the administration or only a single peptide be administered to a particular lymph node during a particular occasion. Where the MHC binding affinities of the various peptides are or become more disparate, it can be more preferred that only a single peptide be administered to any particular lymph node on any particular occasion. Such peptides will generally not bind to class II MHC markers, so typically only the class I-restricted, $CD8^+$ response will be amplified. Further details related to this methodology are described in U.S. patent application Ser. No. 10/871,707 (Pub. No. 2005-0079152 A1), filed on Jun. 17, 2004, Publication No. 20050079152A1, entitled METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES, which is incorporated herein by reference in its entirety. Additional methodology related to generating immune responses, including multivalent responses, is disclosed in U.S. Provisional Patent Application No. 60/640,402, filed on Dec. 29, 2004 and in nonprovisional U.S. patent application Ser. No. 11/323,572 (Publication No. 2006-0165722), filed on the same date as this application, both entitled METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES, each of which is incorporated herein by reference in its entirety. Intralymphatic immunization for the induction of CTL responses is taught in U.S. patent application Ser. Nos. 09/380,534; 09/776,232 (Publication No. 20020007173), now U.S. Pat. No. 6,977,074, filed on Feb. 6, 2001, entitled METHOD OF INDUCING A CTL RESPONSE each of which is incorporated, herein by reference in its entirety.

In some embodiments, an immunogen can be co-administered intralymphatically with an immunopotentiating biological response modifier (BRM). In one aspect the immunogen can include one or more class I MHC-restricted peptide epitopes and a CTL response can be generated. In another aspect the immunogen can include one or more B cell epitopes and an antibody response can be generated. In either aspect, it can be preferred that the immunogen lacks class II MHC-restricted epitopes, or at least ones that can be presented by the class II MHC alleles expressed by a particular subject. This feature can be ensured by using in silico predictive methods and standard characterization of peptide binding to MHC class I and II molecules, using well known experimental methods. The use and advantages of intralymphatic administration of BRMs are disclosed in co-pending provisional U.S. Patent Application No. 60/640,727, filed on Dec. 29, 2004, and in nonprovisional U.S. patent application Ser. No. 11/321,967, filed on the same date as this application, both entitled METHODS TO TRIGGER, MAINTAIN AND MANIPULATE IMMUNE RESPONSES BY TARGETED ADMINISTRATION OF BIOLOGICAL RESPONSE MODIFIERS INTO LYMPHOID ORGANS, each of which is incorporated herein by reference in its entirety.

In some embodiments, preferred immunogens for class I MHC-restricted epitopes are epitopic peptides. As in the immunization protocol above, it can be preferred to administer only a single peptide to any particular lymph node on any particular occasion. For B cell epitopes, free peptides are not ideal immunogens. Preferably the target epitope is multivalent in the immunogen. Examples include multiple conjugation to a carrier protein; recombinant proteins and polypeptides comprising the epitope, for example, IgG with the epitope grafted into the CDR3 position; Ig-peptide fusion proteins (with peptide at N or C terminal position); and iterative chains of the epitope with or without spacer sequences; and dendrimers. It is preferred that any carrier protein, whether monovalent or multivalent for the epitope, be a self-protein so that the recipient will have at least a degree of tolerance for any presentable class II MHC-restricted epitopes in the carrier. In humans, human serum albumin and immunoglobulins are potential choices as carriers. $CD8^+$ cells secrete various cytokines in addition to having cytolytic activity. Thus immunization with both types of immunogen can improve the response to the B cell immunogen, especially in the case that the B cell immunogen is monovalent for the target epitope.

The disclosed methods are advantageous over many protocols in HIV vaccine therapeutics. Current vaccines commonly rely on interaction with, or result in expansion of the $CD4^+$ population in an attempt to control viral infection, but can in fact detrimentally provide new targets for viral infection. The disclosed DNA prime-peptide boost method is itself advantageous over other protocols that use only peptide or do not follow the entrain-and-amplify methodology. The peptide based immunization or immune amplification strategy has advantages over other methods, particularly certain microbial vectors, for example. This is due to the fact that more complex vectors, such as live attenuated viral or bacterial vectors, may induce deleterious side-effects, for example, in vivo replication or recombination; or become ineffective upon repeated administration due to generation of neutralizing antibodies against the vector itself. Additionally, when harnessed in such a way to become strong immunogens, peptides can circumvent the need for proteasome-mediated processing (as with protein or more complex antigens, in context of "cross-processing" or subsequent to cellular infection). That is because cellular antigen processing for MHC-class I restricted presentation is a phenomenon that inherently selects dominant (favored) epitopes over subdominant epitopes, potentially interfering with the immunogenicity of epitopes corresponding to valid targets. Thus, if antigen presenting cells are defective, use of peptides may circumvent the need for competent processing that is a prerequisite for effectiveness of complex vectors. Finally, effective peptide based immunization simplifies and shortens the process of development of immunotherapeutics.

Thus, effective peptide-based immune amplification methods, particularly including those described herein, can be of considerable benefit to prophylactic and/or therapeutic generation of an immune response against HIV, HSV, EBV, HBV or HCV, including benefit for vaccination against the same. Additional benefits can be achieved by avoiding simultaneous use of cumbersome, unsafe, or complex adjuvant techniques, although such techniques can be utilized in various embodiments described herein.

Previous HIV immunization methods displayed certain important limitations including that the high mutation rate of HIV creates immune escape mutants with ease, and viral surface protein gp120 is a poor immunogen inherently resistant to antibody attack. Immunization methods in general also displayed certain limitations: very often, conclusions regarding the potency of vaccines were extrapolated from immunogenicity data generated from one or from a very limited panel of ultrasensitive read-out assays. Frequently, despite the inferred potency of a vaccination regimen, the clinical response was not significant or was at best modest. Secondly, subsequent to immunization, T regulatory cells, along with more conventional T effector cells, can be generated and/or expanded, and such cells can interfere with the function of the desired immune response. The importance of such mechanisms in active immunotherapy has been recognized only recently.

Intranodal administration of immunogens provides a basis for the control of the magnitude and profile of immune responses. The effective in vivo loading of pAPC accomplished as a result of such administration, enables a substantial magnitude of immunity, even by using an antigen in its most simple form—a peptide epitope—otherwise generally associated with poor pharmacokinetics. The quality of response can be further controlled via the nature of immunogens, vectors, and protocols of immunization. Such protocols can be applied for enhancing/modifying the response in infections such as HIV. Further, intranodal administration of BRMs allows one to take advantage of their immunopotentiating activity while avoiding the toxicity commonly associated with otherwise required dosages.

Immunization has traditionally relied on repeated administration of antigen to augment the magnitude of the immune response. The use of DNA vaccines has resulted in high quality responses, but it has been difficult to obtain high magnitude responses using such vaccines, even with repeated booster doses. Both characteristics of the response, high quality and low magnitude, are likely due to the relatively low levels of epitope loading onto MHC achieved with these vectors. Instead it has become more common to boost such vaccines using antigen encoded in a live virus vector in order to achieve the high magnitude of response needed for clinical usefulness. However, the use of live vectors can entail several drawbacks including potential safety issues, decreasing effectiveness of later boosts due to a humoral response to the vector induced by the prior administrations, and the costs of creation and production. Thus, use of live vectors or DNA alone, although eliciting high quality responses, may result in a limited magnitude or sustainability of response due to a reduced in vivo transfection rate (former) or generation of anti-vector neutralizing responses (the latter).

Disclosed herein are embodiments that relate to protocols and to methods that, when applied to peptides, rendered them effective as immune therapeutic tools. Such methods circumvent the poor PK of peptides, and if applied in context of specific, and often more complex regimens, result in robust amplification and/or control of immune response. In preferred embodiments, direct administration of peptide into lymphoid organs results in unexpectedly strong amplification of immune responses, following a priming agent that induces a strong, moderate or even mild (at or below levels of detection by conventional techniques) immune response consisting of Tc1 cells. While preferred embodiments can employ intralymphatic administration of antigen at all stages of immunization, intralymphatic administration of adjuvant-free peptide can be most preferred. Peptide amplification utilizing intralymphatic administration can be applied to existing immune responses that may have been previously induced. Previous induction can occur by means of natural exposure to the antigen or by means of commonly used routes of administration, including without limitation subcutaneous, intradermal, intraperitoneal, intramuscular, and mucosal.

Also as shown herein, optimal initiation, resulting in subsequent expansion of specific T cells, can be better achieved by exposing the naive T cells to limited amounts of antigen (as can result from the often limited expression of plasmid-encoded antigen) in a rich co-stimulatory context (such as in a lymph node). That can result in activation of T cells carrying T cell receptors that recognize with high affinity the MHC-peptide complexes on antigen presenting cells and can result in generation of memory cells that are more reactive to subsequent stimulation. The beneficial co-stimulatory environment can be augmented or ensured through the use of immunopotentiating agents and thus intralymphatic administration, while advantageous, is not in all embodiments required for initiation of the immune response.

While the poor pharmacokinetics of free peptides has prevented their use in most routes of administration, direct administration into secondary lymphoid organs, particularly lymph nodes, has proven effective when the level of antigen is maintained more or less continuously by continuous infusion or frequent injection (for example, daily). Such intranodal administration for the generation of CTL is taught in U.S. patent application Ser. Nos. 09/380,534; 09/776,232 (Pub. No. 20020007173A1), now U.S. Pat. No. 6,977,074; in PCT Application No. PCTUS98/14289 (Pub. No. WO 99/02183 A2) each entitled METHOD OF INDUCING A CTL RESPONSE and in U.S. application Ser. No. 10/871,707 (Pub. No. 2005-0079152 A1), filed on Jun. 17, 2004, entitled METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES, each of which is hereby incorporated by reference in its entirety. Intranodal administration of peptide was effective in amplifying a response initially induced with a plasmid DNA vaccine. Moreover, the cytokine profile was distinct, with plasmid DNA induction/peptide amplification generally resulting in greater chemokine (chemoattractant cytokine) and lesser immunosuppressive cytokine production than either DNA/DNA or peptide/peptide protocols.

Thus, such DNA inductiodpeptide amplification protocols can improve the effectiveness of compositions, including therapeutic vaccines for cancer and chronic infections. Beneficial epitope selection principles for such immunotherapeutics are disclosed in U.S. patent application Ser. Nos. 09/560,465, 10/026,066 (Pub. No. 20030215425 A1), Ser. No. 10/005,905, filed Nov. 7, 2001, Ser. No. 10/895,523 (Pub. No. 2005-0130920 A1), filed Jul. 20, 2004, and Ser. No. 10/896,325 (Pub No. 2007-0184062 A1), filed Jul. 20, 2004, all entitled EPITOPE SYNCHRONIZATION IN ANTIGEN PRESENTING CELLS; Ser. No. 09/561,074, now U.S. Pat. Nos. 6,861,234, and 10/956,401 (Pub. No. 2005-0069982 A1), filed on Oct. 1, 2004, both entitled METHOD OF EPITOPE DISCOVERY; Ser. No. 09/561,571, filed Apr. 28, 2000, entitled EPITOPE CLUSTERS; Ser. No. 10/094,699 (Pub. No. 20030046714 A1), filed Mar. 7, 2002, Ser. No. 11/073,347, (Pub. No. 2005-0260234 A1), filed Jun. 30, 2005, each entitled ANTI-NEOVASCULATURE PREPARATIONS FOR CANCER; and Ser. No. 10/117,937 (Pub. No. 20030220239 A1), filed Apr. 4, 2002, Ser. No. 11/067,159 (Pub. No. 2005-0221440A1), filed Feb. 25, 2005, Ser. No. 10/067,064 (Pub. No. 2005-0142114 A1), filed Feb. 25, 2005, and Ser. No. 10/657,022 (Publication No 2004-0180354 A1), and PCT Application No. PCT/US2003/027706 (Pub. No. WO 04/022709 A2), each entitled EPITOPE SEQUENCES, and each of which is hereby incorporated by reference in its entirety. Aspects of the overall design of vaccine plasmids are disclosed in U.S. patent application Ser. No. 09/561,572, filed Apr. 28, 2000, and Ser. No. 10/225,568 (Pub. No. 2003-0138808 A1), filed Aug. 20, 2002, both entitled EXPRESSION VECTORS ENCODING EPITOPES OF TARGET-ASSOCIATED ANTIGENS and U.S. patent application Ser. No. 10/292,413 (Pub. No. 20030228634 A1), Ser. No. 10/777,053 (Pub. No. 2004-0132088 A1), filed on Feb. 10, 2004, and Ser. No. 10/837,217 (Pub. No. 2004-0203051 A1), filed on Apr. 30, 2004, all entitled EXPRESSION VECTORS ENCODING EPITOPES OF TARGET-ASSOCIATED ANTIGENS AND METHODS FOR THEIR DESIGN; Ser. No. 10/225,568 (Pub No. 2003-0138808 A1), PCT Application No. PCT/US2003/026231 (Pub. No. WO 2004/018666) and U.S. Pat. No. 6,709,844 and U.S. patent application Ser. No. 10/437,830 (Pub. No. 2003-0180949 A1), filed on May 13, 2003, each entitled AVOIDANCE OF UNDESIRABLE REPLICATION INTERMEDIATES IN PLASMID PROPAGATION, each of which is hereby incorporated by reference in its entirety. Specific antigenic combinations of particular benefit in directing an immune response against particular cancers are disclosed in provisional U.S. Provisional Application No. 60/479,554, filed on Jun. 17, 2003, U.S. patent application Ser. No. 10/871,708 (Pub. No. 2005-0118186 A1), filed on Jun. 17, 2004, PCT Patent Application No. PCT/US2004/019571 (Pub. No. WO 2004/112825), U.S. Provisional Application No. 60/640,598, filed. Dec. 29, 2005, and U.S. patent application Ser. No. 11/323,049 (Pub. No. 2006-0159694), filed on the same date as this application, all entitled COMBINATIONS OF TUMOR-ASSOCIATED ANTIGENS IN VACCINES FOR VARIOUS TYPES OF CANCERS, each of which is also hereby incorporated by reference in its entirety. Specific antigenic combinations of particular benefit in directing an immune response against HIV are disclosed in an article by Kiepiela et al., ("Dominant influence of HLA-B in mediating the potential co-evolution of HIV and HLA," Nature, vol. 432, pages 769-775 (Dec. 9, 2004), which is also hereby incorporated by reference in its entirety.

The use and advantages of intralymphatic administration of BRMs are disclosed in provisional U.S. Patent Application No. 60/640,727, filed. Dec. 29, 2005 and U.S. patent application Ser. No. 11/321,967 (Pub. No. 2006-0153844 A1), filed on the same date as this application, both entitled Methods to trigger, maintain and manipulate immune responses by targeted administration of biological response modifiers into lymphoid organs, each of which is incorporated herein by reference in it entirety. Additional methodology, compositions, peptides, and peptide analogues are disclosed in U.S. patent application Ser. No. 09/999,186, filed Nov. 7, 2001, entitled METHODS OF COMMERCIALIZING AN ANTIGEN; and U.S. Provisional Patent Application No. 60/640,402, filed Dec. 29, 2005 and application Ser. No. 11/323,572, (Pub. No. 2006-0165711), filed on the same date as this application, both entitled METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES, each of which is hereby incorporated by reference in its entirety.

The integration of diagnostic techniques to assess and monitor immune responsiveness with methods of immunization is discussed more fully in Provisional. U.S. Patent Application No. 60/580,964, filed Jun. 17, 2004, and Ser. No. 11/155,928 (Pub. No. 2005-0287068 A1), filed Jun. 17, 2005, both entitled IMPROVED EFFICACY OF ACTIVE IMMUNOTHERAPY BY INTEGRATING DIAGNOSTIC WITH THERAPEUTIC METHODS, each of which is hereby incorporated by reference in its entirety. Additional methodology, compositions, peptides, and peptide analogues are disclosed in U.S. Provisional Patent Application No. 60/581,001, filed on Jun. 17, 2004 and U.S. patent application Ser. No. 11/156,253 (Pub. No. 2006-0063913 A1), filed on Jun. 17, 2005, both entitled SSX-2 PEPTIDE ANALOGS; and U.S. Provisional Patent Application No. 60/580,962, filed on Jun. 17, 2004, and U.S. patent application Ser. No. 11/155,929 (Pub. No 2006-0094661 A1), filed on Jun. 17, 2005, both entitled NY-ESO PEPTIDE ANALOGS; U.S. patent application Ser. No. 09/999,186, filed Nov. 7, 2001, entitled METHODS OF COMMERCIALIZING AN ANTIGEN; each of which is hereby incorporated by reference in its entirety. Various viruses, viral antigens, and viral antigen epitopes that can be used in the embodiments described herein are disclosed in U.S. Patent Application No. 20020007173A1 (now U.S. Pat. No. 6,977,074). In some aspects, one or more, including any combination of the listed viruses, viral antigens, or viral epitopes can be specifically included or excluded from the an embodiment of a method.

Other relevant disclosures are present in U.S. patent application Ser. No. 11/156,369 (Pub. No. 2006-0057673 A1), and U.S. Provisional Patent Application. No. 60/691,889, both filed on. Jun. 17, 2005, both entitled EPITOPE ANALOGS, and each of which is incorporated herein by reference in its entirety. Also relevant are, U.S. Provisional Patent App. Nos. 60/691,579, filed on Jun. 17, 2005, entitled METHODS AND COMPOSITIONS TO ELICIT MULTIVALENT IMMUNE RESPONSES AGAINST DOMINANT AND SUBDOMINANT EPITOPES, EXPRESSED ON CANCER CELLS AND TUMOR STROMA, 60/691,581, filed on Jun. 17, 2005, entitled MULTIVALENT ENTRAIN-AND-AMPLIFY IMMUNOTHERAPEUTICS FOR CARCINOMA, and U.S. patent application Ser. No. 11/155,288 (Pub. No 2006-0008468 A1), filed Jun. 17, 2005, entitled COMBINATIONS OF TUMOR-ASSOCIATED ANTIGENS IN DIAGNOSTICS FOR VARIOUS TYPES OF CANCERS, each of which is incorporated herein by reference in its entirety.

Induction with an agent such as non-replicating recombinant DNA (plasmid) can have, and have shown, an impact on the subsequent doses, enabling robust amplification of immunity to epitopes expressed by the recombinant DNA and peptide, and entraining its cytolytic nature. In fact, when single or multiple administrations of recombinant DNA vector or peptide separately achieved modest immune or no responses, inducing with DNA and amplifying with peptide achieved substantially higher responses, both as a rate of responders and as a magnitude of response. As shown in U.S. patent application Ser. Nos. 10/871,707, filed on Jun. 17, 2004, entitled METHODS TO ELICIT, ENHANCE AND SUSTAIN IMMUNE RESPONSES AGAINST MHC CLASS I-RESTRICTED EPITOPES; FOR PROPHYLACTIC OR THERAPEUTIC PURPOSES, (Publication No. 2005-0079152-A1); 60/640,727, filed Dec. 29, 2004, entitled METHODS TO TRIGGER, MAINTAIN AND MANIPULATE IMMUNE RESPONSES BY TARGETED ADMINISTRATION OF BIOLOGICAL RESPONSE MODIFIERS INTO LYMPHOID ORGANS; Ser. No. 11/323,572 cited above; and WO05002621 (each of which is incorporated herein by reference in its entirety) the rate of response was at least doubled and the magnitude of response (mean and median) was at least tripled by using a recombinant DNA induction/peptide-amplification protocol. Thus, preferred protocols result in induction of immunity (Tc1 immunity) that is able to deal with antigenic cells in vivo, within lymphoid and non-lymphoid organs.

Such induce-and-amplify protocols involving specific sequences of recombinant DNA entrainment doses, followed by peptide boosts administered to lymphoid organs, are thus useful for the purpose of induction, amplification and maintenance of strong T cell responses, for example for prophylaxis or therapy of infectious diseases Target diseases can include those caused by prions, for example. Exemplary diseases, organisms and antigens and epitopes associated with target organisms, cells and diseases are described in U.S. application Ser. No. 09/776,232 (filed on Feb. 2, 2001; Pub. No. 20020007173 A1) entitled METHODS OF INDUCING A CTL RESPONSE. Among the infectious diseases that can be addressed are those caused by agents that tend to establish chronic infections (HIV, herpes simplex virus, CMV, Hepatitis B and C viruses, papilloma virus and the like) and/or those that are connected with acute infections (for example, influenza virus, measles, RSV, Ebola virus). All these infectious agents have defined or definable antigens that can be used as basis for designing compositions such as peptide epitopes.

Practice of various of the methodological embodiments can require use of at least two different compositions and, especially when there is more than a single target antigen, can involve several compositions to be administered together and/or at different times. Thus, some embodiments can relate to sets and subsets of immunogenic compositions and individual doses thereof. Multivalency can be achieved using compositions that include multivalent immunogens, combinations of monovalent immunogens, coordinated use of compositions that include a monovalent immunogen or various combinations thereof. Multiple compositions, manufactured for use in a particular treatment regimen or protocol according to such methods, can define an immunotherapeutic product. In some embodiments all or a subset of the compositions of the product can be packaged together in a kit. In some instances the inducing and amplifying compositions targeting a single epitope, or set of epitopes, can be packaged together. In other instances multiple inducing compositions can be assembled in one kit and the corresponding amplifying compositions assembled in another kit. Alternatively compositions may be packaged and sold individually along with instructions, in printed form or on machine-readable media, describing how they can be used in conjunction with each other to achieve the beneficial results of the methods. Further variations will be apparent to one of skill in the art. The use of various packaging schemes comprising less than all of the compositions that might be used in a particular protocol or regimen facilitates the personalization of the treatment, for example based on observed response to the immunotherapeutic or its various components, as described in Provisional U.S. Patent Application No. 60/580,964, and U.S. patent application Ser. No. 11/155,928 both entitled IMPROVED EFFICACY OF ACTIVE IMMUNOTHERAPY BY INTEGRATING DIAGNOSTIC WITH THERAPEUTIC METHODS, each of which is incorporated by reference in its entirety.

Embodiments are directed to methods, uses, therapies and compositions related to epitopes and compositions with specificity for MHC, including, for example, those listed in Tables 1-4. Other embodiments include one or more of the MHCs listed in Tables 1-4, including combinations of the same, while other embodiments specifically exclude any one or more of the MHCs or combinations thereof. Tables 3-4 include frequencies for the listed HLA antigens.

TABLE 1

Class I MHC Molecules
Class I

*Human*

HLA-A1
HLA-A*0101
HLA-A*0201
HLA-A*0202
HLA-A*0203
HLA-A*0204
HLA-A*0205
HLA-A*0206
HLA-A*0207
HLA-A*0209
HLA-A*0214
HLA-A3
HLA-A*0301
HLA-A*1101
HLA-A23
HLA-A24
HLA-A25
HLA-A*2902
HLA-A*3101
HLA-A*3302
HLA-A*6801
HLA-A*6901
HLA-B7
HLA-B*0702
HLA-B*0703
HLA-B*0704
HLA-B*0705
HLA-B8
HLA-B13
HLA-B14
HLA-B*1501 (B62)
HLA-B17
HLA-B18
HLA-B22
HLA-B27
HLA-B*2702
HLA-B*2704
HLA-B*2705
HLA-B*2709
HLA-B35
HLA-B*3501
HLA-B*3502
HLA-B*3701
HLA-B*3801
HLA-B*39011
HLA-B*3902
HLA-B40
HLA-B*40012 (B60)
HLA-B*4006 (B61)
HLA-B44
HLA-B*4402
HLA-B*4403
HLA-B*4501
HLA-B*4601
HLA-B51
HLA-B*5101
HLA-B*5102
HLA-B*5103
HLA-B*5201
HLA-B*5301
HLA-B*5401
HLA-B*5501
HLA-B*5502
HLA-B*5601
HLA-B*5801
HLA-B*6701
HLA-B*7301
HLA-B*7801
HLA-Cw*0102
HLA-Cw*0301
HLA-Cw*0304

TABLE 1-continued

Class I MHC Molecules
Class I

HLA-Cw*0401
HLA-Cw*0601
HLA-Cw*0602
HLA-Cw*0702
HLA-Cw8
HLA-Cw*1601 M
HLA-G

*Murine*

H2-K$^d$
H2-D$^d$
H2-L$^d$
H2-K$^b$
H2-D$^b$
H2-K$^k$
H2-K$^{kml}$
Qa-1$^a$
Qa-2
H2-M3

*Rat*

RT1.A$^a$
RT1.A$^l$

*Bovine*

Bota-A11
Bota-A20

*Chicken*

B-F4
B-F12
B-F15
B-F19

*Chimpanzee*

Patr-A*04
Patr-A*11
Patr-B*01
Patr-B*13
Patr-B*16

*Baboon*

Papa-A*06

*Macaque*

Mamu-A*01

*Swine*

SLA (haplotype d/d)

*Virus homolog* hCMV class I homolog UL18

TABLE 2

Class I MHC Molecules
Class I

*Human*

HLA-A1
HLA-A*0101
HLA-A*0201
HLA-A*0202
HLA-A*0204
HLA-A*0205
HLA-A*0206
HLA-A*0207
HLA-A*0214
HLA-A3
HLA-A*1101
HLA-A24
HLA-A*2902
HLA-A*3101

TABLE 2-continued

Class I MHC Molecules
Class I

HLA-A*3302
HLA-A*6801
HLA-A*6901
HLA-B7
HLA-B*0702
HLA-B*0703
HLA-B*0704
HLA-B*0705
HLA-B8
HLA-B14
HLA-B*1501 (B62)
HLA-B27
HLA-B*2702
HLA-B*2705
HLA-B35
HLA-B*3501
HLA-B*3502
HLA-B*3701
HLA-B*3801
HLA-B*39011
HLA-B*3902
HLA-B40
HLA-B*40012 (B60)
HLA-B*4006 (B61)
HLA-B44
HLA-B*4402
HLA-B*4403
HLA-B*4601
HLA-B51
HLA-B*5101
HLA-B*5102
HLA-B*5103
HLA-B*5201
HLA-B*5301
HLA-B*5401
HLA-B*5501
HLA-B*5502
HLA-B*5601
HLA-B*5801
HLA-B*6701
HLA-B*7301
HLA-B*7801
HLA-Cw*0102
HLA-Cw*0301
HLA-Cw*0304
HLA-Cw*0401
HLA-Cw*0601
HLA-Cw*0602
HLA-Cw*0702
HLA-G

Murine $H2-K^d$
$H2-D^d$
$H2-L^d$
$H2-K^b$
$H2-D^b$
$H2-K^k$
$H2-K^{kml}$
Qa-2

Rat $RT1.A^a$
$RT1.A^l$

Bovine

Bota-A11
Bota-A20

Chicken

B-F4
B-F12
B-F15
B-F19

Virus homolog hCMV class I homolog UL18

TABLE 3

Estimated gene frequencies of HLA-A antigens

| Antigen | CAU Gf[a] | CAU SE[b] | AFR Gf | AFR SE | ASI Gf | ASI SE | LAT Gf | LAT SE | NAT Gf | NAT SE |
|---|---|---|---|---|---|---|---|---|---|---|
| A1 | 15.1843 | 0.0489 | 5.7256 | 0.0771 | 4.4818 | 0.0846 | 7.4007 | 0.0978 | 12.0316 | 0.2533 |
| A2 | 28.6535 | 0.0619 | 18.8849 | 0.1317 | 24.6352 | 0.1794 | 28.1198 | 0.1700 | 29.3408 | 0.3585 |
| A3 | 13.3890 | 0.0463 | 8.4406 | 0.0925 | 2.6454 | 0.0655 | 8.0789 | 0.1019 | 11.0293 | 0.2437 |
| A28 | 4.4652 | 0.0280 | 9.9269 | 0.0997 | 1.7657 | 0.0537 | 8.9446 | 0.1067 | 5.3856 | 0.1750 |
| A36 | 0.0221 | 0.0020 | 1.8836 | 0.0448 | 0.0148 | 0.0049 | 0.1584 | 0.0148 | 0.1545 | 0.0303 |
| A23 | 1.8287 | 0.0181 | 10.2086 | 0.1010 | 0.3256 | 0.0231 | 2.9269 | 0.0628 | 1.9903 | 0.1080 |
| A24 | 9.3251 | 0.0395 | 2.9668 | 0.0560 | 22.0391 | 0.1722 | 13.2610 | 0.1271 | 12.6613 | 0.2590 |
| A9 unsplit | 0.0809 | 0.0038 | 0.0367 | 0.0063 | 0.0858 | 0.0119 | 0.0537 | 0.0086 | 0.0356 | 0.0145 |
| A9 total | 11.2347 | 0.0429 | 13.2121 | 0.1128 | 22.4505 | 0.1733 | 16.2416 | 0.1382 | 14.6872 | 0.2756 |
| A25 | 2.1157 | 0.0195 | 0.4329 | 0.0216 | 0.0990 | 0.0128 | 1.1937 | 0.0404 | 1.4520 | 0.0924 |
| A26 | 3.8795 | 0.0262 | 2.8284 | 0.0547 | 4.6628 | 0.0862 | 3.2612 | 0.0662 | 2.4292 | 0.1191 |
| A34 | 0.1508 | 0.0052 | 3.5228 | 0.0610 | 1.3529 | 0.0470 | 0.4928 | 0.0260 | 0.3150 | 0.0432 |
| A43 | 0.0018 | 0.0006 | 0.0334 | 0.0060 | 0.0231 | 0.0062 | 0.0055 | 0.0028 | 0.0059 | 0.0059 |
| A66 | 0.0173 | 0.0018 | 0.2233 | 0.0155 | 0.0478 | 0.0089 | 0.0399 | 0.0074 | 0.0534 | 0.0178 |
| A10 unsplit | 0.0790 | 0.0038 | 0.0939 | 0.0101 | 0.1255 | 0.0144 | 0.0647 | 0.0094 | 0.0298 | 0.0133 |
| A10 total | 6.2441 | 0.0328 | 7.1348 | 0.0850 | 6.3111 | 0.0993 | 5.0578 | 0.0816 | 4.2853 | 0.1565 |
| A29 | 3.5796 | 0.0252 | 3.2071 | 0.0582 | 1.1233 | 0.0429 | 4.5156 | 0.0774 | 3.4345 | 0.1410 |
| A30 | 2.5067 | 0.0212 | 13.0969 | 0.1129 | 2.2025 | 0.0598 | 4.4873 | 0.0772 | 2.5314 | 0.1215 |
| A31 | 2.7386 | 0.0221 | 1.6556 | 0.0420 | 3.6005 | 0.0761 | 4.8328 | 0.0800 | 6.0881 | 0.1855 |
| A32 | 3.6956 | 0.0256 | 1.5384 | 0.0405 | 1.0331 | 0.0411 | 2.7064 | 0.0604 | 2.5521 | 0.1220 |
| A33 | 1.2080 | 0.0148 | 6.5607 | 0.0822 | 9.2701 | 0.1191 | 2.6593 | 0.0599 | 1.0754 | 0.0796 |

TABLE 3-continued

Estimated gene frequencies of HLA-A antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| A74 | 0.0277 | 0.0022 | 1.9949 | 0.0461 | 0.0561 | 0.0096 | 0.2027 | 0.0167 | 0.1068 | 0.0252 |
| A19 unsplit | 0.0567 | 0.0032 | 0.2057 | 0.0149 | 0.0990 | 0.0128 | 0.1211 | 0.0129 | 0.0475 | 0.0168 |
| A19 total | 13.8129 | 0.0468 | 28.2593 | 0.1504 | 17.3846 | 0.1555 | 19.5252 | 0.1481 | 15.8358 | 0.2832 |
| AX | 0.8204 | 0.0297 | 4.9506 | 0.0963 | 2.9916 | 0.1177 | 1.6332 | 0.0878 | 1.8454 | 0.1925 |

[a]Gene frequency.
[b]Standard error.

TABLE 4

Estimated gene frequencies for HLA-B antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| B7 | 12.1782 | 0.0445 | 10.5960 | 0.1024 | 4.2691 | 0.0827 | 6.4477 | 0.0918 | 10.9845 | 0.2432 |
| B8 | 9.4077 | 0.0397 | 3.8315 | 0.0634 | 1.3322 | 0.0467 | 3.8225 | 0.0715 | 8.5789 | 0.2176 |
| B13 | 2.3061 | 0.0203 | 0.8103 | 0.0295 | 4.9222 | 0.0886 | 1.2699 | 0.0416 | 1.7495 | 0.1013 |
| B14 | 4.3481 | 0.0277 | 3.0331 | 0.0566 | 0.5004 | 0.0287 | 5.4166 | 0.0846 | 2.9823 | 0.1316 |
| B18 | 4.7980 | 0.0290 | 3.2057 | 0.0582 | 1.1246 | 0.0429 | 4.2349 | 0.0752 | 3.3422 | 0.1391 |
| B27 | 4.3831 | 0.0278 | 1.2918 | 0.0372 | 2.2355 | 0.0603 | 2.3724 | 0.0567 | 5.1970 | 0.1721 |
| B35 | 9.6614 | 0.0402 | 8.5172 | 0.0927 | 8.1203 | 0.1122 | 14.6516 | 0.1329 | 10.1198 | 0.2345 |
| B37 | 1.4032 | 0.0159 | 0.5916 | 0.0252 | 1.2327 | 0.0449 | 0.7807 | 0.0327 | 0.9755 | 0.0759 |
| B41 | 0.9211 | 0.0129 | 0.8183 | 0.0296 | 0.1303 | 0.0147 | 1.2818 | 0.0418 | 0.4766 | 0.0531 |
| B42 | 0.0608 | 0.0033 | 5.6991 | 0.0768 | 0.0841 | 0.0118 | 0.5866 | 0.0284 | 0.2856 | 0.0411 |
| B46 | 0.0099 | 0.0013 | 0.0151 | 0.0040 | 4.9292 | 0.0886 | 0.0234 | 0.0057 | 0.0238 | 0.0119 |
| B47 | 0.2069 | 0.0061 | 0.1305 | 0.0119 | 0.0956 | 0.0126 | 0.1832 | 0.0159 | 0.2139 | 0.0356 |
| B48 | 0.0865 | 0.0040 | 0.1316 | 0.0119 | 2.0276 | 0.0575 | 1.5915 | 0.0466 | 1.0267 | 0.0778 |
| B53 | 0.4620 | 0.0092 | 10.9529 | 0.1039 | 0.4315 | 0.0266 | 1.6982 | 0.0481 | 1.0804 | 0.0798 |
| B59 | 0.0020 | 0.0006 | 0.0032 | 0.0019 | 0.4277 | 0.0265 | 0.0055 | 0.0028 | 0[c] | — |
| B67 | 0.0040 | 0.0009 | 0.0086 | 0.0030 | 0.2276 | 0.0194 | 0.0055 | 0.0028 | 0.0059 | 0.0059 |
| B70 | 0.3270 | 0.0077 | 7.3571 | 0.0866 | 0.8901 | 0.0382 | 1.9266 | 0.0512 | 0.6901 | 0.0639 |
| B73 | 0.0108 | 0.0014 | 0.0032 | 0.0019 | 0.0132 | 0.0047 | 0.0261 | 0.0060 | 0[c] | — |
| B51 | 5.4215 | 0.0307 | 2.5980 | 0.0525 | 7.4751 | 0.1080 | 6.8147 | 0.0943 | 6.9077 | 0.1968 |
| B52 | 0.9658 | 0.0132 | 1.3712 | 0.0383 | 3.5121 | 0.0752 | 2.2447 | 0.0552 | 0.6960 | 0.0641 |
| B5 unsplit | 0.1565 | 0.0053 | 0.1522 | 0.0128 | 0.1288 | 0.0146 | 0.1546 | 0.0146 | 0.1307 | 0.0278 |
| B5 total | 6.5438 | 0.0435 | 4.1214 | 0.0747 | 11.1160 | 0.1504 | 9.2141 | 0.1324 | 7.7344 | 0.2784 |
| B44 | 13.4838 | 0.0465 | 7.0137 | 0.0847 | 5.6807 | 0.0948 | 9.9253 | 0.1121 | 11.8024 | 0.2511 |
| B45 | 0.5771 | 0.0102 | 4.8069 | 0.0708 | 0.1816 | 0.0173 | 1.8812 | 0.0506 | 0.7603 | 0.0670 |
| B12 unsplit | 0.0788 | 0.0038 | 0.0280 | 0.0055 | 0.0049 | 0.0029 | 0.0193 | 0.0051 | 0.0654 | 0.0197 |
| B12 total | 14.1440 | 0.0474 | 11.8486 | 0.1072 | 5.8673 | 0.0963 | 11.8258 | 0.1210 | 12.6281 | 0.2584 |
| B62 | 5.9117 | 0.0320 | 1.5267 | 0.0404 | 9.2249 | 0.1190 | 4.1825 | 0.0747 | 6.9421 | 0.1973 |
| B63 | 0.4302 | 0.0088 | 1.8865 | 0.0448 | 0.4438 | 0.0270 | 0.8083 | 0.0333 | 0.3738 | 0.0471 |
| B75 | 0.0104 | 0.0014 | 0.0226 | 0.0049 | 1.9673 | 0.0566 | 0.1101 | 0.0123 | 0.0356 | 0.0145 |
| B76 | 0.0026 | 0.0007 | 0.0065 | 0.0026 | 0.0874 | 0.0120 | 0.0055 | 0.0028 | 0 | — |
| B77 | 0.0057 | 0.0010 | 0.0119 | 0.0036 | 0.0577 | 0.0098 | 0.0083 | 0.0034 | 0[c] | 0.0059 |
| B15 unsplit | 0.1305 | 0.0049 | 0.0691 | 0.0086 | 0.4301 | 0.0266 | 0.1820 | 0.0158 | 0.0059 | 0.0206 |
| B15 total | 6.4910 | 0.0334 | 3.5232 | 0.0608 | 12.2112 | 0.1344 | 5.2967 | 0.0835 | 0.0715 7.4290 | 0.2035 |
| B38 | 2.4413 | 0.0209 | 0.3323 | 0.0189 | 3.2818 | 0.0728 | 1.9652 | 0.0517 | 1.1017 | 0.0806 |
| B39 | 1.9614 | 0.0188 | 1.2893 | 0.0371 | 2.0352 | 0.0576 | 6.3040 | 0.0909 | 4.5527 | 0.1615 |
| B16 unsplit | 0.0638 | 0.0034 | 0.0237 | 0.0051 | 0.0644 | 0.0103 | 0.1226 | 0.0130 | 0.0593 | 0.0188 |
| B16 total | 4.4667 | 0.0280 | 1.6453 | 0.0419 | 5.3814 | 0.0921 | 8.3917 | 0.1036 | 5.7137 | 0.1797 |
| B57 | 3.5955 | 0.0252 | 5.6746 | 0.0766 | 2.5782 | 0.0647 | 2.1800 | 0.0544 | 2.7265 | 0.1260 |
| B58 | 0.7152 | 0.0114 | 5.9546 | 0.0784 | 4.0189 | 0.0803 | 1.2481 | 0.0413 | 0.9398 | 0.0745 |
| B17 unsplit | 0.2845 | 0.0072 | 0.3248 | 0.0187 | 0.3751 | 0.0248 | 0.1446 | 0.0141 | 0.2674 | 0.0398 |
| B17 total | 4.5952 | 0.0284 | 11.9540 | 0.1076 | 6.9722 | 0.1041 | 3.5727 | 0.0691 | 3.9338 | 0.1503 |
| B49 | 1.6452 | 0.0172 | 2.6286 | 0.0528 | 0.2440 | 0.0200 | 2.3353 | 0.0562 | 1.5462 | 0.0953 |
| B50 | 1.0580 | 0.0138 | 0.8636 | 0.0304 | 0.4421 | 0.0270 | 1.8883 | 0.0507 | 0.7862 | 0.0681 |
| B21 unsplit | 0.0702 | 0.0036 | 0.0270 | 0.0054 | 0.0132 | 0.0047 | 0.0771 | 0.0103 | 0.0356 | 0.0145 |
| B21 total | 2.7733 | 0.0222 | 3.5192 | 0.0608 | 0.6993 | 0.0339 | 4.3007 | 0.0755 | 2.3680 | 0.1174 |
| B54 | 0.0124 | 0.0015 | 0.0183 | 0.0044 | 2.6873 | 0.0660 | 0.0289 | 0.0063 | 0.0534 | 0.0178 |
| B55 | 1.9046 | 0.0185 | 0.4895 | 0.0229 | 2.2444 | 0.0604 | 0.9515 | 0.0361 | 1.4054 | 0.0909 |

TABLE 4-continued

Estimated gene frequencies for HLA-B antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| B56 | 0.5527 | 0.0100 | 0.2686 | 0.0170 | 0.8260 | 0.0368 | 0.3596 | 0.0222 | 0.3387 | 0.0448 |
| B22 unsplit | 0.1682 | 0.0055 | 0.0496 | 0.0073 | 0.2730 | 0.0212 | 0.0372 | 0.0071 | 0.1246 | 0.0272 |
| B22 total | 2.0852 | 0.0217 | 0.8261 | 0.0297 | 6.0307 | 0.0971 | 1.3771 | 0.0433 | 1.9221 | 0.1060 |
| B60 | 5.2222 | 0.0302 | 1.5299 | 0.0404 | 8.3254 | 0.1135 | 2.2538 | 0.0553 | 5.7218 | 0.1801 |
| B61 | 1.1916 | 0.0147 | 0.4709 | 0.0225 | 6.2072 | 0.0989 | 4.6691 | 0.0788 | 2.6023 | 0.1231 |
| B40 unsplit | 0.2696 | 0.0070 | 0.0388 | 0.0065 | 0.3205 | 0.0230 | 0.2473 | 0.0184 | 0.2271 | 0.0367 |
| B40 total | 6.6834 | 0.0338 | 2.0396 | 0.0465 | 14.8531 | 0.1462 | 7.1702 | 0.0963 | 8.5512 | 0.2168 |
| BX | 1.0922 | 0.0252 | 3.5258 | 0.0802 | 3.8749 | 0.0988 | 2.5266 | 0.0807 | 1.9867 | 0.1634 |

[a]Gene frequency.
[b]Standard error.
[c]The observed gene count was zero.

Some embodiments relate to methods, uses, therapies, kits, products and compositions related to generating immune responses against diseases, such as viral diseases and other microbial diseases, including without limitation the microbes and viruses listed in Tables 5-7. Furthermore, some embodiments relate to or can utilize antigens from various animals, as well as B cell and class I T cell epitopes from the antigens. Without being limited thereto, examples of some antigens and epitopes are listed in Tables 5-7 and in the other references cited herein which are incorporated herein by reference in their entirety. It should be understood that in some embodiments, one or more or combinations of the viruses, antigens, and epitopes listed and referenced herein can be specifically excluded, while in some embodiments one or more or combinations thereof can be included. The B cell epitopes and class I T cell epitopes that can be used with the various embodiments are not limited to those that are specifically listed, as additional epitopes can be easily determined by the skilled artisan using any suitable technique. As one example, additional class I T cell epitopes can be identified using a suitable method such as epitopes with binding specificity for any MHC molecule. Any B cell epitope for any microbe or antigen listed here can be easily determined using any suitable technique by one of skill in the art. For example, such epitopes can be identified using homology modeling techniques and using the Bcipep database alone or in combination with predictive techniques. Also, The identification of B cell epitopes which are able to elicit an antibody response can be readily accomplished using techniques well known in the art. See, e.g., Geysen et al. (1984) Proc. Natl. Acad. Sci. USA 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) Molecular Immunology 23:709-715 (technique for identifying peptides with high affinity for a given antibody); each of which is incorporated herein by reference in its entirety.

TABLE 5

| Virus | Protein | AA Position | T cell epitope MHC ligand (Antigen) | MHC molecule |
|---|---|---|---|---|
| EBV | EBNA-3 | 325-333 | AYPLHEQHG (SEQ ID NO:12) | HLA-B8 |
| EBV | EBNA-3 | 158-166 | YIKSFVSDA (SEQ ID NO:13) | HLA-B8 |
| EBV | LMP-2 | 236-244 | RRRWRRLTV (SEQ ID NO:14) | HLA-B*2704 |
| EBV | EBNA-6 | 258-266 | RRIYDLIEL (SEQ ID NO:15) | HLA-B*2705 |
| EBV | EBNA-3 | 458-466 | YPLHEQHGM (SEQ ID NO:16) | HLA-B*3501 |
| EBV | EBNA-3 | 458-466 | YPLHEQHGM (SEQ ID NO:17) | HLA-B*3503 |
| EBV | LMP-2 | 426-434 | CLGGLLTMV (SEQ ID NO:18) | HLA-A*0201 |
| EBV | EBNA-1 | 480-484 | NIAEGLRAL (SEQ ID NO:19) | HLA-A*0201 |
| EBV | EBNA-1 | 519-527 | NLRRGTALA (SEQ ID NO:20) | HLA-A*0201 |

TABLE 5-continued

| Virus | Protein | AA Position | T cell epitope MHC ligand (Antigen) | MHC molecule |
|---|---|---|---|---|
| EBV | EBNA-1 | 525-533 | ALAIPQCRL (SEQ ID NO:21) | HLA-A*0201 |
| EBV | EBNA-1 | 575-582 | VLKDAIKDL (SEQ ID NO:22) | HLA-A*0201 |
| EBV | EBNA-1 | 562-570 | FMVFLQTHI (SEQ ID NO:23) | HLA-A*0201 |
| EBV | EBNA-2 | 15-23 | HLIVDTDSL (SEQ ID NO:24) | HLA-A*0201 |
| EBV | EBNA-2 | 22-30 | SLGNPSLSV (SEQ ID NO:25) | HLA-A*0201 |
| EBV | EBNA-2 | 126-134 | PLASAMRML (SEQ ID NO:26) | HLA-A*0201 |
| EBV | EBNA-2 | 132-140 | RMLWMANYI (SEQ ID NO:27) | HLA-A*0201 |
| EBV | EBNA-2 | 133-141 | MLWMANYIV (SEQ ID NO:28) | HLA-A*0201 |
| EBV | EBNA-2 | 151-159 | ILPQGPQTA (SEQ ID NO:29) | HLA-A*0201 |
| EBV | EBNA-2 | 171-179 | PLRPTAPTI (SEQ ID NO:30) | HLA-A*0201 |
| EBV | EBNA-2 | 205-213 | PLPPATLTV (SEQ IDNO:31) | HLA-A*0201 |
| EBV | EBNA-2 | 246-254 | RMHLPVLHV (SEQ ID NO:32) | HLA-A*0201 |
| EBV | EBNA-2 | 287-295 | PMPLPPSQL (SEQ ID NO:33) | HLA-A*0201 |
| EBV | EBNA-2 | 294-302 | QLPPPAAPA (SEQ ID NO:34) | HLA-A*0201 |
| EBV | EBNA-2 | 381-389 | SMPELSPVL (SEQ ID NO:35) | HLA-A*0201 |
| EBV | EBNA-2 | 453-461 | DLDESWDYI (SEQ ID NO:36) | HLA-A*0201 |
| EBV | BZLF1 | 43-51 | PLPCVLWPV (SEQ ID NO:37) | HLA-A*0201 |
| EBV | BZLF1 | 167-175 | SLEECDSEL (SEQ ID NO:38) | HLA-A*0201 |
| EBV | BZLF1 | 176-184 | EIKRYKNRV (SEQ ID NO:39) | HLA-A*0201 |
| EBV | BZLF1 | 195-203 | QLLQHYREV (SEQ ID NO:40) | HLA-A*0201 |
| EBV | BZLF1 | 196-204 | LLQHYREVA (SEQ ID NO:41) | HLA-A*0201 |
| EBV | BZLFI | 217-225 | LLKQMCPSL (SEQ ID NO:42) | HLA-A*0201 |
| EBV | BZLF1 | 229-237 | SIIPRTPDV (SEQ ID NO:43) | HLA-A*0201 |
| EBV | EBNA-6 | 284-293 | LLDFVRFMGV (SEQ ID NO:44) | HLA-A*0201 |
| EBV | EBNA-3 | 464-472 | SVRDRLARL (SEQ ID NO:45) | HLA-A*0203 |

TABLE 5-continued

| Virus | Protein | AA Position | T cell epitope MHC ligand (Antigen) | MHC molecule |
|---|---|---|---|---|
| EBV | EBNA-4 | 416-424 | IVTDFSVIK (SEQ ID NO:46) | HLA-A*1101 |
| EBV | EBNA-4 | 399-408 | AVFDRKSDAK (SEQ ID NO:47) | HLA-A*0201 |
| EBV | EBNA-3 | 246-253 | RYSIFFDY (SEQ ID NO:48) | HLA-A24 |
| EBV | EBNA-6 | 881-889 | QPRAPIRPI (SEQ ID NO:49) | HLA-B7 |
| EBV | EBNA-3 | 379-387 | RPPIFIRRI. (SEQ ID NO:50) | HLA-B7 |
| EBV | EBNA-1 | 426-434 | EPDVPPGAI (SEQ ID NO:51) | HLA-B7 |
| EBV | EBNA-1 | 228-236 | IPQCRLTPL (SEQ ID NO:52) | HLA-B7 |
| EBV | EBNA-1 | 546-554 | GPGPQPGPL (SEQ ID NO:53) | HLA-B7 |
| EBV | EBNA-1 | 550-558 | QPGPLRESI (SEQ ID NO:54) | HLA-B7 |
| EBV | EBNA-1 | 72-80 | R.PQKRPSCI (SEQ ID NO:55) | HLA-B7 |
| EBV | EBNA-2 | 224-232 | PPTPLLTVL (SEQ ID NO:56) | HLA-B7 |
| EBV | EBNA-2 | 241-249 | TPSPPRMHL (SEQ ID NO:57) | HLA-B7 |
| EBV | EBNA-2 | 244-252 | PPRMHLPVL (SEQ ID NO:58) | HLA-B7 |
| EBV | EBNA-2 | 254-262 | VPDQSMHPL (SEQ ID NO:59) | HLA-B7 |
| EBV | EBNA-2 | 446-454 | PPSIDPADL (SEQ ID NO:60) | HLA-B7 |
| EBV | BZLFI | 44-52 | LPCVLWPVL (SEQ ID NO:61) | HLA-B7 |
| EBV | BZLF1 | 222-231 | CPSLDVDSII (SEQ ID NO:62) | HLA-B7 |
| EBV | BZLFI | 234-242 | TPDVLHEDL (SEQ ID NO:63) | HLA-B7 |
| EBV | EBNA-3 | 339-347 | FLRGRAYGL (SEQ ID NO:64) | HLA-B8 |
| EBV | EBNA-3 | 26-34 | QAKWRLQTL (SEQ ID NO:65) | HLA-B8 |
| HCV | NS3 | 389-397 | HSKKKCDEL (SEQ ID NO:66) | HLA-B8 |
| HCV | env E | 44-51 | ASRCWVAM (SEQ ID NO:67) | HLA-B*3501 |
| HCV | core protein | 27-3 5 | GQIVGGVYL (SEQ ID NO:68) | HLA-B*40012 |
| HCV | NSI | 77-85 | PPLTDFDQGW (SEQ ID NO:69) | HLA-B*5301 |
| HCV | core protein | 18-27 | LMGYIPLVGA (SEQ ID NO:70) | H2-Dd |

TABLE 5-continued

| Virus | Protein | AA Position | T cell epitope MHC ligand (Antigen) | MHC molecule |
|---|---|---|---|---|
| HCV | core protein | 16-25 | ADLMGYIPLV (SEQ ID NO:71) | H2-Dd |
| HCV | NS5 | 409-424 | MSYSWTGALVTPCAEE (SEQ ID NO:72) | H2-Dd |
| HCV | NS1 | 205-213 | KHPDATYSR (SEQ ID NO:73) | Papa-A06 |
| HCV-1 | NSI | 159-167 | TRPPLGNWF (SEQ ID NO:74) | Patr-B13 |
| HCV-1 | NS3 | 351-359 | VPHPNIEEV (SEQ ID NO:75) | Patr-B13 |
| HCV-1 | NS3 | 438-446 | YTGDFDSVI (SEQ ID NO:76) | Patr-B01 |
| HCV-1 | NS4 | 328-335 | SWAIKWEY (SEQ ID NO:77) | Patr-A11 |
| HCV-1 | NSI | 205-213 | KHPDATYSR (SEQ ID NO:78) | Patr-A04 |
| HCV-1 | NS3 | 440-448 | GDFDSVIDC (SEQ ID NO:79) | Patr-A04 |
| HCV-1 | NS3 | 400-409 | KLVALGINAV (SEQ ID NO:80) | HLA-A*0201 |
| HCV-1 | NS3 | 440-448 | GDFDSVIDC (SEQ ID NO:81) | Patr-B16 |
| HCV-1 | env E | 118-126 | GNASRCWVA (SEQ ID NO:82) | Patr-B16 |
| HIV | nef | 117-125 | TQGYFPQWQ (SEQ ID NO:83) | HLA-B*3701 |
| HIV | gagp24 | 143-151 | HQAISPRTI, (SEQ ID NO:84) | HLA-Cw*0301 |
| HIV | gagp24 | 140-151 | QMVHQAISPRTL (SEQ ID NO:85) | HLA-Cw*0301 |
| HIV | gp120 | 431-440 | MYAPPIGGQI (SEQ ID NO:86) | H2-Kd |
| HIV | gp160 | 318-327 | RGPGRAFVTI (SEQ ID NO:87) | H2-Dd |
| HIV | gp120 | 17-29 | MPGRAFVTI (SEQ ID NO:88) | H2-Ld |
| HIV | gp41 | 583-591 | RYLKDQQLL (SEQ ID NO:89) | HLA_A24 |
| HIV | gagp24 | 267-275 | IVGLNKIVR (SEQ ID NO:90) | HLA-A*3302 |
| HIV | gagp24 | 262-270 | EIYKRWIIL (SEQ ID NO:91) | HLA-B8 |
| HIV | gagp24 | 261-269 | GEIYKRWII (SEQ ID NO:92) | HLA-B8 |
| HIV | gagp17 | 93-101 | EIKDTKEAL (SEQ ID NO:93) | HLA-B8 |
| HIV | gp41 | 586-593 | YLKDQQLL (SEQ ID NO:94) | HLA-B8 |
| HIV | gagp24 | 267-277 | ILGLNKIVRMY (SEQ ID NO:95) | HLA-B*1501 |

TABLE 5-continued

| Virus | Protein | AA Position | T cell epitope MHC ligand (Antigen) | MHC molecule |
|---|---|---|---|---|
| HIV | gp41 | 584-592 | ERYLKDQQL (SEQ ID NO:96) | HLA-B14 |
| HIV | nef | 115-125 | YHTQGYFPQWQ (SEQ ID NO:97) | HLA-B17 |
| HIV | nef | 117-128 | TQGYFPQWQNYT (SEQ ID NO:98) | HLA-B17 |
| HIV | gp120 | 314-322 | GRAFVTIGK (SEQ ID NO:99) | HLA-B*2705 |
| HIV | gagp24 | 263-271 | KRWIILGLN (SEQ ID NO:100) | HLA-B*2702 |
| HIV | nef | 72-82 | QVPLRPMTYK (SEQ ID NO:101) | HLA-B*3501 |
| HIV-1 | gagp 17 | 24-31 | GGKKKYKL (SEQ ID NO:102) | HLA-B8 |
| HIV-1 | gp120 | 2-10 | RVKEKYQHL (SEQ ID NO:103) | HLA-B8 |
| HIV-1 | gagp24 | 298-306 | DRFYKTLRA (SEQ ID NO:104) | HLA-B14 |
| HIV-1 | NEF | 132-147 | GVRYPLTFGWCYKLVP (SEQ ID NO:105) | HLA-B18 |
| HIV-1 | gagp24 | 265-24 | KRWIILGLNK (SEQ ID NO:106) | HLA-B*2705 |
| HIV-1 | nef | 190-198 | AFHHVAREL (SEQ ID NO:107) | HLA-B*5201 |
| HIV-1 | RT | 476-484 | ILKEPVHGV (SEQ ID NO:108) | HLA-A*0201 |
| HIV-1 | nef | 190-198 | AFHHVAREL (SEQ ID NO:109) | HLA-A*0201 |
| HIV-1 | gpI60 | 120-128 | KLTPLCVTL (SEQ ID NO:110) | HLA-A*0201 |
| HIV-1 | Gp160 | 814-823 | SLLNATDIAV (SEQ ID NO:111) | HLA-A*0201 |
| HIV-1 | RT | 179-187 | VIYQYMDDL (SEQ ID NO:112) | HLA-A*0201 |
| HIV-1 | gagp 17 | 77-85 | SLYNTVATL (SEQ ID NO:113) | HLA-A*0201 |
| HIV-1 | gp160 | 315-329 | RGPGRAFVTI (SEQ ID NO:114) | HLA-A*0201 |
| HIV-1 | gp41 | 768-778 | RLRDLLLIVTR (SEQ ID NO: 115) | HLA-A3 |
| HIV-1 | nef | 73-82 | QVPLRPMTYK (SEQ ID NO:116) | HLA-A3 |
| HIV-1 | gp120 | 36-45 | TVYYGVPVWK (SEQ ID NO:117) | HLA-A3 |
| HIV-1 | gagp17 | 20-29 | RLRPGGKKK (SEQ ID NO:118) | HLA-A3 |
| HIV-1 | gp120 | 38-46 | VYYGVPVWK (SEQ ID NO:119) | HLA-A3 |
| HIV-1 | nef | 74-82 | VPLRPMTYK (SEQ ID NO:120) | HLA-a*1101 |

TABLE 5-continued

| Virus | Protein | AA Position | T cell epitope MHC ligand (Antigen) | MHC molecule |
|---|---|---|---|---|
| HIV-1 | gagp24 | 325-333 | AIFQSSMTK (SEQ ID NO:121) | HLA-A*1101 |
| HIV-1 | nef | 73-82 | QVPLRPMTYK (SEQ ID NO:122) | HLA-A*1101 |
| HIV-1 | nef | 83-94 | AAVDLSHFLKEK (SEQ ID NO:123) | HLA-A*1101 |
| HIV-1 | gagp24 | 349-359 | ACQGVGGPGGHK (SEQ ID NO:124) | HLA-A*1101 |
| HIV-1 | gagp24 | 203-212 | ETINEEAAEW (SEQ ID NO:125) | HLA-A25 |
| HIV-1 | nef | 128-137 | TPGPGVRYPL (SEQ ID NO:126) | HLA-B7 |
| Mv | HA | 343-351 | DPVIDRLYL (SEQ ID NO:127) | H2-Ld |
| MV | HA | 544-552 | SPGRSFSYF (SEQ ID NO:128) | H2-Ld |
| Pseudorabies virus gp | G111 | 455-463 | IAGIGILAI (SEQ ID NO:129) | HLA-A*0201 |
| Rabiesvirus | NS197-205 | | VEAEIAHQI (SEQ ID NO:130) | H2-Kk |
| RSV | M2 | 82-90 | SYIGSINNI (SEQ ID NO:131) | H2-Kd |
| SIV | gagp11C | 179-190 | EGCTPYDTNQML (SEQ ID NO:132) | Mamu-A*01 |
| EBV | EBNA-6 | 335-343 | KEHVIQNAF (SEQ ID NO:133) | HLA-B44 |
| EBV | EBNA-6 | 130-139 | EENLLDFVRF (SEQ ID NO:134) | HLA-B*4403 |
| EBV | EBNA-2 | 42-51 | DTPLIPLTIF (SEQ ID NO:135) | HLA-B51 |
| EBV | EBNA-6 | 213-222 | QNGALAINTF (SEQ ID NO:136) | HLA-1362 |
| EBV | EBNA-3 | 603-611 | RLRAEAGVK (SEQ ID NO:137) | HLA-A3 |
| HBV | sAg | 348-357 | GLSPTVWLSV (SEQ ID NO:138) | HLA-A*0201 |
| HBV | SAg | 335-343 | WLSLLVPFV (SEQ ID NO:139) | HLA-A*0201 |
| HBV | cAg | 18-27 | FLPSDFFPSV (SEQ ID NO:140) | HLA-A*0201 |
| HBV | cAg | 18-27 | FLPSDFFPSV (SEQ ID NO:141) | HLA-A*0202 |
| HBV | cAg | 18-27 | FLPSDFFPSV (SEQ ID NO:142) | HLA-A*0205 |
| HBV | cAg | 18-27 | FLPSDFFPSV (SEQ ID NO:143) | HLA-A*0206 |
| HBV | pol | 575-583 | FLLSLGIHL (SEQ ID NO:144) | HLA-A*0201 |
| HBV | pol | 816-824 | SLYADSPSV (SEQ ID NO:145) | HLA-A*0201 |

TABLE 5-continued

| Virus | Protein | AA Position | T cell epitope MHC ligand (Antigen) | MHC molecule |
|---|---|---|---|---|
| HBV | pol | 455-463 | GLSRYVARL (SEQ ID NO:146) | HLA-A*0201 |
| HBV | env | 338-347 | LLVPFVQWFV (SEQ ID NO:147) | HLA-A*0201 |
| HBV | pol | 642-650 | ALMPLYACI (SEQ ID NO:148) | HLA-A*0201 |
| HBV | env | 378-387 | LLPIFFCLWV (SEQ ID NO:149) | HLA-A*0201 |
| HBV | pol | 538-546 | YMDDVVLGA (SEQ ID NO:150) | HLA-A*0201 |
| HBV | env | 250-258 | LLLCLIFLL (SEQ ID NO:151) | HLA-A*0201 |
| HBV | env | 260-269 | LLDYQGMLPV (SEQ ID NO:152) | HLA-A*0201 |
| HBV | env | 370-379 | SIVSPFIPLL (SEQ ID NO:153) | HLA-A*0201 |
| HBV | env | 183-191 | FLLTRILTI (SEQ ID NO:154) | HLA-A*0201 |
| HBV | cAg | 88-96 | YVNVNMGLK (SEQ ID NO:155) | HLA-A*1101 |
| HBV | cAg | 141-151 | STLPETTVVRR (SEQ ID NO:156) | HLA-A*3101 |
| HBV | cAg | 141-151 | STLPETTVVRR (SEQ ID NO:157) | HLA-A*6801 |
| HBV | cAg | 18-27 | FLPSDFFPSV (SEQ ID NO:158) | HLA-A*6801 |
| HBV | sAg | 28-39 | IPQSLDSWWTSL SEQ ID NO:159 | H2-Ld |
| HBV | cAg | 93-100 | MGLKFRQL (SEQ ID NO:160) | H2-Kb |
| HBV | preS | 141-149 | STBXQSGXQ (SEQ ID NO:161) | HLA-A-0201 |
| HCMV | gp B | 618-628 | FIAGNSAYEYV (SEQ ID NO:162) | HLA-A*0201 |
| HCMV | E1 | 978-989 | SDEEFAIVAYTL (SEQ ID NO:163) | HLA-B18 |
| HCMV | pp65 | 397-411 | DDVWTSGSDSDEELV (SEQ ID NO:164) | HLA-b35 |
| HCMV | pp65 | 123-131 | IPSINVHHY (SEQ ID NO:165) | HLA-B*3501 |
| HCMV | pp65 | 495-504 | NLVPMVATVO (SEQ ID NO:166) | HLA-A*0201 |
| HCMV | pp65 | 415-429 | RKTPRVTOGGAMAGA (SEQ ID NO:167) | HLA-B7 |
| HCV | MP | 17-25 | DLMGYIPLV (SEQ ID NO:168) | HLA-A*0201 |
| HCV | MP | 63-72 | LLALLSCLTV (SEQ ID NO:169) | HLA-A*0201 |
| HCV | MP | 105-112 | ILHTPGCV (SEQ ID NO:170) | HLA-A*0201 |

TABLE 5-continued

| Virus | Protein | AA Position | T cell epitope MHC ligand (Antigen) | MHC molecule |
|---|---|---|---|---|
| HCV | env E | 66-75 | QLRRHIDLLV (SEQ ID NO:171) | HLA-A*0201 |
| HCV | env E | 88-96 | DLCGSVFLV (SEQ ID NO:172) | HLA-A*0201 |
| HCV | env E | 172-180 | SMVGNWAKV (SEQ ID NO:173) | HLA-A*0201 |
| HCV | NSI | 308-316 | HLIIQNIVDV (SEQ ID NO:174) | HLA-A*0201 |
| HCV | NSI | 340-348 | FLLLADARV (SEQ ID NO:175) | HLA-A*0201 |
| HCV | NS2 | 234-246 | GLRDLAVAVEPVV (SEQ ID NO:176) | HLA-A*0201 |
| HCV | NSI | 18-28 | SLLAPGAKQNV (SEQ ID NO:177) | HLA-A*0201 |
| HCV | NSI | 19-28 | LLAPGAKQNV (SEQ ID NO:178) | HLA-A*0201 |
| HCV | NS4 | 192-201 | LLFNILGGWV (SEQ ID NO:179) | HLA-A*0201 |
| HCV | NS3 | 579-587 | YLVAYQATV (SEQ ID NO:180) | HLA-A*0201 |
| HCV | core protein | 34-43 | YLLPRRGPRL (SEQ ID NO:181) | HLA-A*0201 |
| HCV | MP | 63-72 | LLALLSCLTI (SEQ ID NO:182) | HLA-A*0201 |
| HCV | NS4 | 174-182 | SLMAFTAAV (SEQ ID NO:183) | HLA-A*0201 |
| HCV | NS3 | 67-75 | CINGVCWTV (SEQ ID NO:184) | HLA-A*0201 |
| HCV | NS3 | 163-171 | LLCPAGHAV (SEQ ID NO:185) | HLA-A*0201 |
| HCV | NS5 | 239-247 | ILDSFDPLV (SEQ ID NO:186) | HLA-A*0201 |
| HCV | NS4A | 236-244 | ILAGYGAGV (SEQ ID NO:187) | HLA-A*0201 |
| HCV | NS5 | 714-722 | GLQDCTMLV (SEQ ID NO:188) | HLA-A*0201 |
| HCV | NS3 | 281-290 | TGAPVTYSTY (SEQ ID NO:189) | HLA-A*0201 |
| HCV | NS4A | 149-157 | HMWNFISGI (SEQ ID NO:190) | HLA-A*0201 |
| HCV | NS5 | 575-583 | RVCEKMALY (SEQ ID NO:191) | HLA-A*0201-A3 |
| HCV | NS1 | 238-246 | TINYTIFK (SEQ ID NO:192) | HLA-A*1101 |
| HCV | NS2 | 109-116 | YISWCLWW (SEQ ID NO:193) | HLA-A23 |
| HCV | core protein | 40-48 | GPRLGVRAT (SEQ ID NO:194) | HLA-B7 |
| HIV-1 | gp120 | 380-388 | SFNCGGEFF (SEQ ID NO:195) | HLA-Cw*0401 |

TABLE 5-continued

| Virus | Protein | AA Position | T cell epitope MHC ligand (Antigen) | MHC molecule |
|---|---|---|---|---|
| HIV-1 | RT | 206-214 | TEMEKECKI (SEQ ID NO:196) | H2-Kk |
| HIV-1 | p17 | 18-26 | KIRLRPGGK (SEQ ID NO:197) | HLA-A*0301 |
| HIV-1 | P17 | 20-29 | RLRPGGKKKY (SEQ ID NO:198) | HLA-A*0301 |
| HIV-I | RT | 325-333 | AIFQSSMTK (SEQ ID NO:199) | HLA-A*0301 |
| HIV-1 | p17 | 84-92 | TLYCVHQRI (SEQ ID NO:200) | HLA-A11 |
| HIV-1 | RT | 508-517 | IYQEPFKNLK (SEQ ID NO:201) | HLA-A11 |
| HIV-1 | p17 | 28-36 | KYKLKHIVW (SEQ ID NO:202) | HLA-A24 |
| HIV-1 | gp120 | 53-62 | LFCASDAKAY (SEQ ID NO:203) | HLA-A24 |
| HIV-1 | gagp24 | 145-155 | QAISPRTLNAW (SEQ ID NO:204) | HLA-A25 |
| HIV-1 | gagp24 | 167-175 | EVIPMFSAL (SEQ ID NO:205) | HLA-A26 |
| HIV-1 | RT | 593-603 | ETFYVDGAANR (SEQ ID NO:206) | HLA-A26 |
| HIV-1 | gp41 | 775-785 | RLRDLLLIVTR (SEQ ID NO:207) | HLA-A31 |
| HIV-1 | RT | 559-568 | PIQKETWETW (SEQ ID NO:208) | HLA-A32 |
| HIV-1 | gp120 | 419-427 | RIKQIINMW (SEQ ID NO:209) | HLA-A32 |
| HIV-1 | RT | 71-79 | ITLWQRPLV (SEQ ID NO:210) | HLA-A*6802 |
| HIV-1 | RT | 85-93 | DTVLEEMNL (SEQ ID NO:211) | HLA-A*6802 |
| HIV-1 | RT | 71-79 | ITLWQRPLV (SEQ ID NO:212) | HLA-A*7401 |
| HIV-1 | gagp24 | 148-156 | SPRTLNAWV (SEQ ID NO:213) | HLA-B7 |
| HIV-1 | gagp24 | 179-187 | ATPQDLNTM (SEQ ID NO:214) | HLA-B7 |
| HIV-1 | gp120 | 303-312 | RPNNNTRKSI (SEQ ID NO:215) | HLA-B7 |
| HIV-1 | gp41 | 843-851 | IPRRIRQGL (SEQ ID NO:216) | HLA-B7 |
| HIV-1 | p17 | 74-82 | ELRSLYNTV (SEQ ID NO:217) | HLA-B8 |
| HIV-1 | nef | 13-20 | WPTVRERM (SEQ ID NO:218) | HLA-B8 |
| HIV-1 | nef | 90-97 | FLKEKGGL (SEQ ID NO:219) | HLA-B8 |
| HIV-1 | gagp24 | 183-191 | DLNTMLNTV (SEQ ID NO:220) | HLA-B14 |

TABLE 5-continued

| Virus | Protein | AA Position | T cell epitope MHC ligand (Antigen) | MHC molecule |
|---|---|---|---|---|
| HIV-1 | P17 | 18-27 | KIRLRPGGKK (SEQ ID NO:221) | HLA-B27 |
| HIV-1 | p17 | 19-27 | IRLRPGGKK (SEQ ID NO:222) | HLA-B27 |
| HIV-1 | gp41 | 791-799 | GRRGWEALKY (SEQ ID NO:223) | HLA-B27 |
| HIV-1 | nef | 73-82 | QVPLRPMTYK (SEQ ID NO:224) | HLA-B27 |
| HIV-1 | GP41 | 590-597 | RYLKDQQL (SEQ ID NO:225) | HLA-B27 |
| HIV-1 | nef | 105-114 | RRQDILDLWI (SEQ ID NO:226) | HLA-B*2705 |
| HIV-1 | nef | 134-141 | RYPLTFGW (SEQ ID NO:227) | HLA-B*2705 |
| HIV-1 | p17 | 36-44 | WASRELERF (SEQ ID NO:228) | HLA-B35 |
| HIV-1 | GAG P24 | 262-270 | TVLDVGDAY (SEQ ID NO:229) | HLA-B35 |
| HIV-1 | gp120 | 42-52 | VPVWKEATTTL (SEQ ID NO:230) | HLA-B35 |
| HIV-1 | P17 | 36-44 | NSSKVSQNY (SEQ ID NO:231) | HLA-B35 |
| HIV-1 | gagp24 | 254-262 | PPIPVGDIY (SEQ ID NO:232) | HLA-B35 |
| HIV-1 | RT | 342-350 | HPDIVIYQY (SEQ ID NO:233) | HLA-B35 |
| HIV-1 | gp41 | 611-619 | TAVPWNASW (SEQ ID NO:234) | HLA-B35 |
| HIV-1 | gag | 245-253 | NPVPVGNIY (SEQ ID NO:235) | HLA-B35 |
| HIV-1 | nef | 120-128 | YFPDWQNYT (SEQ ID NO:236) | HLA-B37 |
| HIV-1 | gagp24 | 193-201 | GHQAAMQML (SEQ ID NO:237) | HLA-B42 |
| HIV-1 | p17 | 20-29 | RLRPGGKKKY (SEQ ID NO:238) | HLA-B42 |
| HIV-1 | RT | 438-446 | YPGIKVRQL (SEQ ID NO:239) | HLA-B42 |
| HIV-1 | RT | 591-600 | GAETFYVDGA SEQ ID NO:240 | HLA-B45 |
| HIV-1 | gag p24 | 325-333 | NANPDCKTI (SEQ ID NO:241) | HLA-B51 |
| HIV-1 | gag p24 | 275-282 | RMYSPTSI (SEQ ID NO:242) | HLA-B52 |
| HIV-1 | gp120 | 42-51 | VPVWKEATTT (SEQ ID NO:243) | HLA-B*5501 |
| HIV-1 | gag p24 | 147-155 | ISPRTLNAW (SEQ ID NO:244) | HLA-B57 |
| HIV-1 | gag p24 | 240-249 | TSTLQEQIGW (SEQ ID NO:245) | HLA-B57 |

TABLE 5-continued

| Virus | Protein | AA Position | T cell epitope MHC ligand (Antigen) | MHC molecule |
|---|---|---|---|---|
| HIV-1 | gag p24 | 162-172 | KAFSPEVIPMF (SEQ ID NO:246) | HLA-B57 |
| HIV-1 | gag p24 | 311-319 | QASQEVKNW (SEQ ID NO:247) | HLA-B57 |
| HIV-1 | gagp24 | 311-319 | QASQDVKNW (SEQ ID NO:248) | HLA-B57 |
| HIV-1 | nef | 116-125 | HTQGYFPDWQ (SEQ ID NO:249) | HLA-B57 |
| HIV-1 | nef | 120-128 | YFPDWQNYT (SEQ ID NO:250) | HLA-B57 |
| HIV-1 | gag p24 | 240-249 | TSTLQEQIGW (SEQ ID NO:251) | HLA-B58 |
| HIV-1 | p17 | 20-29 | RLRPGGKKKY (SEQ ID NO:252) | HLA-B62 |
| HIV-1 | p24 | 268-277 | LGLNKJVRMY (SEQ ID NO:253) | HLA-B62 |
| HIV-1 | RT | 415-426 | LVGKLNWASQIY (SEQ ID NO:254) | HLA-B62 |
| HIV-1 | RT | 476-485 | ILKEPVHGVY (SEQ ID NO:255) | HLA-B62 |
| HIV-1 | nef | 117-127 | TQGYFPDWQNY (SEQ ID NO:256) | HLA-B62 |
| HIV-1 | nef | 84-91 | AVDLSHFL (SEQ ID NO:257) | HLA-B62 |
| HIV-1 | gag p24 | 168-175 | VIPMFSAL SEQ ID NO:258 | HLA-Cw-0102 |
| HIV-1 | gp120 | 376-384 | FNCGGEFFY (SEQ ID NO:259) | HLA-A29 |
| HIV-1 | gp120 | 375-383 | SFNCGGEFF (SEQ ID NO:260) | HLA-B15 |
| HIV-1 | nef | 136-145 | PLTFGWCYKL (SEQ ID NO:261) | HLA-A*0201 |
| HIV-1 | nef | 180-189 | VLEWRFDSRL (SEQ ID NO:262) | HLA-A*0201 |
| HIV-1 | nef | 68-77 | FPVTPQVPLR (SEQ ID NO:263) | HLA-B7 |
| HIV-1 | nef | 128-137 | TPGPGVRYPL (SEQ ID NO:264) | HLA-B7 |
| HIV-1 | gag p24 | 308-316 | QASQEVKNW (SEQ ID NO:265) | HLA-Cw*0401 |
| HIV-1 IIIB | RT273-282 | | VPLDEDFRKY (SEQ ID NO:266) | HLA-B35 |
| HIV-1 IIIB | RT | 25-33 | NPDIVIYQY (SEQ ID NO:267) | HLA-B35 |
| HIV-1 IIIB | gp41 | 557-565 | RAIEAQAHL (SEQ ID NO:268) | HLA-B51 |
| HLV-1 IIIB | RT | 231-238 | TAFTIPSI (SEQ ID NO:269) | HLA-B51 |
| HIV-I IIIB | p24 | 215-223 | VHPVHAGPIA (SEQ ID NO:270) | HLA-B*5501 |

TABLE 5-continued

| Virus | Protein | AA Position | T cell epitope MHC ligand (Antigen) | MHC molecule |
|---|---|---|---|---|
| HIV-1 IIIB | gp120 | 156-165 | NCSFNISTSI (SEQ ID NO:271) | HLA-Cw8 |
| HIV-I IIIB | gp120 | 241-249 | CTNVSTVQC (SEQ ID NO:272) | HLA-Cw8 |
| HIV-1 5F2 | gp120 | 312-320 | IGPGRAFHT (SEQ ID NO:273) | H2-Dd |
| HIV-1 5F2 | pol | 25-33 | NPDIVIYQY (SEQ ID NO:274) | HLA-B*3501 |
| HIV-1 5F2 | pol | 432-441 | EPIVGAETF (SEQ ID NO:275) | HLA-B*3501 |
| HIV-1 5F2 | pol | 432-440 | EPIVGAETF (SEQ ID NO:276) | HLA-B*3501 |
| HIV-1 5F2 | pol | 6-14 | SPAIFQSSM (SEQ ID NO:277) | HLA-B*3501 |
| HIV-1 5F2 | pol | 59-68 | VPLDKDFRKY (SEQ ID NO:278) | HLA-B*3501 |
| HIV-1 5F2 | pol | 6-14 | IPLTEEAEL (SEQ ID NO:279) | HLA-B*3501 |
| HIV-1 5F2 | nef | 69-79 | RPQVPLRPMTY (SEQ ID NO:280) | HLA-B*3501 |
| HIV-1 5F2 | nef | 66-74 | FPVRPQVPL (SEQ ID NO:281) | HLA-B*3501 |
| HIV-1 5F2 | env | 10-18 | DPNPQEVVL (SEQ ID NO:282) | HLA-B*3501 |
| HIV-1 5F2 | env | 7-15 | RPIVSTQLL (SEQ ID NO:283) | HLA-B*3501 |
| HIV-1 5F2 | pol | 6-14 | IPLTEEAEL (SEQ ID NO:284) | HLA-B51 |
| HIV-1 5F2 | env | 10-18 | DPNPQEVVL (SEQ ID NO:285) | HLA-B51 |
| HIV-1 5F2 | gagp24 | 199-207 | AMQMLKETI (SEQ ID NO:286) | H2-Kd |
| HIV-2 | gagp24 | 182-190 | TPYDrNQML (SEQ ID NO:287) | HLA-B*5301 |
| HIV-2 | gag | 260-269 | RRWIQLGLQKV (SEQ ID NO:288) | HLA-B*2703 |
| HIV-1 5F2 | gp41 | 593-607 | GIWGCSGKLICTTAV (SEQ ID NO:289) | HLA-B17 |
| HIV-1 5F2 | gp41 | 753-767 | ALIWEDLRSLCLFSY (SEQ ID NO:290) | HLA-B22 |
| HPV 6b | E7 | 21-30 | GLHCYEQLV (SEQ ID NO:291) | HLA-A*0201 |
| HPV 6b | E7 | 47-55 | PLKQHFQIV (SEQ ID NO:292) | HLA-A*0201 |
| HPV11 | E7 | 4-12 | RLVTLKDIV (SEQ ID NO:293) | HLA-A*0201 |
| HPV16 | E7 | 86-94 | TLGIVCPIC (SEQ ID NO:294) | HLA-A*0201 |
| HPV16 | E7 | 85-93 | GTLGIVCPI (SEQ ID NO:295) | HLA-A*0201 |

TABLE 5-continued

| Virus | Protein | AA Position | T cell epitope MHC ligand (Antigen) | MHC molecule |
|---|---|---|---|---|
| HPV16 | E7 | 12-20 | MLDLQPETT (SEQ ID NO:296) | HLA-A*0201 |
| HPV16 | E7 | 11-20 | YMLDLQPETT (SEQ ID NO:297) | HLA-A*0201 |
| HPV16 | E6 | 15-22 | RPRKLPQL (SEQ ID NO:298) | HLA-B7 |
| HPV16 | E6 | 49-57 | RAHYNIVTF (SEQ ID NO:299) | HW-Db |
| HSV | gp B | 498-505 | SSIEFARL (SEQ ID NO:300) | H2-Kb |
| HSV-1 | gp C | 480-488 | GIGIGVLAA (SEQ ID NO:301) | HLA-A*0201 |
| HSV-1 | 1CP27 | 448-456 | DYATLGVGV (SEQ ID NO:302) | H2-Kd |
| HSV-1 | ICP27 | 322-332 | LYRTFAGNPRA (SEQ ID NO:303) | H2-Kd |
| HSV-1 | UL39 | 822-829 | QTFDFGRL (SEQ ID NO:304) | H2-Kb |
| HSV-2 | gpC | 446-454 | GAGIGVAVL (SEQ ID NO:305) | HLA-A*0201 |
| HLTV-1 | TAX | 11-19 | LLFGYPVYV (SEQ ID NO:306) | HLA-A*0201 |
| Influenza | MP | 58-66 | GILGFVFTL (SEQ ID NO:307) | HLA-A*0201 |
| Influenza | MP | 59-68 | ILGFVFTLTV (SEQ ID NO:308) | HLA-A*0201 |
| Influenza | NP | 265-273 | ILRGSVAHK (SEQ ID NO:309) | HLA-A3 |
| Influenza | NP | 91-99 | KTGGPIYKR (SEQ ID NO:310) | HLA-A*6801 |
| Influenza | NP | 380-388 | ELRSRYWAI (SEQ ID NO:311) | HLA-B8 |
| Influenza | NP | 381-388 | LRSRYWAI (SEQ ID NO:312) | HLA-B*2702 |
| Influenza | NP | 339-347 | EDLRVLSFI (SEQ ID NO:313) | HLA-B*3701 |
| Influenza | NSI | 158-166 | GEISPLPSL (SEQ ID NO:314) | HLA-B44 |
| Influenza | NP | 338-346 | FEDLRVLSF (SEQ ID NO:315) | HLA-B44 |
| Influenza | NSI | 158-166 | GEISPLPSL (SEQ ID NO:316) | HLA-B*4402 |
| Influenza | NP | 338-346 | FEDLRVLSF (SEQ ID NO:317) | HLA-B*4402 |
| Influenza | PBI | 591-599 | VSDGGPKLY (SEQ ID NO:318) | HLA-A1 |
| Influenza A | NP | 44-52 | CTELKLSDY (SEQ ID NO:319) | HLA-A1 |
| Influenza | NSI | 122-130 | AIMDKNIIL (SEQ ID NO:320) | HLA-A*0201 |

TABLE 5-continued

| Virus | Protein | AA Position | T cell epitope MHC ligand (Antigen) | MHC molecule |
|---|---|---|---|---|
| Influenza A | NSI | 123-132 | IMDKNIILKA (SEQ ID NO:321) | HLA-A*0201 |
| Influenza A | NP | 383-391 | SRYWAIRTR (SEQ ID NO:322) | HLA-B*2705 |
| Influenza A | NP | 147-155 | TYQRTRALV (SEQ ID NO:323) | H2-Kd |
| Influenza A | HA | 210-219 | TYVSVSTSTL (SEQ ID NO:324) | H2-Kd |
| Influenza A | HA | 518-526 | IYSTVASSL (SEQ ID NO:325) | H2-Kd |
| Influenza A | HA | 259-266 | FEANGNLI (SEQ ID NO:326) | H2-Kk |
| Influenza A | HA | 10-18 | IEGGWTGMI (SEQ ID NO:327) | H2-Kk |
| Influenza A | NP | 50-57 | SDYEGRLI (SEQ ID NO:328) | H2-Kk |
| Influenza a | NSI | 152-160 | EEGAIVGEI (SEQ ID NO:329) | H2-Kk |
| Influenza A34 | NP | 336-374 | ASNENMETM (SEQ ID NO:330) | H2Db |
| Influenza A68 | NP | 366-374 | ASNENMDAM (SEQ ID NO:331) | H2Db |
| Influenza B | NP | 85-94 | KLGEFYNQMM (SEQ ID NO:332) | HLA-A*0201 |
| Influenza B | NP | 85-94 | KAGEFYNQMM (SEQ ID NO:333) | HLA-A*0201 |
| Influenza JAP | HA | 204-212 | LYQNVGTYV (SEQ ID NO:334) | H2Kd |
| Influenza JAP | HA | 210-219 | TYVSVGTSTL (SEQ ID NO:335) | H2-Kd |
| Influenza JAP | HA | 523-531 | VYQILATYA (SEQ ID NO:336) | H2-Kd |
| Influenza JAP | HA | 529-537 | IYATVAGSL (SEQ ID NO:337) | H2-Kd |
| Influenza JAP | HA | 210-219 | TYVSVGTSTI (L > I) (SEQ ID NO:338) | H2-Kd |
| Influenza JAP | HA | 255-262 | FESTGNLI (SEQ ID NO:339) | H2-Kk |
| JHMV | cAg | 318-326 | APTAGAFFF (SEQ ID NO:340) | H2-Ld |
| LCMV | NP | 118-126 | RPQASGVYM (SEQ ID NO:341) | H2-Ld |
| LCMV | NP | 396-404 | FQPQNGQFI (SEQ ID NO:342) | H2-Db |
| LCMV | GP | 276-286 | SGVENPGGYCL (SEQ ID NO:343) | H2-Db |
| LCMV | GP | 33-42 | KAVYNFATCG (SEQ ID NO:344) | H2-Db |
| MCMV | pp89 | 168-176 | YPHFMPTNL (SEQ ID NO:345) | H2-Ld |

TABLE 5-continued

| Virus | Protein | AA Position | T cell epitope MHC ligand (Antigen) | MHC molecule |
|---|---|---|---|---|
| MHV | spike protein | 510-518 | CLSWNGPHL (SEQ ID NO:346) | H2-Db |
| MVF | protein | 437-447 | SRRYPDAVYLH (SEQ ID NO:347) | HLA-B*2705 |
| Mv | F protein | 438-446 | RRYPDAVYL (SEQ ID NO:348) | HLA-B*2705 |
| Mv | NP | 281-289 | YPALGLHEF (SEQ ID NO:349) | H2-Ld |

TABLE 6

HLA Class I Motifs

| Sequence (Antigen) | Source | Ref. |
|---|---|---|
| IVTDFSVIK (SEQ ID NO:350) | EBNA-4 416-424 | 115, 117 |
| VPLRPMTYK (SEQ ID NO:351) | HIV-1 NEF 74-82 | 115 |
| AIFQSSMTK (SEQ ID NO:352) | HIV-1 gag p24 325-333 | 115 |
| QVPLRPMTYK (SEQ ID NO:353) | HIV-1 nef 73-82 | 118 |
| AAVDLSHFLKEK (SEQ ID NO:354) | HIV-1 nef 83-94 | 120 |
| ACQGVGGPGGHK (SEQ ID NO:355) | HIV-1 II 1B p24 349-359 | 122 |
| RYLKDQQLL (SEQ ID NO:356) | HIV GP 41 583-591 | 124 |
| RYSIFFDY (SEQ ID NO:357) | Ebna-3 246-253 | 101 |
| ETINEEAAEW (SEQ ID NO:358) | HIV-1 gag p24 203-212 | 127 |
| STLPETTVVRR (SEQ ID NO:359) | HBV cAg 141-151 | 129 |
| MSLQRQFLR (SEQ ID NO:360) | ORF 3P-gp75 294-321 (bp) | 130 |
| IVGLNKIVR (SEQ ID NO:361) | HIV gag p24 267-267-275 | 132, 133 |
| TIHDIILEC (SEQ ID NO:362) | HPV16 E6 29-37 | 97 |
| LGIVCPICS (SEQ ID NO:363) | HPV16 E7 87-95 | 97 |
| FLPSDFFPSV (SEQ ID NO:364) | HBV cAg 18-27 | 51 |
| SVRDRLARL (SEQ ID NO:365) | EBNA-3 464-472 | 101 |
| FLPSDFFPSV (SEQ ID NO:366) | HBV cAg 18-27 | 51 |
| FLPSDFFPSV (SEQ ID NO:367) | HBV cAg 18-27 | 51 |

TABLE 6-continued

HLA Class I Motifs

| Sequence (Antigen) | Source | Ref. |
|---|---|---|
| RLRDLLLIVTR (SEQ ID NO:368) | HIV-1 gp41 768-778 | 108 |
| QVPLRPMTYK (SEQ ID NO:369) | HIV-1 nef 73-82 | 109 |
| TVYYGVPVWK (SEQ ID NO:370) | HIV-1 gp120-36-45 | 110 |
| RLRPGGKKK (SEQ ID NO:371) | HIV-1 gag p 17 20-29 | 110 |
| ILRGSVAHK (SEQ ID NO:372) | Influenza NP 265-273 | 21 |
| RLRAEAGVK (SEQ ID NO:373) | EBNA-3 603-611 | 111 |
| RLRDLLLIVTR (SEQ ID NO:374) | HIV-1 gp41 770-780 | 112 |
| VYYGVPVWK (SEQ ID NO:375) | HIV-I GP 120 38-46 | 113 |
| RVCEKMALY (SEQ ID NO:376) | HCV NS5 575-583 | 114 |
| VSDGGPNLY (SEQ ID NO:377) | Influenza A PB 1591-599 | 21, 23 |
| CTELKLSDY (SEQ ID NO:378) | Influenza A NP 44-52 | 23 |
| STBXQSGXQ (SEQ ID NO:379) | HBV PRE-S PROTEIN 141-149 | 43 |
| ILKEPVHGV (SEQ ID NO:380) | HIV- I RT 476-484 | 4, 31, 47 |
| LLGFVFTLTV (SEQ ID NO:381) | Influenza MP 59-68 | 4, 39 |
| LLFGYPVYV (SEQ ID NO:382) | HTLV-1 tax 11-19 | 40 |
| GLSPTVWLSV (SEQ ID NO:383) | HBV sAg 348-357 | 48 |
| WLSLLVPFV (SEQ ID NO:384) | HBV sAg 335-343 | 49, 50. 51 |
| FLPSDFFPSV (SEQ ID NO:385) | HBV cAg 18-27 | 52 |
| CLGOLLTMV (SEQ ID NO:386) | EBV LMP-2 426-434 | 48 |
| FLAGNSAYEYV (SEQ ID NO:387) | HCMV gp 618-628B | 53 |
| KLGEFYNQMM (SEQ ID NO:388) | Influenza BNP 85-94 | 54 |
| KLVALGINAV (SEQ ID NO:389) | HCV-1 NS3 400-409 | 55 |
| DLMGYIPLV (SEQ ID NO:390) | HCV MP 17-25 | 56 |
| RLVTLKDIV (SEQ ID NO:391) | HPV 11 EZ 4-12 | 34, 35 |
| AFHIIVAREL (SEQ ID NO:392) | HIV-I nef 190-198 | 63 |

TABLE 6-continued

HLA Class I Motifs

| Sequence (Antigen) | Source | Ref. |
|---|---|---|
| KAGEFYNQMM (SEQ ID NO:395) | Influenza BNP 85-94 | 65 |
| NIAEGLRAL (SEQ ID NO:396) | EBNA-1 480-488 | 66 |
| NLRRGTALA (SEQ ID NO:397) | EBNA-1 519-527 | 66 |
| ALAIPQCRL (SEQ ID NO:398) | EBNA-1 525-533 | 66 |
| VLKDAIKDL (SEQ ID NO:399) | EBNA-1 575-582 | 66 |
| FMVFLQTHI (SEQ ID NO:400) | EBNA-1 562-570 | 66 |
| HLIVDTDSL (SEQ ID NO:401) | EBNA-2 15-23 | 66 |
| SLGNPSLSV (SEQ ID NO:402) | EBNA-2 22-30 | 66 |
| PLASAMRML (SEQ ID NO:403) | EBNA-2 126-134 | 66 |
| RMLWMANYI (SEQ ID NO:404) | EBNA-2 132-140 | 66 |
| MLWMANYIV (SEQ ID NO:405) | EBNA-2 133-141 | 66 |
| ILPQGPQTA (SEQ ID NO:406) | EBNA-2 151-159 | 66 |
| PLRPTAPTTI (SEQ ID NO:407) | EBNA-2 171-179 | 66 |
| PLPPATLTV (SEQ ID NO:408) | EBNA-2 205-213 | 66 |
| RMHLPVLHV (SEQ ID NO:409) | EBNA-2 246-254 | 66 |
| PMPLPPSQL (SEQ ID NO:410) | EBNA-2 287-295 | 66 |
| QLPPPAAPA (SEQ ID NO:411) | EBNA-2 294-302 | 66 |
| SMPELSPVL (SEQ ID NO:412) | EBNA-2 381-389 | 66 |
| DLDESWDYI (SEQ ID NO:413) | EBNA-2 453-461 | 66 |
| PLPCVLWPVV (SEQ ID NO:414) | BZLF1 43-51 | 66 |
| SLEECDSEL (SEQ ID NO:415) | BZLF1 167-175 | 66 |
| EIKRYKNRV (SEQ ID NO:416) | BZLFI 176-184 | 66 |
| QLLQFIYREV (SEQ ID NO:417) | BZLF1 195-203 | 66 |
| LLQHYREVA (SEQ ID NO:418) | BZLFI 196-204 | 66 |
| LLKQMCPSL (SEQ ID NO:419) | BZLFI 217-225 | 66 |

TABLE 6-continued

HLA Class I Motifs

| Sequence (Antigen) | Source | Ref. |
|---|---|---|
| SIIPRTPDV (SEQ ID NO:420) | BZLFI 229-237 | 66 |
| AIMDKNIIL (SEQ ID NO:421) | Influenza A NS1 122-130 | 67 |
| IMDKNIILKA (SEQ ID NO:422) | Influenza A NS1 123-132 | 67 |
| LLALLSCLTV (SEQ ID NO:423) | HCV MP 63-72 | 69 |
| ILHTPGCV (SEQ ID NO:424) | HCV MP 105-112 | 69 |
| QLRRHIDLLV (SEQ ID NO:425) | HCV env E 66-75 | 69 |
| DLCGSVFLV (SEQ ID NO:426) | HCV env E 88-96 | 69 |
| SMVGNWAKV (SEQ ID NO:427) | HCV env E 172-180 | 69 |
| HLHQNIVDV (SEQ ID NO:428) | HCV NSI 308-316 | 69 |
| FLLLADARV (SEQ ID NO:429) | HCV NSI 340-348 | 69 |
| GLRDLAVAVEPVV (SEQ ID NO:430) | HCV NS2 234-246 | 69 |
| SLLAPGAKQNV (SEQ ID NO:431) | HCV NS1 18-28 | 69 |
| LLAPGAKQNV (SEQ ID NO:432) | HCV NS1 19-28 | 69 |
| FLLSLGIHL (SEQ ID NO:433) | HBV pol 575-583 | 70 |
| SLYADSPSV (SEQ ID NO:434) | HBV pol 816-824 | 70 |
| GLSRYVARL (SEQ ID NO:435) | HBV POL 455-463 | 70 |
| KLTPLCVTL (SEQ ID NO:438) | HIV-I gp 160 120-128 | 72 |
| SLLNATDIAV (SEQ ID NO:439) | HIV-I GP 160 814-823 | 72 |
| LLFNILGGWV (SEQ ID NO:441) | HCV N54 192-201 | 74 |
| LLVPFVQWFW (SEQ ID NO:442) | HBV env 338-347 | 74 |
| ALMPLYACI (SEQ ID NO:443) | HBV pol 642-650 | 74 |
| YLVAYQATV (SEQ ID NO:444) | HCV NS3 579-587 | 74 |
| YLLPRRGPRL (SEQ ID NO:446) | HCV core protein 34-43 | 74 |
| LLPIFFCLWV (SEQ ID NO:447) | HBV env 378-387 | 74 |
| YMDDVVLGA (SEQ ID NO:448) | HBV Pol 538-546 | 74 |

TABLE 6-continued

HLA Class I Motifs

| Sequence | (Antigen) Source | Ref. |
|---|---|---|
| GTLGIVCPI (SEQ ID NO:449) | HPV16 E7 85-93 | 74 |
| LLALLSCLTI (SEQ ID NO:450) | HCV MP 63-72 | 74 |
| MLDLQPETT (SEQ ID NO:451) | HPV 16 E7 12-20 | 74 |
| SLMAFTAAV (SEQ ID NO:452) | HCV NS4 174-182 | 75 |
| CINGVCWTV (SEQ ID NO:453) | HCV NS3 67-75 | 75 |
| LLCPAGHAV (SEQ ID NO:455) | HCV NS3 163-171 | 54 |
| ILDSFDPLV (SEQ ID NO:456) | HCV NS5 239-247 | 54 |
| LLLCLIFLL (SEQ ID NO:457) | HBV env 250-258 | 79 |
| LIDYQGMLPV (SEQ ID NO:458) | HBV env 260-269 | 79 |
| SIVSPFIPLL (SEQ ID NO:459) | HBV env 370-379 | 79 |
| FLLTRILTI (SEQ ID NO:460) | HBV env 183-191 | 80 |
| ILAGYGAGV (SEQ ID NO:463) | HCV NS S4A 236-244 | 82 |
| GLQDCTMLV (SEQ ID NO:464) | HCV NS5 714-722 | 82 |
| TGAPVTYSTY (SEQ ID NO:465) | HCV NS3 281-290 | 83 |
| VIYQYMDDLV (SEQ ID NO:466) | HIV-1RT 179-187 | 84 |
| (SEQ ID NO:468) | | |
| GIGIGVLAA (SEQ ID NO:472) | HSV-I gp C 480-488 | 86 |
| GAGIGVAVL (SEQ ID NO:473) | HSV-2 gp C 446-454 | 86 |
| IAGIGILAI (SEQ ID NO:474) | Pseudorabies gpGIN 455-463 | 86 |
| SLYNTVATL (SEQ ID NO:484) | HIV-I gag p 17 77-85 | 99 |
| RGPGRAFVTI (SEQ ID NO:486) | HIV-I gp 160 315-329 | 90 |
| HMWNFISGI (SEQ ID NO:487) | HCV NS4A 149-157 | 91 |
| NLVPMVATVQ (SEQ ID NO:488) | HCMV pp65 495-504 | 92 |
| GLHCYEQLV (SEQ ID NO:489) | HPV 6b E7 21-30 | 93 |
| PLKQHFQIV (SEQ ID NO:490) | HPV 6b E7 47-55 | 93 |

TABLE 6-continued

HLA Class I Motifs

| Sequence (Antigen) | Source | Ref. |
|---|---|---|
| LLDFVRFMGV (SEQ ID NO:491) | EBNA-6 284-293 | 95 |
| AIMEKNIML (SEQ ID NO:492) | Influenza Alaska NS 1 122-130 | 67 |
| YMLDLQPETT (SEQ ID NO:495) | HPV 16 E7 11-20* | 97 |
| LLMGTLGIV (SEQ ID NO:496) | HPV16 E7 82-90** | 97 |
| TLGIVCPI (SEQ ID NO:497) | HPV 16 E7 86-93 | 97 |
| TLTSCNTSV (SEQ ID NO:498) | HIV-1 gp120 197-205 | 98 |
| KLPQLCTEL (SEQ ID NO:499) | HPV 16 E6 18-26 | 97 |
| YVNVNMGLK* (SEQ ID NO:337) | HBV cAg 88-96 | 116 |

*Ref numbers refer to the references listed in Han-Georg Rammensee, Jutta Bachmann, and Stefan Stevanovic entitled "MHC Ligands and Peptide Motifs," Springer-Verlag, Germany, 1997 Landes Bioscience, Austin, Texas); which is incorporated herein by reference in its entirety for any purpose, including for example, epitope prediction technique, epitope, antigen, microbe or cell type.

TABLE 7

Listing of Various Viruses, Viral Antigens, and Epitopes

| HIV | herpes simplex virus (HSV), | HBV | HCV | human papilloma virus (HPV) | cytomegalovirus (CMV) |
|---|---|---|---|---|---|
| Antigens: Env, Gag, Nef and Pol Tat proteins, including gp120, gp160, gp41, p24gag and p55gag envelope proteins, derived from HIV such as, including members of the various genetic subtypes of HIV isolates HIV.sub.IIIb, HIV.sub.SF2, HIV.sub.LAV, HIV.sub.LAI, HIV.sub.MN, HIV-1.sub.CM235, HIV-1.sub.US4, HIV-2; proteins derived from simian immunodeficiency virus (SIV) | (HSV) types 1 and 2, such as HSV-1 and HSV-2 glycoproteins gB, gD and gH | HBc-IgG Ag HBV core IgG Ag HBc-IgG antigen Hepatitis B e antigen (HBeAg) | | | CMV gB and gH |

TABLE 7-continued

Listing of Various Viruses, Viral Antigens, and Epitopes

| Epitopes: HIV-1 RT 476-484 | HBV pre-S protein 141-149 | | | | |
|---|---|---|---|---|---|
| Respiratory syncytial virus (RSV) | Epstein Barr virus (EBV) | measles virus | human T-cell leukemia virus (HTLV) | Ebola virus | influenza virus |
| | | | | EBO-Z viral antigens EBO-S and EBO-Z virus antigens | Influenza A PB1 591-599 Influenza A NP 44-52 Influenza MP 58-66 Influenza MP 59-68 |

The following examples are for illustrative purposes only and are not intended to limit the scope of the various embodiments in any way.

Example 1

Immunogenic Compositions (e.g., Viral Vaccines)

Six groups (n=6) of HLA-A2 transgenic mice are injected with 25 ug of plasmid vector bilaterally in the inguinal lymph nodes, according to the following schedule: day 0, 3, 14 and 17. The vector encodes three A2 restricted epitopes from HIV gag (SLYNTVATL (SEQ ID NO:1), VLAEAMSQV (SEQ ID NO:2), MTNNPPIPV (SEQ ID NO:3)), two from pol (KLVGKLNWA (SEQ ID NO:4), ILKEPVHGV (SEQ ID NO:5)) and one from env (KLTPLCVTL (SEQ ID NO:6)). Two weeks after the last cycle of entrainment, mice are injected with mixtures encompassing all of these five peptides (5 ug/peptide/node bilaterally three days apart). In parallel, five groups of mice are injected with individual peptides (5 ug/peptide/node bilaterally three days apart). Seven days later the mice are bled and response is assessed by tetramer staining against each peptide. Afterwards, half of the mice are challenged with recombinant Vaccinia viruses expressing env, gag or pol ($10^3$ TCID$_{50}$/mouse) and at 7 days, the viral titer is measured in the ovaries by using a conventional plaque assay. The other half are sacrificed, the splenocytes are stimulated with peptides for 5 days and the cytotoxic activity is measured against target cells coated with peptides. As controls, mice are injected with plasmid or peptides alone. Mice entrained with plasmid and amplified with peptides show stronger immunity against all five peptides, by tetramer staining and cytotoxicity.

Thus, cytotoxic immunity can be generated in various cases, by the methodology described, without including epitopes that bind to MHC class II and thus have the possibility to interact with, activate and/or expand Th cells. It results then that cytotoxic immunity can be generated in absence of functional Th cells (conditions in which Th cells are affected by a pathologic process—such as resulting from HIV infection; or conditions that affect. Th cell function indirectly, due to abnormalities of antigen presenting cells—caused by viruses such as HBV, HCV and EBV). Further, use of peptides corresponding to MHC class I-restricted epitopes in context of the methodology mentioned above, overcomes the need for antigen processing and thus may deal with situations mentioned above, in which the function of APC is diminished. In addition, bypassing the employment of Th cells in inducing a therapeutic response comprising CTL, can circumvent potential immunopathology mediated by expanded CD4$^+$ Th response in viral infections such as those caused by HSV.

More generally, in order to break tolerance, restore immune responsiveness or induce immunity against non-self antigens such as viral, bacterial, parasitic or microbial, subjects, such as mice, humans, or other mammals, are immunized with: vectors such as plasmids; viruses; peptide plus adjuvant (CpG, dsRNA, TLR mimics); recombinant protein plus an adjuvant (CpG, dsRNA, TLR mimics); killed microbes or purified antigens, such as cell wall components; and are boosted by intranodal injection with peptide (corresponding to a target epitope for which they were immunized) without adjuvant. The immune response measured before and after boost by tetramer staining and other methods shows a substantial increase in the magnitude of immune response. Such a strategy can be used to protect against infection or treat chronic infections caused by agents such as HBV, HCV, HPV, CMV, influenza virus, HIV, HTLV, RSV, etc. It should be noted that the above methodology and the other methodologies described elsewhere herein can be used to treat non-human animals, where avoidance or minimization of CD4+ cells is advantageous. For example the methods can be used to treat infections by viruses in felines and canines, avians such as for example, chickens and turkeys, bovines, equines, other livestock and farm animals, and any other animal. See Table 7, above.

Example 2

Induction of Immune Response to MHC Class I-Restricted Epitopes by Intranodal Administration of Peptides Corresponding to Such Defined Epitopes and Adjuvant (Synthetic dsRNA)

A*0201 transgenic mice (n=4/group) were immunized with the following known MHC class I restricted peptide epitopes: HBVc 18-27 (FLPSDFFPSD; SEQ ID NO:7), PSMA 730-739 (RQIYVAAFTV; SEQ ID NO:8), PRAME 300-309 (SLLQHLIGL; SEQ ID NO:9) or PRAME 425-433 (ALYVDSLFFL; SEQ ID NO:10) admixed with synthetic dsRNA (poly(IC), by direct inoculation into the inguinal lymph nodes using 12.5 μg peptide+12.5 μg of adjuvant, in 25 μl of PBS/each inguinal lymph node at day 0, 3, 14 and 17).

One week after the final administration, splenocytes were stimulated ex vivo with 10 μg/ml of the same peptide in presence of 5 U/ml of rIL-2 and tested in a standard cytotoxic assay, against: $^{51}$Cr-labeled target cells (T2 cells) uncoated, coated with cognate peptide or negative control peptide, at various Effector:Target ratios (FIGS. 1-2); or similarly labeled MCF-7 cells coated with PRAME 730-739, PRAME 425-433 or uncoated.

The radioactivity released in the supernatant over 4 hours was measured using a γ (gamma)-counter. The response was quantified as % lysis=(sample signal−background)/(maximal signal−background)×100, where background represents radioactivity released by target cells alone when incubated in assay medium, and the maximal signal is the radioactivity released by target cells lysed with detergent.

Example 3

Specific Activation in the CD8$^+$ Lymphocyte Subset

Splenocytes isolated from pSEM plasmid primed, Melan-A 26-35 (A27L; SEQ ID NO: 1) peptide boosted HHD-1 transgenic mice were stimulated with a Melan-A specific tetramer reagent for 4 hrs. A fuller description of pSEM can be found in U.S. Patent Publication No. 2003-0228634, published on Dec. 11, 2003, and in U.S. Patent Publication No. 2005-0079152, published on Apr. 14, 2005 each of which is incorporated herein by reference in its entirety. Cells were then washed and stained with a rat anti-mouse CD8 antibody for 30 minutes. Cells were washed, permeabilized, and then stained intracellularly with anti-mouse-IFN-γ antibody for 30 minutes. Cells were washed, fixed and analyzed on a FACS Calibur flowcytometer. A gate (R1) was drawn around the total lymphocyte population (FIG. 4A) and the percentage of Melan-A antigen specific CTLs was determined by co-staining with CD8 (FIG. 4B). It is seen in FIG. 4C that only CD8 positive cells within the total lymphocyte population were activated following antigen stimulation with 15.7% of these cells capable of producing IFN-g compared to 0.2% of the CD8 negative fraction. This demonstrates that following Melan-A immunization, only cytotoxic T cells were activated upon additional antigen stimulation, reflecting the predominant effect of this immunization protocol on the CD8$^+$ population rather than the CD4$^+$ population.

The results showed in FIGS. 1-4, demonstrate successful induction of peptide specific cytotoxic immunity against target cells expressing MHC class I (known to be mediated by CTL—or cytotoxic lymphocytes that are MHC class I-restricted CD8$^+$ T cells), by intranodal administration of peptides corresponding to known MHC class I epitopes, together with poly IC.

The scientific literature is rich with descriptions of both antibody and CTL (class I MHC-restricted) epitopes from viral target proteins, including HIV, HSV, HBV, HCV, and EBV, which can be used in the various embodiments described herein. Advantageous choices of particular target proteins will be apparent to one of skill in the art pertaining to the individual viruses (or other pathogens). In some cases CTL or antibody epitopes, or their use, are described in the literature along with class II-MHC restricted epitopes. Indeed, inclusion of class II MHC-restricted epitopes in some cases in the literature is reported as being preferred or essential. Nonetheless, when such CTL or antibody epitopes are utilized in some preferred embodiments, preferably they can be used without inclusion of such class II MHC-restricted epitopes. Examples of CTL epitopes for HIV are disclosed in U.S. Pat. No. 6,656,471; and in Wilson, C. C., et al., *J. Immunol.* 171:5611-5623, 2003. Many other epitopes are known by those of skill in the art.

The term "consists essentially of" as used herein means that the scope of what is included is limited to the specified materials or steps and those that do not materially affect the basic and novel characteristic(s) of the embodiment.

In some embodiments, the numbers expressing quantities of ingredients, properties such as molecular weight, reaction conditions, and so forth used to describe and claim certain embodiments of the invention are to be understood as being modified in some instances by the term "about." Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the numbers expressing quantities of ingredients, properties such as molecular weight, reaction conditions, and so forth used to describe and claim certain embodiments of the invention are to be understood as being modified in some instances by the term "about." Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar referents used in the context of describing a particular embodiment of the invention (especially in the context of certain of the following claims) may be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans may employ such variations as appropriate, and the invention may be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety for any of the materials, substances, compositions of matter, methodologies, and devices described therein.

In closing, it is to be understood that the embodiments of the invention disclosed herein are illustrative of the principles of the present invention. Other modifications that may be employed may be within the scope of the invention. Thus, by way of example, but not of limitation, alternative configurations of the present invention may be utilized in accordance with the teachings herein. Accordingly, the present invention is not limited to that precisely as shown and described.

What is claimed:

1. A method of immunization, the method comprising the steps of:
   delivering directly to a lymphatic system of a mammal a composition comprising an immunogen, the immunogen comprising a class I MHC-restricted epitope or a B cell epitope, wherein the composition does not comprise an effective class II MHC-restricted epitope; and
   administering an immunopotentiator to the mammal such that an epitope-specific immune response is induced without substantial activation or expansion of CD4$^+$ T cells.

2. The method of claim 1 where in the epitope is an HIV epitope.

3. The method of claim 1 wherein the immunogen and the immunopotentiator are co-administered to the lymphatic system.

4. The method of claim 1 wherein the composition comprises a first immunogen comprising a class I MHC-restricted epitope and a second immunogen comprising a B cell epitope.

5. The method of claim 4 wherein the first immunogen and the second immunogen are the same.

6. The method of claim 1 comprising co-administering a first immunogen comprising or encoding the class I MHC-restricted epitope with the immunopotentiator, and subsequently delivering a second immunogen comprising the epitope, in the form of an epitopic peptide, to the lymphatic system of the mammal.

7. The method of claim 6 wherein the interval between the administering step and the delivering step is at least about seven days.

8. The method of claim 6 wherein the first immunogen comprises a nucleic acid encoding the epitope.

9. The method of claim 6 wherein the immunopotentiator comprises a DNA molecule comprising a CpG sequence.

10. The method of claim 8 wherein the nucleic acid comprises a DNA molecule comprising a CpG sequence which constitutes the immunopotentiator.

11. The method of claim 6 wherein the immunopotentiator comprises dsRNA.

12. The method of claim 6 wherein the first immunogen comprises a polypeptide.

13. The method of claim 1 wherein delivery to the lymphatic system comprises delivery to a lymph node or lymph vessel.

14. A method of immunization comprising:

a step for potentiating an immune response, a step for directly exposing the lymphatic system to a class I MHC-restricted epitope or a B cell epitope, wherein an epitope-specific immune response is induced without substantial activation or expansion of $CD4^+$ T cells.

15. A method of immunization comprising:
delivering to a mammal a first composition comprising a first immunogen, the first immunogen comprising or encoding at least a portion of a first antigen; and subsequently
administering a second composition comprising an epitopic peptide directly to the lymphatic system of the mammal, wherein the peptide corresponds to a class I MHC-restricted epitope of said first antigen, wherein said second composition is not the same as the first composition such that an epitope-specific immune response is amplified without substantial activation or expansion of CD4+ T cells.

16. A method of generating an immune response against a disease-related antigen in which it is advantageous to minimize the expansion of CD4+ lymphocytes, comprising:
delivering to an animal a first immunogen and an immunopotentiator, the first immunogen comprising or encoding at least a first portion of a first antigen, wherein said first immunogen does not comprise a class II MHC restricted epitope for an MHC expressed by said animal; and
administering subsequent to said delivering step an epitopic peptide directly to a lymphatic system of the animal, wherein the peptide corresponds to a class I MHC-restricted epitope of said first antigen, wherein said epitopic peptide is not the same as the first immunogen.

17. The method of claim 16, wherein the disease is caused by HIV.

18. The method of claim 16, wherein the disease is caused by a virus selected from the group consisting of HSV, HBV, HCV, EBV, HPV, CMV, influenza virus, HTLV, RSV, EBV, measles virus, and Ebola virus.

19. The method of claim 16, wherein the animal is a human.

20. The method of claim 16, wherein the animal is a non-human animal.

21. The method of claim 20, wherein said non-human animal is a mammal.

22. The method of claim 16, wherein said first immunogen and said immunopotentiator are delivered to a lymphatic system of the animal.

23. The method of claim 22, wherein said first immunogen and said immunopotentiator are delivered to a lymph node.

24. The method of claim 16, wherein said epitopic peptide is delivered to a lymph node.

25. The method of claim 16, wherein said first immunogen and said immunopotentiator are delivered to a same location on or in said animal.

26. The method of claim 16, wherein said first immunogen and said immunopotentiator are delivered simultaneously.

27. The method of claim 16, wherein said first immunogen and said immunopotentiator are delivered on the same day.

28. The method of claim 16, wherein said first immunogen and said immunopotentiator are delivered as part of a same composition.

29. The method of claim 16, wherein said at least a portion of a first antigen comprises a whole antigen.

30. The method of claim 16, wherein said at least a portion of a first antigen comprises less than the full-length of whole antigen.

31. The method of claim 30, wherein said at least a portion of a first antigen comprises a contiguous fragment of less than 80%, 70%, 60%, 50%, 40%, 30%, 20% or 10% of the whole antigen.

32. The method of claim 16, wherein said first immunogen encodes said at least a portion of a first antigen and comprises an immunostimulatory sequence that serves as said immunopotentiator.

33. The method of claim 31, wherein said first immunogen encodes one or more epitopes, wherein the one or more epitopes are class I restricted T cell epitopes or B cell epitopes.

34. The method of claim 33, wherein said administering step is performed about 7, 8, 9, 10, 11, 12, 13, 14, 15, 20, 25, 30 days or more after the delivering step.

35. The method of claim 16, wherein said at least a first portion of a first antigen does not comprise or encode any MHC class II restricted epitope for the species of said animal or does not comprise or encode any human class II restricted epitope.

36. The method of claim 16, wherein said first immunogen further comprises or encodes at least a second portion of said first antigen, wherein said at least a second portion of said first antigen does not comprise a class II MHC restricted epitope for an MHC expressed by said animal.

37. The method of claim 36, wherein said first immunogen encodes said at least a first portion of a first antigen and said at least a second portion of said first antigen.

38. The method of claim 36, wherein said first immunogen further comprises or encodes one or more additional portions of said first antigen, wherein said one or more additional portions of said first antigen do not comprise a class II MHC restricted epitope for an MHC expressed by said animal.

39. The method of claim 16, wherein said first immunogen further comprises or encodes at least a first portion of a second antigen.

40. The method of claim 16, wherein said delivering step further comprises delivering a second immunogen comprising or encoding at least a first portion of a second antigen, wherein said at least a first portion of a second antigen does not comprise a class II MHC restricted epitope for an MHC expressed by said animal.

41. The method of claim 16, further comprising detecting or obtaining an epitope-specific immune response without substantial activation or expansion of CD4+ T cells.

42. A method of generating an immune response against an HIV infection, comprising:
delivering to an animal a composition comprising a nucleic acid encoding a first immunogen and an immunopotentiator, the nucleic acid encoding at least a first portion of a first HIV antigen, wherein said composition does not comprise a class II MHC restricted epitope for an MHC expressed by said animal; and
administering subsequent to said delivering step an epitopic peptide directly to a lymphatic system of the animal, wherein the peptide corresponds to a class I MHC-restricted epitope of said at least a first portion of a first HIV antigen, wherein said epitopic peptide is not the same as the first immunogen.

43. The method of claim 42, wherein said first HIV antigen is selected from the group consisting of gag, pol, env, tat, gp120, gp160, gp41, nef, gag p, gp, gag p24, and rt.

44. The method of claim 42, wherein said nucleic acid encodes one or more of SEQ ID NOs: 1-6.

45. A method of generating an immune response against a cell infected by an HIV, comprising:
delivering to patient a composition comprising a nucleic acid encoding one or more of SEQ ID NOs:1-6 and an adjuvant, the nucleic acid encoding at least a first portion of a first HIV antigen, wherein said composition does not comprise a class II MHC restricted epitope for an MHC expressed by said patient, wherein said adjuvant is a CpG, a dsRNA poly IC, or a TLR mimic; and administering one or more epitopic peptides directly to a lymph node of the patient, wherein the peptide is one that was encoded by said nucleic acid or is an analog thereof.

* * * * *

SEQUENCE LISTING

```
<160> NUMBER OF SEQ ID NOS: 473

<210> SEQ ID NO 1
<211> LENGTH: 9
<212> TYPE: PRT
<213> ORGANISM: Human immunodeficiency virus

<400> SEQUENCE: 1

Ser Leu Tyr Asn Thr Val Ala Thr Leu
 1               5

<210> SEQ ID NO 2
<211> LENGTH: 9
<212> TYPE: PRT
<213> ORGANISM: Human immunodeficiency virus

<400> SEQUENCE: 2

Val Leu Ala Glu Ala Met Ser Gln Val
 1               5

<210> SEQ ID NO 3
<211> LENGTH: 9
<212> TYPE: PRT
<213> ORGANISM: Human immunodeficiency virus

<400> SEQUENCE: 3

Met Thr Asn Asn Pro Pro Ile Pro Val
 1               5

<210> SEQ ID NO 4
<211> LENGTH: 9
<212> TYPE: PRT
<213> ORGANISM: Human immunodeficiency virus

<400> SEQUENCE: 4

Lys Leu Val Gly Lys Leu Asn Trp Ala
 1               5

<210> SEQ ID NO 5
<211> LENGTH: 9
<212> TYPE: PRT
<213> ORGANISM: Human immunodeficiency virus
```

```
<400> SEQUENCE: 5

Ile Leu Lys Glu Pro Val His Gly Val
1               5

<210> SEQ ID NO 6
<211> LENGTH: 9
<212> TYPE: PRT
<213> ORGANISM: Human immunodeficiency virus

<400> SEQUENCE: 6

Lys Leu Thr Pro Leu Cys Val Thr Leu
1               5

<210> SEQ ID NO 7
<211> LENGTH: 10
<212> TYPE: PRT
<213> ORGANISM: Hepatitis B virus

<400> SEQUENCE: 7

Phe Leu Pro Ser Asp Phe Phe Pro Ser Asp
1               5                   10

<210> SEQ ID NO 8
<211> LENGTH: 10
<212> TYPE: PRT
<213> ORGANISM: Homo sapiens

<400> SEQUENCE: 8

Arg Gln Ile Tyr Val Ala Ala Phe Thr Val
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetically prepared peptide sequence

<400> SEQUENCE: 9

Ser Leu Leu Gln His Leu Ile Gly Leu
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetically prepared peptide sequence

<400> SEQUENCE: 10

Ala Leu Tyr Val Asp Ser Leu Phe Phe Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetically prepared peptide sequence

<400> SEQUENCE: 11

Glu Leu Ala Gly Ile Gly Ile Leu Thr Val
1               5                   10

<210> SEQ ID NO 12
<211> LENGTH: 9
```

```
<212> TYPE: PRT
<213> ORGANISM: Epstein-Barr Virus

<400> SEQUENCE: 12

Ala Tyr Pro Leu His Glu Gln His Gly
1               5

<210> SEQ ID NO 13
<211> LENGTH: 9
<212> TYPE: PRT
<213> ORGANISM: Epstein-Barr Virus

<400> SEQUENCE: 13

Tyr Leu Lys Ser Phe Val Ser Asp Ala
1               5

<210> SEQ ID NO 14
<211> LENGTH: 9
<212> TYPE: PRT
<213> ORGANISM: Epstein-Barr Virus

<400> SEQUENCE: 14

Arg Arg Arg Trp Arg Arg Leu Thr Val
1               5

<210> SEQ ID NO 15
<211> LENGTH: 9
<212> TYPE: PRT
<213> ORGANISM: Epstein-Barr Virus

<400> SEQUENCE: 15

Arg Arg Ile Tyr Asp Leu Ile Glu Leu
1               5

<210> SEQ ID NO 16
<211> LENGTH: 9
<212> TYPE: PRT
<213> ORGANISM: Epstein-Barr Virus

<400> SEQUENCE: 16

Tyr Pro Leu His Glu Gln His Gly Met
1               5

<210> SEQ ID NO 17
<211> LENGTH: 9
<212> TYPE: PRT
<213> ORGANISM: Epstein-Barr Virus

<400> SEQUENCE: 17

Tyr Pro Leu His Glu Gln His Gly Met
1               5

<210> SEQ ID NO 18
<211> LENGTH: 9
<212> TYPE: PRT
<213> ORGANISM: Epstein-Barr Virus

<400> SEQUENCE: 18

Cys Leu Gly Gly Leu Leu Thr Met Val
1               5

<210> SEQ ID NO 19
<211> LENGTH: 9
<212> TYPE: PRT
<213> ORGANISM: Epstein-Barr Virus
```

```
<400> SEQUENCE: 19

Asn Ile Ala Glu Gly Leu Arg Ala Leu
 1               5

<210> SEQ ID NO 20
<211> LENGTH: 9
<212> TYPE: PRT
<213> ORGANISM: Epstein-Barr Virus

<400> SEQUENCE: 20

Asn Leu Arg Arg Gly Thr Ala Leu Ala
 1               5

<210> SEQ ID NO 21
<211> LENGTH: 9
<212> TYPE: PRT
<213> ORGANISM: Epstein-Barr Virus

<400> SEQUENCE: 21

Ala Leu Ala Ile Pro Gln Cys Arg Leu
 1               5

<210> SEQ ID NO 22
<211> LENGTH: 9
<212> TYPE: PRT
<213> ORGANISM: Epstein-Barr Virus

<400> SEQUENCE: 22

Val Leu Lys Asp Ala Ile Lys Asp Leu
 1               5

<210> SEQ ID NO 23
<211> LENGTH: 9
<212> TYPE: PRT
<213> ORGANISM: Epstein-Barr Virus

<400> SEQUENCE: 23

Phe Met Val Phe Leu Gln Thr His Ile
 1               5

<210> SEQ ID NO 24
<211> LENGTH: 9
<212> TYPE: PRT
<213> ORGANISM: Epstein-Barr Virus

<400> SEQUENCE: 24

His Leu Ile Val Asp Thr Asp Ser Leu
 1               5

<210> SEQ ID NO 25
<211> LENGTH: 9
<212> TYPE: PRT
<213> ORGANISM: Epstein-Barr Virus

<400> SEQUENCE: 25

Ser Leu Gly Asn Pro Ser Leu Ser Val
 1               5

<210> SEQ ID NO 26
<211> LENGTH: 9
<212> TYPE: PRT
<213> ORGANISM: Epstein-Barr Virus

<400> SEQUENCE: 26

Pro Leu Ala Ser Ala Met Arg Met Leu
```

<210> SEQ ID NO 27
<211> LENGTH: 9
<212> TYPE: PRT
<213> ORGANISM: Epstein-Barr Virus

<400> SEQUENCE: 27

Arg Met Leu Trp Met Ala Asn Tyr Leu
1               5

<210> SEQ ID NO 28
<211> LENGTH: 9
<212> TYPE: PRT
<213> ORGANISM: Epstein-Barr Virus

<400> SEQUENCE: 28

Met Leu Trp Met Ala Asn Tyr Ile Val
1               5

<210> SEQ ID NO 29
<211> LENGTH: 9
<212> TYPE: PRT
<213> ORGANISM: Epstein-Barr Virus

<400> SEQUENCE: 29

Ile Leu Pro Gln Gly Pro Gln Thr Ala
1               5

<210> SEQ ID NO 30
<211> LENGTH: 9
<212> TYPE: PRT
<213> ORGANISM: Epstein-Barr Virus

<400> SEQUENCE: 30

Pro Leu Arg Pro Thr Ala Pro Thr Ile
1               5

<210> SEQ ID NO 31
<211> LENGTH: 9
<212> TYPE: PRT
<213> ORGANISM: Epstein-Barr Virus

<400> SEQUENCE: 31

Pro Leu Pro Pro Ala Thr Leu Thr Val
1               5

<210> SEQ ID NO 32
<211> LENGTH: 9
<212> TYPE: PRT
<213> ORGANISM: Epstein-Barr Virus

<400> SEQUENCE: 32

Arg Met His Leu Pro Val Leu His Val
1               5

<210> SEQ ID NO 33
<211> LENGTH: 9
<212> TYPE: PRT
<213> ORGANISM: Epstein-Barr Virus

<400> SEQUENCE: 33

Pro Met Pro Leu Pro Pro Ser Gln Leu
1               5

```
<210> SEQ ID NO 34
<211> LENGTH: 9
<212> TYPE: PRT
<213> ORGANISM: Epstein-Barr Virus

<400> SEQUENCE: 34

Gln Leu Pro Pro Pro Ala Ala Pro Ala
 1               5

<210> SEQ ID NO 35
<211> LENGTH: 9
<212> TYPE: PRT
<213> ORGANISM: Epstein-Barr Virus

<400> SEQUENCE: 35

Ser Met Pro Glu Leu Ser Pro Val Leu
 1               5

<210> SEQ ID NO 36
<211> LENGTH: 9
<212> TYPE: PRT
<213> ORGANISM: Epstein-Barr Virus

<400> SEQUENCE: 36

Asp Leu Asp Glu Ser Trp Asp Tyr Ile
 1               5

<210> SEQ ID NO 37
<211> LENGTH: 9
<212> TYPE: PRT
<213> ORGANISM: Epstein-Barr Virus

<400> SEQUENCE: 37

Pro Leu Pro Cys Val Leu Trp Pro Val
 1               5

<210> SEQ ID NO 38
<211> LENGTH: 9
<212> TYPE: PRT
<213> ORGANISM: Epstein-Barr Virus

<400> SEQUENCE: 38

Ser Leu Glu Glu Cys Asp Ser Glu Leu
 1               5

<210> SEQ ID NO 39
<211> LENGTH: 9
<212> TYPE: PRT
<213> ORGANISM: Epstein-Barr Virus

<400> SEQUENCE: 39

Glu Ile Lys Arg Tyr Lys Asn Arg Val
 1               5

<210> SEQ ID NO 40
<211> LENGTH: 9
<212> TYPE: PRT
<213> ORGANISM: Epstein-Barr Virus

<400> SEQUENCE: 40

Gln Leu Leu Gln His Tyr Arg Glu Val
 1               5

<210> SEQ ID NO 41
<211> LENGTH: 9
<212> TYPE: PRT
```

-continued

<213> ORGANISM: Epstein-Barr Virus

<400> SEQUENCE: 41

Leu Leu Gln His Tyr Arg Glu Val Ala
 1               5

<210> SEQ ID NO 42
<211> LENGTH: 9
<212> TYPE: PRT
<213> ORGANISM: Epstein-Barr Virus

<400> SEQUENCE: 42

Leu Leu Lys Gln Met Cys Pro Ser Leu
 1               5

<210> SEQ ID NO 43
<211> LENGTH: 9
<212> TYPE: PRT
<213> ORGANISM: Epstein-Barr Virus

<400> SEQUENCE: 43

Ser Ile Ile Pro Arg Thr Pro Asp Val
 1               5

<210> SEQ ID NO 44
<211> LENGTH: 10
<212> TYPE: PRT
<213> ORGANISM: Epstein-Barr Virus

<400> SEQUENCE: 44

Leu Leu Asp Phe Val Arg Phe Met Gly Val
 1               5                   10

<210> SEQ ID NO 45
<211> LENGTH: 9
<212> TYPE: PRT
<213> ORGANISM: Epstein-Barr Virus

<400> SEQUENCE: 45

Ser Val Arg Asp Arg Leu Ala Arg Leu
 1               5

<210> SEQ ID NO 46
<211> LENGTH: 9
<212> TYPE: PRT
<213> ORGANISM: Epstein-Barr Virus

<400> SEQUENCE: 46

Ile Val Thr Asp Phe Ser Val Ile Lys
 1               5

<210> SEQ ID NO 47
<211> LENGTH: 10
<212> TYPE: PRT
<213> ORGANISM: Epstein-Barr Virus

<400> SEQUENCE: 47

Ala Val Phe Asp Arg Lys Ser Asp Ala Lys
 1               5                   10

<210> SEQ ID NO 48
<211> LENGTH: 8
<212> TYPE: PRT
<213> ORGANISM: Epstein-Barr Virus

<400> SEQUENCE: 48

Arg Tyr Ser Ile Phe Phe Asp Tyr
1               5

<210> SEQ ID NO 49
<211> LENGTH: 9
<212> TYPE: PRT
<213> ORGANISM: Epstein-Barr Virus

<400> SEQUENCE: 49

Gln Pro Arg Ala Pro Ile Arg Pro Ile
1               5

<210> SEQ ID NO 50
<211> LENGTH: 9
<212> TYPE: PRT
<213> ORGANISM: Epstein-Barr Virus

<400> SEQUENCE: 50

Arg Pro Pro Ile Phe Ile Arg Arg Ile
1               5

<210> SEQ ID NO 51
<211> LENGTH: 9
<212> TYPE: PRT
<213> ORGANISM: Epstein-Barr Virus

<400> SEQUENCE: 51

Glu Pro Asp Val Pro Pro Gly Ala Ile
1               5

<210> SEQ ID NO 52
<211> LENGTH: 9
<212> TYPE: PRT
<213> ORGANISM: Epstein-Barr Virus

<400> SEQUENCE: 52

Ile Pro Gln Cys Arg Leu Thr Pro Leu
1               5

<210> SEQ ID NO 53
<211> LENGTH: 9
<212> TYPE: PRT
<213> ORGANISM: Epstein-Barr Virus

<400> SEQUENCE: 53

Gly Pro Gly Pro Gln Pro Gly Pro Leu
1               5

<210> SEQ ID NO 54
<211> LENGTH: 9
<212> TYPE: PRT
<213> ORGANISM: Epstein-Barr Virus

<400> SEQUENCE: 54

Gln Pro Gly Pro Leu Arg Glu Ser Ile
1               5

<210> SEQ ID NO 55
<211> LENGTH: 9
<212> TYPE: PRT
<213> ORGANISM: Epstein-Barr Virus

<400> SEQUENCE: 55

Arg Pro Gln Lys Arg Pro Ser Cys Ile
1               5

```
<210> SEQ ID NO 56
<211> LENGTH: 9
<212> TYPE: PRT
<213> ORGANISM: Epstein-Barr Virus

<400> SEQUENCE: 56

Pro Pro Thr Pro Leu Leu Thr Val Leu
1               5

<210> SEQ ID NO 57
<211> LENGTH: 9
<212> TYPE: PRT
<213> ORGANISM: Epstein-Barr Virus

<400> SEQUENCE: 57

Thr Pro Ser Pro Pro Arg Met His Leu
1               5

<210> SEQ ID NO 58
<211> LENGTH: 9
<212> TYPE: PRT
<213> ORGANISM: Epstein-Barr Virus

<400> SEQUENCE: 58

Pro Pro Arg Met His Leu Pro Val Leu
1               5

<210> SEQ ID NO 59
<211> LENGTH: 9
<212> TYPE: PRT
<213> ORGANISM: Epstein-Barr Virus

<400> SEQUENCE: 59

Val Pro Asp Gln Ser Met His Pro Leu
1               5

<210> SEQ ID NO 60
<211> LENGTH: 9
<212> TYPE: PRT
<213> ORGANISM: Epstein-Barr Virus

<400> SEQUENCE: 60

Pro Pro Ser Ile Asp Pro Ala Asp Leu
1               5

<210> SEQ ID NO 61
<211> LENGTH: 9
<212> TYPE: PRT
<213> ORGANISM: Epstein-Barr Virus

<400> SEQUENCE: 61

Leu Pro Cys Val Leu Trp Pro Val Leu
1               5

<210> SEQ ID NO 62
<211> LENGTH: 10
<212> TYPE: PRT
<213> ORGANISM: Epstein-Barr Virus

<400> SEQUENCE: 62

Cys Pro Ser Leu Asp Val Asp Ser Ile Ile
1               5                   10

<210> SEQ ID NO 63
```

```
<211> LENGTH: 9
<212> TYPE: PRT
<213> ORGANISM: Epstein-Barr Virus

<400> SEQUENCE: 63

Thr Pro Asp Val Leu His Glu Asp Leu
 1               5

<210> SEQ ID NO 64
<211> LENGTH: 9
<212> TYPE: PRT
<213> ORGANISM: Epstein-Barr Virus

<400> SEQUENCE: 64

Phe Leu Arg Gly Arg Ala Tyr Gly Leu
 1               5

<210> SEQ ID NO 65
<211> LENGTH: 9
<212> TYPE: PRT
<213> ORGANISM: Epstein-Barr Virus

<400> SEQUENCE: 65

Gln Ala Lys Trp Arg Leu Gln Thr Leu
 1               5

<210> SEQ ID NO 66
<211> LENGTH: 9
<212> TYPE: PRT
<213> ORGANISM: Hepatitis C Virus

<400> SEQUENCE: 66

His Ser Lys Lys Lys Cys Asp Glu Leu
 1               5

<210> SEQ ID NO 67
<211> LENGTH: 8
<212> TYPE: PRT
<213> ORGANISM: Hepatitis C Virus

<400> SEQUENCE: 67

Ala Ser Arg Cys Trp Val Ala Met
 1               5

<210> SEQ ID NO 68
<211> LENGTH: 9
<212> TYPE: PRT
<213> ORGANISM: Hepatitis C Virus

<400> SEQUENCE: 68

Gly Gln Ile Val Gly Gly Val Tyr Leu
 1               5

<210> SEQ ID NO 69
<211> LENGTH: 10
<212> TYPE: PRT
<213> ORGANISM: Hepatitis C Virus

<400> SEQUENCE: 69

Pro Pro Leu Thr Asp Phe Asp Gln Gly Trp
 1               5                  10

<210> SEQ ID NO 70
<211> LENGTH: 10
<212> TYPE: PRT
<213> ORGANISM: Hepatitis C Virus
```

```
<400> SEQUENCE: 70

Leu Met Gly Tyr Ile Pro Leu Val Gly Ala
1               5                   10

<210> SEQ ID NO 71
<211> LENGTH: 10
<212> TYPE: PRT
<213> ORGANISM: Hepatitis C Virus

<400> SEQUENCE: 71

Ala Asp Leu Met Gly Tyr Ile Pro Leu Val
1               5                   10

<210> SEQ ID NO 72
<211> LENGTH: 16
<212> TYPE: PRT
<213> ORGANISM: Hepatitis C Virus

<400> SEQUENCE: 72

Met Ser Tyr Ser Trp Thr Gly Ala Leu Val Thr Pro Cys Ala Glu Glu
1               5                   10                  15

<210> SEQ ID NO 73
<211> LENGTH: 9
<212> TYPE: PRT
<213> ORGANISM: Hepatitis C Virus

<400> SEQUENCE: 73

Lys His Pro Asp Ala Thr Tyr Ser Arg
1               5

<210> SEQ ID NO 74
<211> LENGTH: 9
<212> TYPE: PRT
<213> ORGANISM: Hepatitis C Virus (HCV-1)

<400> SEQUENCE: 74

Thr Arg Pro Pro Leu Gly Asn Trp Phe
1               5

<210> SEQ ID NO 75
<211> LENGTH: 9
<212> TYPE: PRT
<213> ORGANISM: Hepatitis C Virus (HCV-1)

<400> SEQUENCE: 75

Val Pro His Pro Asn Ile Glu Glu Val
1               5

<210> SEQ ID NO 76
<211> LENGTH: 9
<212> TYPE: PRT
<213> ORGANISM: Hepatitis C Virus (HCV-1)

<400> SEQUENCE: 76

Tyr Thr Gly Asp Phe Asp Ser Val Ile
1               5

<210> SEQ ID NO 77
<211> LENGTH: 8
<212> TYPE: PRT
<213> ORGANISM: Hepatitis C Virus (HCV-1)

<400> SEQUENCE: 77
```

```
Ser Trp Ala Ile Lys Trp Glu Tyr
1               5

<210> SEQ ID NO 78
<211> LENGTH: 9
<212> TYPE: PRT
<213> ORGANISM: Hepatitis C Virus (HCV-1)

<400> SEQUENCE: 78

Lys His Pro Asp Ala Thr Tyr Ser Arg
1               5

<210> SEQ ID NO 79
<211> LENGTH: 9
<212> TYPE: PRT
<213> ORGANISM: Hepatitis C Virus (HCV-1)

<400> SEQUENCE: 79

Gly Asp Phe Asp Ser Val Ile Asp Cys
1               5

<210> SEQ ID NO 80
<211> LENGTH: 10
<212> TYPE: PRT
<213> ORGANISM: Hepatitis C Virus (HCV-1)

<400> SEQUENCE: 80

Lys Leu Val Ala Leu Gly Ile Asn Ala Val
1               5                   10

<210> SEQ ID NO 81
<211> LENGTH: 9
<212> TYPE: PRT
<213> ORGANISM: Hepatitis C Virus (HCV-1)

<400> SEQUENCE: 81

Gly Asp Phe Asp Ser Val Ile Asp Cys
1               5

<210> SEQ ID NO 82
<211> LENGTH: 9
<212> TYPE: PRT
<213> ORGANISM: Hepatitis C Virus (HCV-1)

<400> SEQUENCE: 82

Gly Asn Ala Ser Arg Cys Trp Val Ala
1               5

<210> SEQ ID NO 83
<211> LENGTH: 9
<212> TYPE: PRT
<213> ORGANISM: Human Immunodeficiency Virus (HIV)

<400> SEQUENCE: 83

Thr Gln Gly Tyr Phe Pro Gln Trp Gln
1               5

<210> SEQ ID NO 84
<211> LENGTH: 9
<212> TYPE: PRT
<213> ORGANISM: Human Immunodeficiency Virus (HIV)

<400> SEQUENCE: 84

His Gln Ala Ile Ser Pro Arg Thr Ile
1               5
```

```
<210> SEQ ID NO 85
<211> LENGTH: 12
<212> TYPE: PRT
<213> ORGANISM: Human Immunodeficiency Virus (HIV)

<400> SEQUENCE: 85

Gln Met Val His Gln Ala Ile Ser Pro Arg Thr Leu
1               5                   10

<210> SEQ ID NO 86
<211> LENGTH: 10
<212> TYPE: PRT
<213> ORGANISM: Human Immunodeficiency Virus (HIV)

<400> SEQUENCE: 86

Met Tyr Ala Pro Pro Ile Gly Gly Gln Ile
1               5                   10

<210> SEQ ID NO 87
<211> LENGTH: 10
<212> TYPE: PRT
<213> ORGANISM: Human Immunodeficiency Virus (HIV)

<400> SEQUENCE: 87

Arg Gly Pro Gly Arg Ala Phe Val Thr Ile
1               5                   10

<210> SEQ ID NO 88
<211> LENGTH: 9
<212> TYPE: PRT
<213> ORGANISM: Human Immunodeficiency Virus (HIV)

<400> SEQUENCE: 88

Met Pro Gly Arg Ala Phe Val Thr Ile
1               5

<210> SEQ ID NO 89
<211> LENGTH: 9
<212> TYPE: PRT
<213> ORGANISM: Human Immunodeficiency Virus (HIV)

<400> SEQUENCE: 89

Arg Tyr Leu Lys Asp Gln Gln Leu Leu
1               5

<210> SEQ ID NO 90
<211> LENGTH: 9
<212> TYPE: PRT
<213> ORGANISM: Human Immunodeficiency Virus (HIV)

<400> SEQUENCE: 90

Ile Val Gly Leu Asn Lys Ile Val Arg
1               5

<210> SEQ ID NO 91
<211> LENGTH: 9
<212> TYPE: PRT
<213> ORGANISM: Human Immunodeficiency Virus (HIV)

<400> SEQUENCE: 91

Glu Ile Tyr Lys Arg Trp Ile Ile Leu
1               5

<210> SEQ ID NO 92
<211> LENGTH: 8
```

<212> TYPE: PRT
<213> ORGANISM: Human Immunodeficiency Virus (HIV)

<400> SEQUENCE: 92

Gly Glu Leu Tyr Lys Arg Trp Ile
1               5

<210> SEQ ID NO 93
<211> LENGTH: 9
<212> TYPE: PRT
<213> ORGANISM: Human Immunodeficiency Virus (HIV)

<400> SEQUENCE: 93

Glu Ile Lys Asp Thr Lys Glu Ala Leu
1               5

<210> SEQ ID NO 94
<211> LENGTH: 8
<212> TYPE: PRT
<213> ORGANISM: Human Immunodeficiency Virus (HIV)

<400> SEQUENCE: 94

Tyr Leu Lys Asp Gln Gln Leu Leu
1               5

<210> SEQ ID NO 95
<211> LENGTH: 11
<212> TYPE: PRT
<213> ORGANISM: Human Immunodeficiency Virus (HIV)

<400> SEQUENCE: 95

Ile Leu Gly Leu Asn Lys Ile Val Arg Met Tyr
1               5                   10

<210> SEQ ID NO 96
<211> LENGTH: 9
<212> TYPE: PRT
<213> ORGANISM: Human Immunodeficiency Virus (HIV)

<400> SEQUENCE: 96

Glu Arg Tyr Leu Lys Asp Gln Gln Leu
1               5

<210> SEQ ID NO 97
<211> LENGTH: 11
<212> TYPE: PRT
<213> ORGANISM: Human Immunodeficiency Virus (HIV)

<400> SEQUENCE: 97

Tyr His Thr Gln Gly Tyr Phe Pro Gln Trp Gln
1               5                   10

<210> SEQ ID NO 98
<211> LENGTH: 12
<212> TYPE: PRT
<213> ORGANISM: Human Immunodeficiency Virus (HIV)

<400> SEQUENCE: 98

Thr Gln Gly Tyr Phe Pro Gln Trp Gln Asn Tyr Thr
1               5                   10

<210> SEQ ID NO 99
<211> LENGTH: 9
<212> TYPE: PRT
<213> ORGANISM: Human Immunodeficiency Virus (HIV)

```
<400> SEQUENCE: 99

Gly Arg Ala Phe Val Thr Leu Gly Lys
 1               5

<210> SEQ ID NO 100
<211> LENGTH: 9
<212> TYPE: PRT
<213> ORGANISM: Human Immunodeficiency Virus (HIV)

<400> SEQUENCE: 100

Lys Arg Trp Ile Ile Leu Gly Leu Asn
 1               5

<210> SEQ ID NO 101
<211> LENGTH: 10
<212> TYPE: PRT
<213> ORGANISM: Human Immunodeficiency Virus (HIV)

<400> SEQUENCE: 101

Gln Val Pro Leu Arg Pro Met Thr Tyr Lys
 1               5                  10

<210> SEQ ID NO 102
<211> LENGTH: 8
<212> TYPE: PRT
<213> ORGANISM: Human Immunodeficiency Virus (HIV-1)

<400> SEQUENCE: 102

Gly Gly Lys Lys Lys Tyr Lys Leu
 1               5

<210> SEQ ID NO 103
<211> LENGTH: 9
<212> TYPE: PRT
<213> ORGANISM: Human Immunodeficiency Virus (HIV-1)

<400> SEQUENCE: 103

Arg Val Lys Glu Lys Tyr Gln His Leu
 1               5

<210> SEQ ID NO 104
<211> LENGTH: 9
<212> TYPE: PRT
<213> ORGANISM: Human Immunodeficiency Virus (HIV-1)

<400> SEQUENCE: 104

Asp Arg Phe Tyr Lys Thr Leu Arg Ala
 1               5

<210> SEQ ID NO 105
<211> LENGTH: 16
<212> TYPE: PRT
<213> ORGANISM: Human Immunodeficiency Virus (HIV-1)

<400> SEQUENCE: 105

Gly Val Arg Tyr Pro Leu Thr Phe Gly Trp Cys Tyr Lys Leu Val Pro
 1               5                  10                  15

<210> SEQ ID NO 106
<211> LENGTH: 10
<212> TYPE: PRT
<213> ORGANISM: Human Immunodeficiency Virus (HIV-1)

<400> SEQUENCE: 106

Lys Arg Trp Ile Ile Leu Gly Leu Asn Lys
```

```
<210> SEQ ID NO 107
<211> LENGTH: 9
<212> TYPE: PRT
<213> ORGANISM: Human Immunodeficiency Virus (HIV-1)

<400> SEQUENCE: 107

Ala Phe His His Val Ala Arg Glu Leu
1               5

<210> SEQ ID NO 108
<211> LENGTH: 9
<212> TYPE: PRT
<213> ORGANISM: Human Immunodeficiency Virus (HIV-1)

<400> SEQUENCE: 108

Ile Leu Lys Glu Pro Val His Gly Val
1               5

<210> SEQ ID NO 109
<211> LENGTH: 9
<212> TYPE: PRT
<213> ORGANISM: Human Immunodeficiency Virus (HIV-1)

<400> SEQUENCE: 109

Ala Phe His His Val Ala Arg Glu Leu
1               5

<210> SEQ ID NO 110
<211> LENGTH: 9
<212> TYPE: PRT
<213> ORGANISM: Human Immunodeficiency Virus (HIV-1)

<400> SEQUENCE: 110

Lys Leu Thr Pro Leu Cys Val Thr Leu
1               5

<210> SEQ ID NO 111
<211> LENGTH: 10
<212> TYPE: PRT
<213> ORGANISM: Human Immunodeficiency Virus (HIV-1)

<400> SEQUENCE: 111

Ser Leu Leu Asn Ala Thr Asp Ile Ala Val
1               5                   10

<210> SEQ ID NO 112
<211> LENGTH: 9
<212> TYPE: PRT
<213> ORGANISM: Human Immunodeficiency Virus (HIV-1)

<400> SEQUENCE: 112

Val Ile Tyr Gln Tyr Met Asp Asp Leu
1               5

<210> SEQ ID NO 113
<211> LENGTH: 9
<212> TYPE: PRT
<213> ORGANISM: Human Immunodeficiency Virus (HIV-1)

<400> SEQUENCE: 113

Ser Leu Tyr Asn Thr Val Ala Thr Leu
1               5
```

```
<210> SEQ ID NO 114
<211> LENGTH: 9
<212> TYPE: PRT
<213> ORGANISM: Human Immunodeficiency Virus (HIV-1)

<400> SEQUENCE: 114

Arg Gly Pro Gly Arg Ala Phe Val Thr
1               5

<210> SEQ ID NO 115
<211> LENGTH: 11
<212> TYPE: PRT
<213> ORGANISM: Human Immunodeficiency Virus (HIV-1)

<400> SEQUENCE: 115

Arg Leu Arg Asp Leu Leu Leu Ile Val Thr Arg
1               5                   10

<210> SEQ ID NO 116
<211> LENGTH: 10
<212> TYPE: PRT
<213> ORGANISM: Human Immunodeficiency Virus (HIV-1)

<400> SEQUENCE: 116

Gln Val Pro Leu Arg Pro Met Thr Tyr Lys
1               5                   10

<210> SEQ ID NO 117
<211> LENGTH: 10
<212> TYPE: PRT
<213> ORGANISM: Human Immunodeficiency Virus (HIV-1)

<400> SEQUENCE: 117

Thr Val Tyr Tyr Gly Val Pro Val Trp Lys
1               5                   10

<210> SEQ ID NO 118
<211> LENGTH: 9
<212> TYPE: PRT
<213> ORGANISM: Human Immunodeficiency Virus (HIV-1)

<400> SEQUENCE: 118

Arg Leu Arg Pro Gly Gly Lys Lys Lys
1               5

<210> SEQ ID NO 119
<211> LENGTH: 9
<212> TYPE: PRT
<213> ORGANISM: Human Immunodeficiency Virus (HIV-1)

<400> SEQUENCE: 119

Val Tyr Tyr Gly Val Pro Val Trp Lys
1               5

<210> SEQ ID NO 120
<211> LENGTH: 9
<212> TYPE: PRT
<213> ORGANISM: Human Immunodeficiency Virus (HIV-1)

<400> SEQUENCE: 120

Val Pro Leu Arg Pro Met Thr Tyr Lys
1               5

<210> SEQ ID NO 121
<211> LENGTH: 9
<212> TYPE: PRT
```

```
<213> ORGANISM: Human Immunodeficiency Virus (HIV-1)

<400> SEQUENCE: 121

Ala Ile Phe Gln Ser Ser Met Thr Lys
1               5

<210> SEQ ID NO 122
<211> LENGTH: 10
<212> TYPE: PRT
<213> ORGANISM: Human Immunodeficiency Virus (HIV-1)

<400> SEQUENCE: 122

Gln Val Pro Leu Arg Pro Met Thr Tyr Lys
1               5                   10

<210> SEQ ID NO 123
<211> LENGTH: 12
<212> TYPE: PRT
<213> ORGANISM: Human Immunodeficiency Virus (HIV-1)

<400> SEQUENCE: 123

Ala Ala Val Asp Leu Ser His Phe Leu Lys Glu Lys
1               5                   10

<210> SEQ ID NO 124
<211> LENGTH: 12
<212> TYPE: PRT
<213> ORGANISM: Human Immunodeficiency Virus (HIV-1)

<400> SEQUENCE: 124

Ala Cys Gln Gly Val Gly Gly Pro Gly His Lys
1               5                   10

<210> SEQ ID NO 125
<211> LENGTH: 10
<212> TYPE: PRT
<213> ORGANISM: Human Immunodeficiency Virus (HIV-1)

<400> SEQUENCE: 125

Glu Thr Ile Asn Glu Glu Ala Ala Glu Trp
1               5                   10

<210> SEQ ID NO 126
<211> LENGTH: 10
<212> TYPE: PRT
<213> ORGANISM: Human Immunodeficiency Virus (HIV-1)

<400> SEQUENCE: 126

Thr Pro Gly Pro Gly Val Arg Tyr Pro Leu
1               5                   10

<210> SEQ ID NO 127
<211> LENGTH: 9
<212> TYPE: PRT
<213> ORGANISM: Measles Virus

<400> SEQUENCE: 127

Asp Pro Val Ile Asp Arg Leu Tyr Leu
1               5

<210> SEQ ID NO 128
<211> LENGTH: 9
<212> TYPE: PRT
<213> ORGANISM: Measles Virus

<400> SEQUENCE: 128
```

```
Ser Pro Gly Arg Ser Phe Ser Tyr Phe
1               5

<210> SEQ ID NO 129
<211> LENGTH: 9
<212> TYPE: PRT
<213> ORGANISM: Pseudorabies Virus gp

<400> SEQUENCE: 129

Ile Ala Gly Ile Gly Ile Leu Ala Ile
1               5

<210> SEQ ID NO 130
<211> LENGTH: 9
<212> TYPE: PRT
<213> ORGANISM: Rabies virus

<400> SEQUENCE: 130

Val Glu Ala Glu Ile Ala His Gln Ile
1               5

<210> SEQ ID NO 131
<211> LENGTH: 9
<212> TYPE: PRT
<213> ORGANISM: Respiratory syncytial virus (RSV)

<400> SEQUENCE: 131

Ser Tyr Ile Gly Ser Ile Asn Asn Ile
1               5

<210> SEQ ID NO 132
<211> LENGTH: 12
<212> TYPE: PRT
<213> ORGANISM: Simian Immunodeficiency Virus (SIV)

<400> SEQUENCE: 132

Glu Gly Cys Thr Pro Tyr Asp Thr Asn Gln Met Leu
1               5                   10

<210> SEQ ID NO 133
<211> LENGTH: 9
<212> TYPE: PRT
<213> ORGANISM: Epstein-Barr Virus (EBV)

<400> SEQUENCE: 133

Lys Glu His Val Ile Gln Asn Ala Phe
1               5

<210> SEQ ID NO 134
<211> LENGTH: 10
<212> TYPE: PRT
<213> ORGANISM: Epstein-Barr Virus (EBV)

<400> SEQUENCE: 134

Glu Glu Asn Leu Leu Asp Phe Val Arg Phe
1               5                   10

<210> SEQ ID NO 135
<211> LENGTH: 10
<212> TYPE: PRT
<213> ORGANISM: Epstein-Barr Virus (EBV)

<400> SEQUENCE: 135

Asp Thr Pro Leu Ile Pro Leu Thr Ile Phe
1               5                   10
```

```
<210> SEQ ID NO 136
<211> LENGTH: 10
<212> TYPE: PRT
<213> ORGANISM: Epstein-Barr Virus (EBV)

<400> SEQUENCE: 136

Gln Asn Gly Ala Leu Ala Ile Asn Thr Phe
1               5                   10

<210> SEQ ID NO 137
<211> LENGTH: 9
<212> TYPE: PRT
<213> ORGANISM: Epstein-Barr Virus (EBV)

<400> SEQUENCE: 137

Arg Leu Arg Ala Glu Ala Gly Val Lys
1               5

<210> SEQ ID NO 138
<211> LENGTH: 10
<212> TYPE: PRT
<213> ORGANISM: Hepatitis B Virus

<400> SEQUENCE: 138

Gly Leu Ser Pro Thr Val Trp Leu Ser Val
1               5                   10

<210> SEQ ID NO 139
<211> LENGTH: 9
<212> TYPE: PRT
<213> ORGANISM: Hepatitis  B Virus

<400> SEQUENCE: 139

Trp Leu Ser Leu Leu Val Pro Phe Val
1               5

<210> SEQ ID NO 140
<211> LENGTH: 10
<212> TYPE: PRT
<213> ORGANISM: Hepatitis  B Virus

<400> SEQUENCE: 140

Phe Leu Pro Ser Asp Phe Phe Pro Ser Val
1               5                   10

<210> SEQ ID NO 141
<211> LENGTH: 10
<212> TYPE: PRT
<213> ORGANISM: Hepatitis  B Virus

<400> SEQUENCE: 141

Phe Leu Pro Ser Asp Phe Phe Pro Ser Val
1               5                   10

<210> SEQ ID NO 142
<211> LENGTH: 10
<212> TYPE: PRT
<213> ORGANISM: Hepatitis  B Virus

<400> SEQUENCE: 142

Phe Leu Pro Ser Asp Phe Phe Pro Ser Val
1               5                   10

<210> SEQ ID NO 143
```

<211> LENGTH: 10
<212> TYPE: PRT
<213> ORGANISM: Hepatitis B Virus

<400> SEQUENCE: 143

Phe Leu Pro Ser Asp Phe Phe Pro Ser Val
1               5                   10

<210> SEQ ID NO 144
<211> LENGTH: 9
<212> TYPE: PRT
<213> ORGANISM: Hepatitis B Virus

<400> SEQUENCE: 144

Phe Leu Leu Ser Leu Gly Ile His Leu
1               5

<210> SEQ ID NO 145
<211> LENGTH: 9
<212> TYPE: PRT
<213> ORGANISM: Hepatitis B Virus

<400> SEQUENCE: 145

Ser Leu Tyr Ala Asp Ser Pro Ser Val
1               5

<210> SEQ ID NO 146
<211> LENGTH: 9
<212> TYPE: PRT
<213> ORGANISM: Hepatitis B Virus

<400> SEQUENCE: 146

Gly Leu Ser Arg Tyr Val Ala Arg Leu
1               5

<210> SEQ ID NO 147
<211> LENGTH: 10
<212> TYPE: PRT
<213> ORGANISM: Hepatitis B Virus

<400> SEQUENCE: 147

Leu Leu Val Pro Phe Val Gln Trp Phe Val
1               5                   10

<210> SEQ ID NO 148
<211> LENGTH: 9
<212> TYPE: PRT
<213> ORGANISM: Hepatitis B Virus

<400> SEQUENCE: 148

Ala Leu Met Pro Leu Tyr Ala Cys Ile
1               5

<210> SEQ ID NO 149
<211> LENGTH: 10
<212> TYPE: PRT
<213> ORGANISM: Hepatitis B Virus

<400> SEQUENCE: 149

Leu Leu Pro Ile Phe Phe Cys Leu Trp Val
1               5                   10

<210> SEQ ID NO 150
<211> LENGTH: 9
<212> TYPE: PRT
<213> ORGANISM: Hepatitis B Virus

```
<400> SEQUENCE: 150

Tyr Met Asp Asp Val Val Leu Gly Ala
 1               5

<210> SEQ ID NO 151
<211> LENGTH: 9
<212> TYPE: PRT
<213> ORGANISM: Hepatitis  B Virus

<400> SEQUENCE: 151

Leu Leu Leu Cys Leu Ile Phe Leu Leu
 1               5

<210> SEQ ID NO 152
<211> LENGTH: 10
<212> TYPE: PRT
<213> ORGANISM: Hepatitis  B Virus

<400> SEQUENCE: 152

Leu Leu Asp Tyr Gln Gly Met Leu Pro Val
 1               5                   10

<210> SEQ ID NO 153
<211> LENGTH: 10
<212> TYPE: PRT
<213> ORGANISM: Hepatitis  B Virus

<400> SEQUENCE: 153

Ser Ile Val Ser Pro Phe Ile Pro Leu Leu
 1               5                   10

<210> SEQ ID NO 154
<211> LENGTH: 9
<212> TYPE: PRT
<213> ORGANISM: Hepatitis  B Virus

<400> SEQUENCE: 154

Phe Leu Leu Thr Arg Ile Leu Thr Ile
 1               5

<210> SEQ ID NO 155
<211> LENGTH: 9
<212> TYPE: PRT
<213> ORGANISM: Hepatitis  B Virus

<400> SEQUENCE: 155

Tyr Val Asn Val Asn Met Gly Leu Lys
 1               5

<210> SEQ ID NO 156
<211> LENGTH: 11
<212> TYPE: PRT
<213> ORGANISM: Hepatitis  B Virus

<400> SEQUENCE: 156

Ser Thr Leu Pro Glu Thr Thr Val Val Arg Arg
 1               5                   10

<210> SEQ ID NO 157
<211> LENGTH: 11
<212> TYPE: PRT
<213> ORGANISM: Hepatitis  B Virus

<400> SEQUENCE: 157
```

```
Ser Thr Leu Pro Glu Thr Thr Val Val Arg Arg
1               5                   10
```

<210> SEQ ID NO 158
<211> LENGTH: 10
<212> TYPE: PRT
<213> ORGANISM: Hepatitis B Virus

<400> SEQUENCE: 158

```
Phe Leu Pro Ser Asp Phe Phe Pro Ser Val
1               5                   10
```

<210> SEQ ID NO 159
<211> LENGTH: 12
<212> TYPE: PRT
<213> ORGANISM: Hepatitis B Virus

<400> SEQUENCE: 159

```
Ile Pro Gln Ser Leu Asp Ser Trp Trp Thr Ser Leu
1               5                   10
```

<210> SEQ ID NO 160
<211> LENGTH: 8
<212> TYPE: PRT
<213> ORGANISM: Hepatitis B Virus

<400> SEQUENCE: 160

```
Met Gly Leu Lys Phe Arg Gln Leu
1               5
```

<210> SEQ ID NO 161
<211> LENGTH: 9
<212> TYPE: PRT
<213> ORGANISM: Hepatitis B Virus
<220> FEATURE:
<221> NAME/KEY: VARIANT
<222> LOCATION: 4, 8
<223> OTHER INFORMATION: Xaa = Any Amino Acid

<400> SEQUENCE: 161

```
Ser Thr Asx Xaa Gln Ser Gly Xaa Gln
1               5
```

<210> SEQ ID NO 162
<211> LENGTH: 11
<212> TYPE: PRT
<213> ORGANISM: Human cytomegalovirus

<400> SEQUENCE: 162

```
Phe Ile Ala Gly Asn Ser Ala Tyr Glu Tyr Val
1               5                   10
```

<210> SEQ ID NO 163
<211> LENGTH: 12
<212> TYPE: PRT
<213> ORGANISM: Human cytomegalovirus

<400> SEQUENCE: 163

```
Ser Asp Glu Glu Phe Ala Ile Val Ala Tyr Thr Leu
1               5                   10
```

<210> SEQ ID NO 164
<211> LENGTH: 15
<212> TYPE: PRT
<213> ORGANISM: Human cytomegalovirus

<400> SEQUENCE: 164

```
Asp Asp Val Trp Thr Ser Gly Ser Asp Ser Asp Glu Glu Leu Val
1               5                   10                  15

<210> SEQ ID NO 165
<211> LENGTH: 9
<212> TYPE: PRT
<213> ORGANISM: Human cytomegalovirus

<400> SEQUENCE: 165

Ile Pro Ser Ile Asn Val His His Tyr
1               5

<210> SEQ ID NO 166
<211> LENGTH: 10
<212> TYPE: PRT
<213> ORGANISM: Human cytomegalovirus

<400> SEQUENCE: 166

Asn Leu Val Pro Met Val Ala Thr Val Gln
1               5                   10

<210> SEQ ID NO 167
<211> LENGTH: 15
<212> TYPE: PRT
<213> ORGANISM: Human cytomegalovirus

<400> SEQUENCE: 167

Arg Lys Thr Pro Arg Val Thr Gly Gly Gly Ala Met Ala Gly Ala
1               5                   10                  15

<210> SEQ ID NO 168
<211> LENGTH: 9
<212> TYPE: PRT
<213> ORGANISM: Hepatitis C Virus

<400> SEQUENCE: 168

Asp Leu Met Gly Tyr Ile Pro Leu Val
1               5

<210> SEQ ID NO 169
<211> LENGTH: 10
<212> TYPE: PRT
<213> ORGANISM: Hepatitis C Virus

<400> SEQUENCE: 169

Leu Leu Ala Leu Leu Ser Cys Leu Thr Val
1               5                   10

<210> SEQ ID NO 170
<211> LENGTH: 8
<212> TYPE: PRT
<213> ORGANISM: Hepatitis C Virus

<400> SEQUENCE: 170

Ile Leu His Thr Pro Gly Cys Val
1               5

<210> SEQ ID NO 171
<211> LENGTH: 10
<212> TYPE: PRT
<213> ORGANISM: Hepatitis C Virus

<400> SEQUENCE: 171

Gln Leu Arg Arg His Ile Asp Leu Leu Val
1               5                   10
```

<210> SEQ ID NO 172
<211> LENGTH: 9
<212> TYPE: PRT
<213> ORGANISM: Hepatitis C Virus

<400> SEQUENCE: 172

Asp Leu Cys Gly Ser Val Phe Leu Val
1               5

<210> SEQ ID NO 173
<211> LENGTH: 9
<212> TYPE: PRT
<213> ORGANISM: Hepatitis C Virus

<400> SEQUENCE: 173

Ser Met Val Gly Asn Trp Ala Lys Val
1               5

<210> SEQ ID NO 174
<211> LENGTH: 10
<212> TYPE: PRT
<213> ORGANISM: Hepatitis C Virus

<400> SEQUENCE: 174

His Leu Ile Ile Gln Asn Ile Val Asp Val
1               5                   10

<210> SEQ ID NO 175
<211> LENGTH: 9
<212> TYPE: PRT
<213> ORGANISM: Hepatitis C Virus

<400> SEQUENCE: 175

Phe Leu Leu Leu Ala Asp Ala Arg Val
1               5

<210> SEQ ID NO 176
<211> LENGTH: 13
<212> TYPE: PRT
<213> ORGANISM: Hepatitis C Virus

<400> SEQUENCE: 176

Gly Leu Arg Asp Leu Ala Val Ala Val Glu Pro Val Val
1               5                   10

<210> SEQ ID NO 177
<211> LENGTH: 11
<212> TYPE: PRT
<213> ORGANISM: Hepatitis C Virus

<400> SEQUENCE: 177

Ser Leu Leu Ala Pro Gly Ala Lys Gln Asn Val
1               5                   10

<210> SEQ ID NO 178
<211> LENGTH: 10
<212> TYPE: PRT
<213> ORGANISM: Hepatitis C Virus

<400> SEQUENCE: 178

Leu Leu Ala Pro Gly Ala Lys Gln Asn Val
1               5                   10

<210> SEQ ID NO 179

<211> LENGTH: 10
<212> TYPE: PRT
<213> ORGANISM: Hepatitis C Virus

<400> SEQUENCE: 179

Leu Leu Phe Asn Ile Leu Gly Gly Trp Val
1 5 10

<210> SEQ ID NO 180
<211> LENGTH: 9
<212> TYPE: PRT
<213> ORGANISM: Hepatitis C Virus

<400> SEQUENCE: 180

Tyr Leu Val Ala Tyr Gln Ala Thr Val
1 5

<210> SEQ ID NO 181
<211> LENGTH: 10
<212> TYPE: PRT
<213> ORGANISM: Hepatitis C Virus

<400> SEQUENCE: 181

Tyr Leu Leu Pro Arg Arg Gly Pro Arg Leu
1 5 10

<210> SEQ ID NO 182
<211> LENGTH: 10
<212> TYPE: PRT
<213> ORGANISM: Hepatitis C Virus

<400> SEQUENCE: 182

Leu Leu Ala Leu Leu Ser Cys Leu Thr Ile
1 5 10

<210> SEQ ID NO 183
<211> LENGTH: 9
<212> TYPE: PRT
<213> ORGANISM: Hepatitis C Virus

<400> SEQUENCE: 183

Ser Leu Met Ala Phe Thr Ala Ala Val
1 5

<210> SEQ ID NO 184
<211> LENGTH: 9
<212> TYPE: PRT
<213> ORGANISM: Hepatitis C Virus

<400> SEQUENCE: 184

Cys Ile Asn Gly Val Cys Trp Thr Val
1 5

<210> SEQ ID NO 185
<211> LENGTH: 9
<212> TYPE: PRT
<213> ORGANISM: Hepatitis C Virus

<400> SEQUENCE: 185

Leu Leu Cys Pro Ala Gly His Ala Val
1 5

<210> SEQ ID NO 186
<211> LENGTH: 9
<212> TYPE: PRT
<213> ORGANISM: Hepatitis C Virus

<400> SEQUENCE: 186

Ile Leu Asp Ser Phe Asp Pro Leu Val
1               5

<210> SEQ ID NO 187
<211> LENGTH: 9
<212> TYPE: PRT
<213> ORGANISM: Hepatitis C Virus

<400> SEQUENCE: 187

Ile Leu Ala Gly Tyr Gly Ala Gly Val
1               5

<210> SEQ ID NO 188
<211> LENGTH: 9
<212> TYPE: PRT
<213> ORGANISM: Hepatitis C Virus

<400> SEQUENCE: 188

Gly Leu Gln Asp Cys Thr Met Leu Val
1               5

<210> SEQ ID NO 189
<211> LENGTH: 10
<212> TYPE: PRT
<213> ORGANISM: Hepatitis C Virus

<400> SEQUENCE: 189

Thr Gly Ala Pro Val Thr Tyr Ser Thr Tyr
1               5                   10

<210> SEQ ID NO 190
<211> LENGTH: 9
<212> TYPE: PRT
<213> ORGANISM: Hepatitis C Virus

<400> SEQUENCE: 190

His Met Trp Asn Phe Ile Ser Gly Ile
1               5

<210> SEQ ID NO 191
<211> LENGTH: 9
<212> TYPE: PRT
<213> ORGANISM: Hepatitis C Virus

<400> SEQUENCE: 191

Arg Val Cys Glu Lys Met Ala Leu Tyr
1               5

<210> SEQ ID NO 192
<211> LENGTH: 8
<212> TYPE: PRT
<213> ORGANISM: Hepatitis C Virus

<400> SEQUENCE: 192

Thr Ile Asn Tyr Thr Ile Phe Lys
1               5

<210> SEQ ID NO 193
<211> LENGTH: 8
<212> TYPE: PRT
<213> ORGANISM: Hepatitis C Virus

<400> SEQUENCE: 193

```
Tyr Ile Ser Trp Cys Leu Trp Trp
1               5

<210> SEQ ID NO 194
<211> LENGTH: 9
<212> TYPE: PRT
<213> ORGANISM: Hepatitis C Virus

<400> SEQUENCE: 194

Gly Pro Arg Leu Gly Val Arg Ala Thr
1               5

<210> SEQ ID NO 195
<211> LENGTH: 9
<212> TYPE: PRT
<213> ORGANISM: Human Immunodeficiency Virus (HIV-1)

<400> SEQUENCE: 195

Ser Phe Asn Cys Gly Gly Glu Phe Phe
1               5

<210> SEQ ID NO 196
<211> LENGTH: 9
<212> TYPE: PRT
<213> ORGANISM: Human Immunodeficiency Virus (HIV-1)

<400> SEQUENCE: 196

Thr Glu Met Glu Lys Glu Gly Lys Ile
1               5

<210> SEQ ID NO 197
<211> LENGTH: 9
<212> TYPE: PRT
<213> ORGANISM: Human Immunodeficiency Virus (HIV-1)

<400> SEQUENCE: 197

Lys Ile Arg Leu Arg Pro Gly Gly Lys
1               5

<210> SEQ ID NO 198
<211> LENGTH: 10
<212> TYPE: PRT
<213> ORGANISM: Human Immunodeficiency Virus (HIV-1)

<400> SEQUENCE: 198

Arg Leu Arg Pro Gly Gly Lys Lys Lys Tyr
1               5                   10

<210> SEQ ID NO 199
<211> LENGTH: 9
<212> TYPE: PRT
<213> ORGANISM: Human Immunodeficiency Virus (HIV-1)

<400> SEQUENCE: 199

Ala Ile Phe Gln Ser Ser Met Thr Lys
1               5

<210> SEQ ID NO 200
<211> LENGTH: 9
<212> TYPE: PRT
<213> ORGANISM: Human Immunodeficiency Virus (HIV-1)

<400> SEQUENCE: 200

Thr Leu Tyr Cys Val His Gln Arg Ile
1               5
```

<210> SEQ ID NO 201
<211> LENGTH: 10
<212> TYPE: PRT
<213> ORGANISM: Human Immunodeficiency Virus (HIV-1)

<400> SEQUENCE: 201

Ile Tyr Gln Glu Pro Phe Lys Asn Leu Lys
1               5                   10

<210> SEQ ID NO 202
<211> LENGTH: 9
<212> TYPE: PRT
<213> ORGANISM: Human Immunodeficiency Virus (HIV-1)

<400> SEQUENCE: 202

Lys Tyr Lys Leu Lys His Ile Val Trp
1               5

<210> SEQ ID NO 203
<211> LENGTH: 10
<212> TYPE: PRT
<213> ORGANISM: Human Immunodeficiency Virus (HIV-1)

<400> SEQUENCE: 203

Leu Phe Cys Ala Ser Asp Ala Lys Ala Tyr
1               5                   10

<210> SEQ ID NO 204
<211> LENGTH: 11
<212> TYPE: PRT
<213> ORGANISM: Human Immunodeficiency Virus (HIV-1)

<400> SEQUENCE: 204

Gln Ala Ile Ser Pro Arg Thr Leu Asn Ala Trp
1               5                   10

<210> SEQ ID NO 205
<211> LENGTH: 9
<212> TYPE: PRT
<213> ORGANISM: Human Immunodeficiency Virus (HIV-1)

<400> SEQUENCE: 205

Glu Val Ile Pro Met Phe Ser Ala Leu
1               5

<210> SEQ ID NO 206
<211> LENGTH: 11
<212> TYPE: PRT
<213> ORGANISM: Human Immunodeficiency Virus (HIV-1)

<400> SEQUENCE: 206

Glu Thr Phe Tyr Val Asp Gly Ala Ala Asn Arg
1               5                   10

<210> SEQ ID NO 207
<211> LENGTH: 11
<212> TYPE: PRT
<213> ORGANISM: Human Immunodeficiency Virus (HIV-1)

<400> SEQUENCE: 207

Arg Leu Arg Asp Leu Leu Leu Ile Val Thr Arg
1               5                   10

<210> SEQ ID NO 208
<211> LENGTH: 10

```
<212> TYPE: PRT
<213> ORGANISM: Human Immunodeficiency Virus (HIV-1)

<400> SEQUENCE: 208

Pro Ile Gln Lys Glu Thr Trp Glu Thr Trp
1               5                   10

<210> SEQ ID NO 209
<211> LENGTH: 9
<212> TYPE: PRT
<213> ORGANISM: Human Immunodeficiency Virus (HIV-1)

<400> SEQUENCE: 209

Arg Ile Lys Gln Ile Ile Asn Met Trp
1               5

<210> SEQ ID NO 210
<211> LENGTH: 9
<212> TYPE: PRT
<213> ORGANISM: Human Immunodeficiency Virus (HIV-1)

<400> SEQUENCE: 210

Ile Thr Leu Trp Gln Arg Pro Leu Val
1               5

<210> SEQ ID NO 211
<211> LENGTH: 9
<212> TYPE: PRT
<213> ORGANISM: Human Immunodeficiency Virus (HIV-1)

<400> SEQUENCE: 211

Asp Thr Val Leu Glu Glu Met Asn Leu
1               5

<210> SEQ ID NO 212
<211> LENGTH: 9
<212> TYPE: PRT
<213> ORGANISM: Human Immunodeficiency Virus (HIV-1)

<400> SEQUENCE: 212

Ile Thr Leu Trp Gln Arg Pro Leu Val
1               5

<210> SEQ ID NO 213
<211> LENGTH: 9
<212> TYPE: PRT
<213> ORGANISM: Human Immunodeficiency Virus (HIV-1)

<400> SEQUENCE: 213

Ser Pro Arg Thr Leu Asn Ala Trp Val
1               5

<210> SEQ ID NO 214
<211> LENGTH: 9
<212> TYPE: PRT
<213> ORGANISM: Human Immunodeficiency Virus (HIV-1)

<400> SEQUENCE: 214

Ala Thr Pro Gln Asp Leu Asn Thr Met
1               5

<210> SEQ ID NO 215
<211> LENGTH: 10
<212> TYPE: PRT
<213> ORGANISM: Human Immunodeficiency Virus (HIV-1)
```

<400> SEQUENCE: 215

Arg Pro Asn Asn Thr Arg Lys Ser Ile
1               5                   10

<210> SEQ ID NO 216
<211> LENGTH: 9
<212> TYPE: PRT
<213> ORGANISM: Human Immunodeficiency Virus (HIV-1)

<400> SEQUENCE: 216

Ile Pro Arg Arg Ile Arg Gln Gly Leu
1               5

<210> SEQ ID NO 217
<211> LENGTH: 9
<212> TYPE: PRT
<213> ORGANISM: Human Immunodeficiency Virus (HIV-1)

<400> SEQUENCE: 217

Glu Leu Arg Ser Leu Tyr Asn Thr Val
1               5

<210> SEQ ID NO 218
<211> LENGTH: 8
<212> TYPE: PRT
<213> ORGANISM: Human Immunodeficiency Virus (HIV-1)

<400> SEQUENCE: 218

Trp Pro Thr Val Arg Glu Arg Met
1               5

<210> SEQ ID NO 219
<211> LENGTH: 8
<212> TYPE: PRT
<213> ORGANISM: Human Immunodeficiency Virus (HIV-1)

<400> SEQUENCE: 219

Phe Leu Lys Glu Lys Gly Gly Leu
1               5

<210> SEQ ID NO 220
<211> LENGTH: 9
<212> TYPE: PRT
<213> ORGANISM: Human Immunodeficiency Virus (HIV-1)

<400> SEQUENCE: 220

Asp Leu Asn Thr Met Leu Asn Thr Val
1               5

<210> SEQ ID NO 221
<211> LENGTH: 10
<212> TYPE: PRT
<213> ORGANISM: Human Immunodeficiency Virus (HIV-1)

<400> SEQUENCE: 221

Lys Ile Arg Leu Arg Pro Gly Gly Lys Lys
1               5                   10

<210> SEQ ID NO 222
<211> LENGTH: 9
<212> TYPE: PRT
<213> ORGANISM: Human Immunodeficiency Virus (HIV-1)

<400> SEQUENCE: 222

Ile Arg Leu Arg Pro Gly Gly Lys Lys

<210> SEQ ID NO 223
<211> LENGTH: 10
<212> TYPE: PRT
<213> ORGANISM: Human Immunodeficiency Virus (HIV-1)

<400> SEQUENCE: 223

Gly Arg Arg Gly Trp Glu Ala Leu Lys Tyr
1               5                   10

<210> SEQ ID NO 224
<211> LENGTH: 10
<212> TYPE: PRT
<213> ORGANISM: Human Immunodeficiency Virus (HIV-1)

<400> SEQUENCE: 224

Gln Val Pro Leu Arg Pro Met Thr Tyr Lys
1               5                   10

<210> SEQ ID NO 225
<211> LENGTH: 8
<212> TYPE: PRT
<213> ORGANISM: Human Immunodeficiency Virus (HIV-1)

<400> SEQUENCE: 225

Arg Tyr Leu Lys Asp Gln Gln Leu
1               5

<210> SEQ ID NO 226
<211> LENGTH: 10
<212> TYPE: PRT
<213> ORGANISM: Human Immunodeficiency Virus (HIV-1)

<400> SEQUENCE: 226

Arg Arg Gln Asp Ile Leu Asp Leu Trp Ile
1               5                   10

<210> SEQ ID NO 227
<211> LENGTH: 8
<212> TYPE: PRT
<213> ORGANISM: Human Immunodeficiency Virus (HIV-1)

<400> SEQUENCE: 227

Arg Tyr Pro Leu Thr Phe Gly Trp
1               5

<210> SEQ ID NO 228
<211> LENGTH: 9
<212> TYPE: PRT
<213> ORGANISM: Human Immunodeficiency Virus (HIV-1)

<400> SEQUENCE: 228

Trp Ala Ser Arg Glu Leu Glu Arg Phe
1               5

<210> SEQ ID NO 229
<211> LENGTH: 9
<212> TYPE: PRT
<213> ORGANISM: Human Immunodeficiency Virus (HIV-1)

<400> SEQUENCE: 229

Thr Val Leu Asp Val Gly Asp Ala Tyr
1               5

```
<210> SEQ ID NO 230
<211> LENGTH: 11
<212> TYPE: PRT
<213> ORGANISM: Human Immunodeficiency Virus (HIV-1)

<400> SEQUENCE: 230

Val Pro Val Trp Lys Glu Ala Thr Thr Thr Leu
 1               5                  10

<210> SEQ ID NO 231
<211> LENGTH: 9
<212> TYPE: PRT
<213> ORGANISM: Human Immunodeficiency Virus (HIV-1)

<400> SEQUENCE: 231

Asn Ser Ser Lys Val Ser Gln Asn Tyr
 1               5

<210> SEQ ID NO 232
<211> LENGTH: 9
<212> TYPE: PRT
<213> ORGANISM: Human Immunodeficiency Virus (HIV-1)

<400> SEQUENCE: 232

Pro Pro Ile Pro Val Gly Asp Ile Tyr
 1               5

<210> SEQ ID NO 233
<211> LENGTH: 9
<212> TYPE: PRT
<213> ORGANISM: Human Immunodeficiency Virus (HIV-1)

<400> SEQUENCE: 233

His Pro Asp Ile Val Ile Tyr Gln Tyr
 1               5

<210> SEQ ID NO 234
<211> LENGTH: 9
<212> TYPE: PRT
<213> ORGANISM: Human Immunodeficiency Virus (HIV-1)

<400> SEQUENCE: 234

Thr Ala Val Pro Trp Asn Ala Ser Trp
 1               5

<210> SEQ ID NO 235
<211> LENGTH: 9
<212> TYPE: PRT
<213> ORGANISM: Human Immunodeficiency Virus (HIV-1)

<400> SEQUENCE: 235

Asn Pro Val Pro Val Gly Asn Leu Tyr
 1               5

<210> SEQ ID NO 236
<211> LENGTH: 9
<212> TYPE: PRT
<213> ORGANISM: Human Immunodeficiency Virus (HIV-1)

<400> SEQUENCE: 236

Tyr Phe Pro Asp Trp Gln Asn Tyr Thr
 1               5

<210> SEQ ID NO 237
<211> LENGTH: 9
<212> TYPE: PRT
```

<213> ORGANISM: Human Immunodeficiency Virus (HIV-1)

<400> SEQUENCE: 237

Gly His Gln Ala Ala Met Gln Met Leu
1               5

<210> SEQ ID NO 238
<211> LENGTH: 10
<212> TYPE: PRT
<213> ORGANISM: Human Immunodeficiency Virus (HIV-1)

<400> SEQUENCE: 238

Arg Leu Arg Pro Gly Gly Lys Lys Lys Tyr
1               5                   10

<210> SEQ ID NO 239
<211> LENGTH: 9
<212> TYPE: PRT
<213> ORGANISM: Human Immunodeficiency Virus (HIV-1)

<400> SEQUENCE: 239

Tyr Pro Gly Ile Lys Val Arg Gln Leu
1               5

<210> SEQ ID NO 240
<211> LENGTH: 10
<212> TYPE: PRT
<213> ORGANISM: Human Immunodeficiency Virus (HIV-1)

<400> SEQUENCE: 240

Gly Ala Glu Thr Phe Tyr Val Asp Gly Ala
1               5                   10

<210> SEQ ID NO 241
<211> LENGTH: 9
<212> TYPE: PRT
<213> ORGANISM: Human Immunodeficiency Virus (HIV-1)

<400> SEQUENCE: 241

Asn Ala Asn Pro Asp Cys Lys Thr Ile
1               5

<210> SEQ ID NO 242
<211> LENGTH: 8
<212> TYPE: PRT
<213> ORGANISM: Human Immunodeficiency Virus (HIV-1)

<400> SEQUENCE: 242

Arg Met Tyr Ser Pro Thr Ser Ile
1               5

<210> SEQ ID NO 243
<211> LENGTH: 10
<212> TYPE: PRT
<213> ORGANISM: Human Immunodeficiency Virus (HIV-1)

<400> SEQUENCE: 243

Val Pro Val Trp Lys Glu Ala Thr Thr Thr
1               5                   10

<210> SEQ ID NO 244
<211> LENGTH: 9
<212> TYPE: PRT
<213> ORGANISM: Human Immunodeficiency Virus (HIV-1)

<400> SEQUENCE: 244

```
Ile Ser Pro Arg Thr Leu Asn Ala Trp
1               5
```

<210> SEQ ID NO 245
<211> LENGTH: 10
<212> TYPE: PRT
<213> ORGANISM: Human Immunodeficiency Virus (HIV-1)

<400> SEQUENCE: 245

```
Thr Ser Thr Leu Gln Glu Gln Ile Gly Trp
1               5                   10
```

<210> SEQ ID NO 246
<211> LENGTH: 11
<212> TYPE: PRT
<213> ORGANISM: Human Immunodeficiency Virus (HIV-1)

<400> SEQUENCE: 246

```
Lys Ala Phe Ser Pro Glu Val Ile Pro Met Phe
1               5                   10
```

<210> SEQ ID NO 247
<211> LENGTH: 9
<212> TYPE: PRT
<213> ORGANISM: Human Immunodeficiency Virus (HIV-1)

<400> SEQUENCE: 247

```
Gln Ala Ser Gln Glu Val Lys Asn Trp
1               5
```

<210> SEQ ID NO 248
<211> LENGTH: 9
<212> TYPE: PRT
<213> ORGANISM: Human Immunodeficiency Virus (HIV-1)

<400> SEQUENCE: 248

```
Gln Ala Ser Gln Asp Val Lys Asn Trp
1               5
```

<210> SEQ ID NO 249
<211> LENGTH: 10
<212> TYPE: PRT
<213> ORGANISM: Human Immunodeficiency Virus (HIV-1)

<400> SEQUENCE: 249

```
His Thr Gln Gly Tyr Phe Pro Asp Trp Gln
1               5                   10
```

<210> SEQ ID NO 250
<211> LENGTH: 9
<212> TYPE: PRT
<213> ORGANISM: Human Immunodeficiency Virus (HIV-1)

<400> SEQUENCE: 250

```
Tyr Phe Pro Asp Trp Gln Asn Tyr Thr
1               5
```

<210> SEQ ID NO 251
<211> LENGTH: 10
<212> TYPE: PRT
<213> ORGANISM: Human Immunodeficiency Virus (HIV-1)

<400> SEQUENCE: 251

```
Thr Ser Thr Leu Gln Glu Gln Ile Gly Trp
1               5                   10
```

<210> SEQ ID NO 252
<211> LENGTH: 10
<212> TYPE: PRT
<213> ORGANISM: Human Immunodeficiency Virus (HIV-1)

<400> SEQUENCE: 252

Arg Leu Arg Pro Gly Gly Lys Lys Lys Tyr
1               5                   10

<210> SEQ ID NO 253
<211> LENGTH: 9
<212> TYPE: PRT
<213> ORGANISM: Human Immunodeficiency Virus (HIV-1)

<400> SEQUENCE: 253

Leu Gly Leu Asn Lys Val Arg Met Tyr
1               5

<210> SEQ ID NO 254
<211> LENGTH: 12
<212> TYPE: PRT
<213> ORGANISM: Human Immunodeficiency Virus (HIV-1)

<400> SEQUENCE: 254

Leu Val Gly Lys Leu Asn Trp Ala Ser Gln Ile Tyr
1               5                   10

<210> SEQ ID NO 255
<211> LENGTH: 10
<212> TYPE: PRT
<213> ORGANISM: Human Immunodeficiency Virus (HIV-1)

<400> SEQUENCE: 255

Ile Leu Lys Glu Pro Val His Gly Val Tyr
1               5                   10

<210> SEQ ID NO 256
<211> LENGTH: 11
<212> TYPE: PRT
<213> ORGANISM: Human Immunodeficiency Virus (HIV-1)

<400> SEQUENCE: 256

Thr Gln Gly Tyr Phe Pro Asp Trp Gln Asn Tyr
1               5                   10

<210> SEQ ID NO 257
<211> LENGTH: 8
<212> TYPE: PRT
<213> ORGANISM: Human Immunodeficiency Virus (HIV-1)

<400> SEQUENCE: 257

Ala Val Asp Leu Ser His Phe Leu
1               5

<210> SEQ ID NO 258
<211> LENGTH: 8
<212> TYPE: PRT
<213> ORGANISM: Human Immunodeficiency Virus (HIV-1)

<400> SEQUENCE: 258

Val Ile Pro Met Phe Ser Ala Leu
1               5

<210> SEQ ID NO 259

<211> LENGTH: 9
<212> TYPE: PRT
<213> ORGANISM: Human Immunodeficiency Virus (HIV-1)

<400> SEQUENCE: 259

Phe Asn Cys Gly Gly Glu Phe Phe Tyr
1               5

<210> SEQ ID NO 260
<211> LENGTH: 9
<212> TYPE: PRT
<213> ORGANISM: Human Immunodeficiency Virus (HIV-1)

<400> SEQUENCE: 260

Ser Phe Asn Cys Gly Gly Glu Phe Phe
1               5

<210> SEQ ID NO 261
<211> LENGTH: 10
<212> TYPE: PRT
<213> ORGANISM: Human Immunodeficiency Virus (HIV-1)

<400> SEQUENCE: 261

Pro Leu Thr Phe Gly Trp Cys Tyr Lys Leu
1               5                   10

<210> SEQ ID NO 262
<211> LENGTH: 10
<212> TYPE: PRT
<213> ORGANISM: Human Immunodeficiency Virus (HIV-1)

<400> SEQUENCE: 262

Val Leu Glu Trp Arg Phe Asp Ser Arg Leu
1               5                   10

<210> SEQ ID NO 263
<211> LENGTH: 10
<212> TYPE: PRT
<213> ORGANISM: Human Immunodeficiency Virus (HIV-1)

<400> SEQUENCE: 263

Phe Pro Val Thr Pro Gln Val Pro Leu Arg
1               5                   10

<210> SEQ ID NO 264
<211> LENGTH: 10
<212> TYPE: PRT
<213> ORGANISM: Human Immunodeficiency Virus (HIV-1)

<400> SEQUENCE: 264

Thr Pro Gly Pro Gly Val Arg Tyr Pro Leu
1               5                   10

<210> SEQ ID NO 265
<211> LENGTH: 9
<212> TYPE: PRT
<213> ORGANISM: Human Immunodeficiency Virus (HIV-1)

<400> SEQUENCE: 265

Gln Ala Ser Gln Glu Val Lys Asn Trp
1               5

<210> SEQ ID NO 266
<211> LENGTH: 10
<212> TYPE: PRT
<213> ORGANISM: Human Immunodeficiency Virus (HIV-1)

<400> SEQUENCE: 266

Val Pro Leu Asp Glu Asp Phe Arg Lys Tyr
1               5                   10

<210> SEQ ID NO 267
<211> LENGTH: 9
<212> TYPE: PRT
<213> ORGANISM: Human Immunodeficiency Virus (HIV-1)

<400> SEQUENCE: 267

Asn Pro Asp Ile Val Ile Tyr Gln Tyr
1               5

<210> SEQ ID NO 268
<211> LENGTH: 9
<212> TYPE: PRT
<213> ORGANISM: Human Immunodeficiency Virus (HIV-1)

<400> SEQUENCE: 268

Arg Ala Ile Glu Ala Gln Ala His Leu
1               5

<210> SEQ ID NO 269
<211> LENGTH: 8
<212> TYPE: PRT
<213> ORGANISM: Human Immunodeficiency Virus (HIV-1)

<400> SEQUENCE: 269

Thr Ala Phe Thr Ile Pro Ser Ile
1               5

<210> SEQ ID NO 270
<211> LENGTH: 10
<212> TYPE: PRT
<213> ORGANISM: Human Immunodeficiency Virus (HIV-1)

<400> SEQUENCE: 270

Val His Pro Val His Ala Gly Pro Ile Ala
1               5                   10

<210> SEQ ID NO 271
<211> LENGTH: 10
<212> TYPE: PRT
<213> ORGANISM: Human Immunodeficiency Virus (HIV-1)

<400> SEQUENCE: 271

Asn Cys Ser Phe Asn Ile Ser Thr Ser Ile
1               5                   10

<210> SEQ ID NO 272
<211> LENGTH: 9
<212> TYPE: PRT
<213> ORGANISM: Human Immunodeficiency Virus (HIV-1)

<400> SEQUENCE: 272

Cys Thr Asn Val Ser Thr Val Gln Cys
1               5

<210> SEQ ID NO 273
<211> LENGTH: 9
<212> TYPE: PRT
<213> ORGANISM: Human Immunodeficiency Virus (HIV-1)

<400> SEQUENCE: 273

-continued

Ile Gly Pro Gly Arg Ala Phe His Thr
1               5

<210> SEQ ID NO 274
<211> LENGTH: 9
<212> TYPE: PRT
<213> ORGANISM: Human Immunodeficiency Virus (HIV-1)

<400> SEQUENCE: 274

Asn Pro Asp Ile Val Ile Tyr Gln Tyr
1               5

<210> SEQ ID NO 275
<211> LENGTH: 10
<212> TYPE: PRT
<213> ORGANISM: Human Immunodeficiency Virus (HIV-1)

<400> SEQUENCE: 275

Glu Pro Ile Val Gly Ala Glu Thr Phe Tyr
1               5                   10

<210> SEQ ID NO 276
<211> LENGTH: 9
<212> TYPE: PRT
<213> ORGANISM: Human Immunodeficiency Virus (HIV-1)

<400> SEQUENCE: 276

Glu Pro Ile Val Gly Ala Glu Thr Phe
1               5

<210> SEQ ID NO 277
<211> LENGTH: 9
<212> TYPE: PRT
<213> ORGANISM: Human Immunodeficiency Virus (HIV-1)

<400> SEQUENCE: 277

Ser Pro Ala Ile Phe Gln Ser Ser Met
1               5

<210> SEQ ID NO 278
<211> LENGTH: 10
<212> TYPE: PRT
<213> ORGANISM: Human Immunodeficiency Virus (HIV-1)

<400> SEQUENCE: 278

Val Pro Leu Asp Lys Asp Phe Arg Lys Tyr
1               5                   10

<210> SEQ ID NO 279
<211> LENGTH: 9
<212> TYPE: PRT
<213> ORGANISM: Human Immunodeficiency Virus (HIV-1)

<400> SEQUENCE: 279

Ile Pro Leu Thr Glu Glu Ala Glu Leu
1               5

<210> SEQ ID NO 280
<211> LENGTH: 11
<212> TYPE: PRT
<213> ORGANISM: Human Immunodeficiency Virus (HIV-1)

<400> SEQUENCE: 280

Arg Pro Gln Val Pro Leu Arg Pro Met Thr Tyr
1               5                   10

```
<210> SEQ ID NO 281
<211> LENGTH: 9
<212> TYPE: PRT
<213> ORGANISM: Human Immunodeficiency Virus (HIV-1)

<400> SEQUENCE: 281

Phe Pro Val Arg Pro Gln Val Pro Leu
 1               5

<210> SEQ ID NO 282
<211> LENGTH: 9
<212> TYPE: PRT
<213> ORGANISM: Human Immunodeficiency Virus (HIV-1)

<400> SEQUENCE: 282

Asp Pro Asn Pro Gln Glu Val Val Leu
 1               5

<210> SEQ ID NO 283
<211> LENGTH: 9
<212> TYPE: PRT
<213> ORGANISM: Human Immunodeficiency Virus (HIV-1)

<400> SEQUENCE: 283

Arg Pro Ile Val Ser Thr Gln Leu Leu
 1               5

<210> SEQ ID NO 284
<211> LENGTH: 9
<212> TYPE: PRT
<213> ORGANISM: Human Immunodeficiency Virus (HIV-1)

<400> SEQUENCE: 284

Ile Pro Leu Thr Glu Glu Ala Glu Leu
 1               5

<210> SEQ ID NO 285
<211> LENGTH: 9
<212> TYPE: PRT
<213> ORGANISM: Human Immunodeficiency Virus (HIV-1)

<400> SEQUENCE: 285

Asp Pro Asn Pro Gln Glu Val Val Leu
 1               5

<210> SEQ ID NO 286
<211> LENGTH: 9
<212> TYPE: PRT
<213> ORGANISM: Human Immunodeficiency Virus (HIV-1)

<400> SEQUENCE: 286

Ala Met Gln Met Leu Lys Glu Thr Ile
 1               5

<210> SEQ ID NO 287
<211> LENGTH: 9
<212> TYPE: PRT
<213> ORGANISM: Human Immunodeficiency Virus (HIV-1)

<400> SEQUENCE: 287

Thr Pro Tyr Asp Arg Asn Gln Met Leu
 1               5

<210> SEQ ID NO 288
<211> LENGTH: 11
```

```
<212> TYPE: PRT
<213> ORGANISM: Human Immunodeficiency Virus (HIV-1)

<400> SEQUENCE: 288

Arg Arg Trp Ile Gln Leu Gly Leu Gln Lys Val
1               5                   10

<210> SEQ ID NO 289
<211> LENGTH: 15
<212> TYPE: PRT
<213> ORGANISM: Human Immunodeficiency Virus (HIV-1)

<400> SEQUENCE: 289

Gly Ile Trp Gly Cys Ser Gly Lys Leu Ile Cys Thr Thr Ala Val
1               5                   10                  15

<210> SEQ ID NO 290
<211> LENGTH: 15
<212> TYPE: PRT
<213> ORGANISM: Human Immunodeficiency Virus (HIV-1)

<400> SEQUENCE: 290

Ala Leu Ile Trp Glu Asp Leu Arg Ser Leu Cys Leu Phe Ser Tyr
1               5                   10                  15

<210> SEQ ID NO 291
<211> LENGTH: 9
<212> TYPE: PRT
<213> ORGANISM: Human Papilloma Virus (HPV)

<400> SEQUENCE: 291

Gly Leu His Cys Tyr Glu Gln Leu Val
1               5

<210> SEQ ID NO 292
<211> LENGTH: 9
<212> TYPE: PRT
<213> ORGANISM: Human Papilloma Virus (HPV)

<400> SEQUENCE: 292

Pro Leu Lys Gln His Phe Gln Ile Val
1               5

<210> SEQ ID NO 293
<211> LENGTH: 9
<212> TYPE: PRT
<213> ORGANISM: Human Papilloma Virus (HPV)

<400> SEQUENCE: 293

Arg Leu Val Thr Leu Lys Asp Ile Val
1               5

<210> SEQ ID NO 294
<211> LENGTH: 9
<212> TYPE: PRT
<213> ORGANISM: Human Papilloma Virus (HPV)

<400> SEQUENCE: 294

Thr Leu Gly Ile Val Cys Pro Ile Cys
1               5

<210> SEQ ID NO 295
<211> LENGTH: 9
<212> TYPE: PRT
<213> ORGANISM: Human Papilloma Virus (HPV)
```

-continued

```
<400> SEQUENCE: 295

Gly Thr Leu Gly Ile Val Cys Pro Ile
1               5

<210> SEQ ID NO 296
<211> LENGTH: 9
<212> TYPE: PRT
<213> ORGANISM: Human Papilloma Virus (HPV)

<400> SEQUENCE: 296

Met Leu Asp Leu Gln Pro Glu Thr Thr
1               5

<210> SEQ ID NO 297
<211> LENGTH: 10
<212> TYPE: PRT
<213> ORGANISM: Human Papilloma Virus (HPV)

<400> SEQUENCE: 297

Tyr Met Leu Asp Leu Gln Pro Glu Thr Thr
1               5                   10

<210> SEQ ID NO 298
<211> LENGTH: 8
<212> TYPE: PRT
<213> ORGANISM: Human Papilloma Virus (HPV)

<400> SEQUENCE: 298

Arg Pro Arg Lys Leu Pro Gln Leu
1               5

<210> SEQ ID NO 299
<211> LENGTH: 9
<212> TYPE: PRT
<213> ORGANISM: Human Papilloma Virus (HPV)

<400> SEQUENCE: 299

Arg Ala His Tyr Asn Ile Val Thr Phe
1               5

<210> SEQ ID NO 300
<211> LENGTH: 8
<212> TYPE: PRT
<213> ORGANISM: Herpes Simplex Virus (HSV)

<400> SEQUENCE: 300

Ser Ser Ile Glu Phe Ala Arg Leu
1               5

<210> SEQ ID NO 301
<211> LENGTH: 9
<212> TYPE: PRT
<213> ORGANISM: Herpes Simplex Virus (HSV-1)

<400> SEQUENCE: 301

Gly Ile Gly Ile Gly Val Leu Ala Ala
1               5

<210> SEQ ID NO 302
<211> LENGTH: 9
<212> TYPE: PRT
<213> ORGANISM: Herpes Simplex Virus (HSV-1)

<400> SEQUENCE: 302

Asp Tyr Ala Thr Leu Gly Val Gly Val
```

-continued

```
<210> SEQ ID NO 303
<211> LENGTH: 11
<212> TYPE: PRT
<213> ORGANISM: Herpes Simplex Virus (HSV-1)

<400> SEQUENCE: 303

Leu Tyr Arg Thr Phe Ala Gly Asn Pro Arg Ala
 1               5                  10

<210> SEQ ID NO 304
<211> LENGTH: 8
<212> TYPE: PRT
<213> ORGANISM: Herpes Simplex Virus (HSV-1)

<400> SEQUENCE: 304

Gln Thr Phe Asp Phe Gly Arg Leu
 1               5

<210> SEQ ID NO 305
<211> LENGTH: 9
<212> TYPE: PRT
<213> ORGANISM: Herpes Simplex Virus (HSV-2)

<400> SEQUENCE: 305

Gly Ala Gly Ile Gly Val Ala Val Leu
 1               5

<210> SEQ ID NO 306
<211> LENGTH: 9
<212> TYPE: PRT
<213> ORGANISM: Human T-cell Leukemia Virus (HTLV-1)

<400> SEQUENCE: 306

Leu Leu Phe Gly Tyr Pro Val Tyr Val
 1               5

<210> SEQ ID NO 307
<211> LENGTH: 9
<212> TYPE: PRT
<213> ORGANISM: Influenza Virus

<400> SEQUENCE: 307

Gly Ile Leu Gly Phe Val Phe Thr Leu
 1               5

<210> SEQ ID NO 308
<211> LENGTH: 10
<212> TYPE: PRT
<213> ORGANISM: Influenza Virus

<400> SEQUENCE: 308

Ile Leu Gly Phe Val Phe Thr Leu Thr Val
 1               5                  10

<210> SEQ ID NO 309
<211> LENGTH: 9
<212> TYPE: PRT
<213> ORGANISM: Influenza Virus

<400> SEQUENCE: 309

Ile Leu Arg Gly Ser Val Ala His Lys
 1               5
```

```
<210> SEQ ID NO 310
<211> LENGTH: 9
<212> TYPE: PRT
<213> ORGANISM: Influenza Virus

<400> SEQUENCE: 310

Lys Thr Gly Gly Pro Ile Tyr Lys Arg
1               5

<210> SEQ ID NO 311
<211> LENGTH: 9
<212> TYPE: PRT
<213> ORGANISM: Influenza Virus

<400> SEQUENCE: 311

Glu Leu Arg Ser Arg Tyr Trp Ala Ile
1               5

<210> SEQ ID NO 312
<211> LENGTH: 8
<212> TYPE: PRT
<213> ORGANISM: Influenza Virus

<400> SEQUENCE: 312

Leu Arg Ser Arg Tyr Trp Ala Ile
1               5

<210> SEQ ID NO 313
<211> LENGTH: 9
<212> TYPE: PRT
<213> ORGANISM: Influenza Virus

<400> SEQUENCE: 313

Glu Asp Leu Arg Val Leu Ser Phe Ile
1               5

<210> SEQ ID NO 314
<211> LENGTH: 9
<212> TYPE: PRT
<213> ORGANISM: Influenza Virus

<400> SEQUENCE: 314

Gly Glu Ile Ser Pro Leu Pro Ser Leu
1               5

<210> SEQ ID NO 315
<211> LENGTH: 9
<212> TYPE: PRT
<213> ORGANISM: Influenza Virus

<400> SEQUENCE: 315

Phe Glu Asp Leu Arg Val Leu Ser Phe
1               5

<210> SEQ ID NO 316
<211> LENGTH: 9
<212> TYPE: PRT
<213> ORGANISM: Influenza Virus

<400> SEQUENCE: 316

Gly Glu Ile Ser Pro Leu Pro Ser Leu
1               5

<210> SEQ ID NO 317
<211> LENGTH: 9
<212> TYPE: PRT
```

<213> ORGANISM: Influenza Virus

<400> SEQUENCE: 317

Phe Glu Asp Leu Arg Val Leu Ser Phe
1               5

<210> SEQ ID NO 318
<211> LENGTH: 9
<212> TYPE: PRT
<213> ORGANISM: Influenza Virus

<400> SEQUENCE: 318

Val Ser Asp Gly Gly Pro Lys Leu Tyr
1 5

<210> SEQ ID NO 319
<211> LENGTH: 9
<212> TYPE: PRT
<213> ORGANISM: Influenza Virus A

<400> SEQUENCE: 319

Cys Thr Glu Leu Lys Leu Ser Asp Tyr
1 5

<210> SEQ ID NO 320
<211> LENGTH: 9
<212> TYPE: PRT
<213> ORGANISM: Influenza Virus

<400> SEQUENCE: 320

Ala Ile Met Asp Lys Asn Ile Ile Leu
1 5

<210> SEQ ID NO 321
<211> LENGTH: 10
<212> TYPE: PRT
<213> ORGANISM: Influenza Virus A

<400> SEQUENCE: 321

Ile Met Asp Lys Asn Ile Ile Leu Lys Ala
1 5 10

<210> SEQ ID NO 322
<211> LENGTH: 9
<212> TYPE: PRT
<213> ORGANISM: Influenza Virus A

<400> SEQUENCE: 322

Ser Arg Tyr Trp Ala Ile Arg Thr Arg
1 5

<210> SEQ ID NO 323
<211> LENGTH: 9
<212> TYPE: PRT
<213> ORGANISM: Influenza Virus A

<400> SEQUENCE: 323

Thr Tyr Gln Arg Thr Arg Ala Leu Val
1 5

<210> SEQ ID NO 324
<211> LENGTH: 10
<212> TYPE: PRT
<213> ORGANISM: Influenza Virus A

<400> SEQUENCE: 324

```
Thr Tyr Val Ser Val Ser Thr Ser Thr Leu
1               5                   10

<210> SEQ ID NO 325
<211> LENGTH: 9
<212> TYPE: PRT
<213> ORGANISM: Influenza Virus A

<400> SEQUENCE: 325

Ile Tyr Ser Thr Val Ala Ser Ser Leu
1               5

<210> SEQ ID NO 326
<211> LENGTH: 8
<212> TYPE: PRT
<213> ORGANISM: Influenza Virus A

<400> SEQUENCE: 326

Phe Glu Ala Asn Gly Asn Leu Ile
1               5

<210> SEQ ID NO 327
<211> LENGTH: 9
<212> TYPE: PRT
<213> ORGANISM: Influenza Virus A

<400> SEQUENCE: 327

Ile Glu Gly Gly Trp Thr Gly Met Leu
1               5

<210> SEQ ID NO 328
<211> LENGTH: 8
<212> TYPE: PRT
<213> ORGANISM: Influenza Virus A

<400> SEQUENCE: 328

Ser Asp Tyr Glu Gly Arg Leu Ile
1               5

<210> SEQ ID NO 329
<211> LENGTH: 9
<212> TYPE: PRT
<213> ORGANISM: Influenza Virus A

<400> SEQUENCE: 329

Glu Glu Gly Ala Ile Val Gly Glu Ile
1               5

<210> SEQ ID NO 330
<211> LENGTH: 9
<212> TYPE: PRT
<213> ORGANISM: Influenza Virus A34

<400> SEQUENCE: 330

Ala Ser Asn Glu Asn Met Glu Thr Met
1               5

<210> SEQ ID NO 331
<211> LENGTH: 9
<212> TYPE: PRT
<213> ORGANISM: Influenza Virus A68

<400> SEQUENCE: 331

Ala Ser Asn Glu Asn Met Asp Ala Met
1               5
```

<210> SEQ ID NO 332
<211> LENGTH: 10
<212> TYPE: PRT
<213> ORGANISM: Influenza Virus B

<400> SEQUENCE: 332

Lys Leu Gly Glu Phe Tyr Asn Gln Met Met
1               5                   10

<210> SEQ ID NO 333
<211> LENGTH: 10
<212> TYPE: PRT
<213> ORGANISM: Influenza Virus B

<400> SEQUENCE: 333

Lys Ala Gly Glu Phe Tyr Asn Gln Met Met
1               5                   10

<210> SEQ ID NO 334
<211> LENGTH: 9
<212> TYPE: PRT
<213> ORGANISM: Influenza Virus JAP

<400> SEQUENCE: 334

Leu Tyr Gln Asn Val Gly Thr Tyr Val
1               5

<210> SEQ ID NO 335
<211> LENGTH: 10
<212> TYPE: PRT
<213> ORGANISM: Influenza Virus JAP

<400> SEQUENCE: 335

Thr Tyr Val Ser Val Gly Thr Ser Thr Leu
1               5                   10

<210> SEQ ID NO 336
<211> LENGTH: 9
<212> TYPE: PRT
<213> ORGANISM: Influenza Virus JAP

<400> SEQUENCE: 336

Val Tyr Gln Ile Leu Ala Thr Tyr Ala
1               5

<210> SEQ ID NO 337
<211> LENGTH: 9
<212> TYPE: PRT
<213> ORGANISM: Influenza Virus JAP

<400> SEQUENCE: 337

Ile Tyr Ala Thr Val Ala Gly Ser Leu
1               5

<210> SEQ ID NO 338
<211> LENGTH: 10
<212> TYPE: PRT
<213> ORGANISM: Influenza Virus JAP

<400> SEQUENCE: 338

Thr Tyr Val Ser Val Gly Thr Ser Thr Ile
1               5                   10

<210> SEQ ID NO 339

-continued

```
<211> LENGTH: 8
<212> TYPE: PRT
<213> ORGANISM: Influenza Virus JAP

<400> SEQUENCE: 339

Phe Glu Ser Thr Gly Asn Leu Ile
1               5

<210> SEQ ID NO 340
<211> LENGTH: 9
<212> TYPE: PRT
<213> ORGANISM: Mouse Hepatitis Virus (JMH strain)

<400> SEQUENCE: 340

Ala Pro Thr Ala Gly Ala Phe Phe Phe
1               5

<210> SEQ ID NO 341
<211> LENGTH: 9
<212> TYPE: PRT
<213> ORGANISM: Lymphocytic Choriomeningitis Virus (LCMV)

<400> SEQUENCE: 341

Arg Pro Gln Ala Ser Gly Val Tyr Met
1               5

<210> SEQ ID NO 342
<211> LENGTH: 9
<212> TYPE: PRT
<213> ORGANISM: Lymphocytic Choriomeningitis Virus (LCMV)

<400> SEQUENCE: 342

Phe Gln Pro Gln Asn Gly Gln Phe Ile
1               5

<210> SEQ ID NO 343
<211> LENGTH: 11
<212> TYPE: PRT
<213> ORGANISM: Lymphocytic Choriomeningitis Virus (LCMV)

<400> SEQUENCE: 343

Ser Gly Val Glu Asn Pro Gly Gly Tyr Cys Leu
1               5                   10

<210> SEQ ID NO 344
<211> LENGTH: 10
<212> TYPE: PRT
<213> ORGANISM: Lymphocytic Choriomeningitis Virus (LCMV)

<400> SEQUENCE: 344

Lys Ala Val Tyr Asn Phe Ala Thr Cys Gly
1               5                   10

<210> SEQ ID NO 345
<211> LENGTH: 9
<212> TYPE: PRT
<213> ORGANISM: Murine Cytomegalovirus (MCMV)

<400> SEQUENCE: 345

Tyr Pro His Phe Met Pro Thr Asn Leu
1               5

<210> SEQ ID NO 346
<211> LENGTH: 9
<212> TYPE: PRT
<213> ORGANISM: Mouse Hepatitis Virus (MHV)
```

-continued

```
<400> SEQUENCE: 346

Cys Leu Ser Trp Asn Gly Pro His Leu
 1               5

<210> SEQ ID NO 347
<211> LENGTH: 11
<212> TYPE: PRT
<213> ORGANISM: Measles Virus

<400> SEQUENCE: 347

Ser Arg Arg Tyr Pro Asp Ala Val Tyr Leu His
 1               5                  10

<210> SEQ ID NO 348
<211> LENGTH: 9
<212> TYPE: PRT
<213> ORGANISM: MV Virus

<400> SEQUENCE: 348

Arg Arg Tyr Pro Asp Ala Val Tyr Leu
 1               5

<210> SEQ ID NO 349
<211> LENGTH: 9
<212> TYPE: PRT
<213> ORGANISM: MV Virus

<400> SEQUENCE: 349

Tyr Pro Ala Leu Gly Leu His Glu Phe
 1               5

<210> SEQ ID NO 350
<211> LENGTH: 9
<212> TYPE: PRT
<213> ORGANISM: Epstein-Barr Virus

<400> SEQUENCE: 350

Ile Val Thr Asp Phe Ser Val Ile Lys
 1               5

<210> SEQ ID NO 351
<211> LENGTH: 9
<212> TYPE: PRT
<213> ORGANISM: Human Immunodeficiency Virus (HIV-1)

<400> SEQUENCE: 351

Val Pro Leu Arg Pro Met Thr Tyr Lys
 1               5

<210> SEQ ID NO 352
<211> LENGTH: 9
<212> TYPE: PRT
<213> ORGANISM: Human Immunodeficiency Virus (HIV-1)

<400> SEQUENCE: 352

Ala Ile Phe Gln Ser Ser Met Thr Lys
 1               5

<210> SEQ ID NO 353
<211> LENGTH: 10
<212> TYPE: PRT
<213> ORGANISM: Human Immunodeficiency Virus (HIV-1)

<400> SEQUENCE: 353
```

Gln Val Pro Leu Arg Pro Met Thr Tyr Lys
1               5                   10

<210> SEQ ID NO 354
<211> LENGTH: 12
<212> TYPE: PRT
<213> ORGANISM: Human Immunodeficiency Virus (HIV-1)

<400> SEQUENCE: 354

Ala Ala Val Asp Leu Ser His Phe Leu Lys Glu Lys
1               5                   10

<210> SEQ ID NO 355
<211> LENGTH: 12
<212> TYPE: PRT
<213> ORGANISM: Human Immunodeficiency Virus (HIV-1)

<400> SEQUENCE: 355

Ala Cys Gln Gly Val Gly Gly Pro Gly Gly His Lys
1               5                   10

<210> SEQ ID NO 356
<211> LENGTH: 9
<212> TYPE: PRT
<213> ORGANISM: Human Immunodeficiency Virus (HIV)

<400> SEQUENCE: 356

Arg Tyr Leu Lys Asp Gln Gln Leu Leu
1               5

<210> SEQ ID NO 357
<211> LENGTH: 8
<212> TYPE: PRT
<213> ORGANISM: Epstein-Barr Virus

<400> SEQUENCE: 357

Arg Tyr Ser Ile Phe Phe Asp Tyr
1               5

<210> SEQ ID NO 358
<211> LENGTH: 10
<212> TYPE: PRT
<213> ORGANISM: Human Immunodeficiency Virus (HIV-1)

<400> SEQUENCE: 358

Glu Thr Ile Asn Glu Glu Ala Ala Glu Trp
1               5                   10

<210> SEQ ID NO 359
<211> LENGTH: 11
<212> TYPE: PRT
<213> ORGANISM: Hepatitis B Virus

<400> SEQUENCE: 359

Ser Thr Leu Pro Glu Thr Thr Val Val Arg Arg
1               5                   10

<210> SEQ ID NO 360
<211> LENGTH: 9
<212> TYPE: PRT
<213> ORGANISM: Orf Virus

<400> SEQUENCE: 360

Met Ser Leu Gln Arg Gln Phe Leu Arg
1               5

```
<210> SEQ ID NO 361
<211> LENGTH: 9
<212> TYPE: PRT
<213> ORGANISM: Human Immunodeficiency Virus (HIV)

<400> SEQUENCE: 361

Ile Val Gly Leu Asn Lys Ile Val Arg
1               5

<210> SEQ ID NO 362
<211> LENGTH: 9
<212> TYPE: PRT
<213> ORGANISM: Human Papilloma Virus

<400> SEQUENCE: 362

Thr Ile His Asp Ile Ile Leu Glu Cys
1               5

<210> SEQ ID NO 363
<211> LENGTH: 9
<212> TYPE: PRT
<213> ORGANISM: Human Papilloma Virus

<400> SEQUENCE: 363

Leu Gly Ile Val Cys Pro Ile Cys Ser
1               5

<210> SEQ ID NO 364
<211> LENGTH: 10
<212> TYPE: PRT
<213> ORGANISM: Hepatitis B Virus

<400> SEQUENCE: 364

Phe Leu Pro Ser Asp Phe Phe Pro Ser Val
1               5                   10

<210> SEQ ID NO 365
<211> LENGTH: 9
<212> TYPE: PRT
<213> ORGANISM: Epstein-Barr Virus

<400> SEQUENCE: 365

Ser Val Arg Asp Arg Leu Ala Arg Leu
1               5

<210> SEQ ID NO 366
<211> LENGTH: 10
<212> TYPE: PRT
<213> ORGANISM: Hepatitis B Virus

<400> SEQUENCE: 366

Phe Leu Pro Ser Asp Phe Phe Pro Ser Val
1               5                   10

<210> SEQ ID NO 367
<211> LENGTH: 10
<212> TYPE: PRT
<213> ORGANISM: Hepatitis B Virus

<400> SEQUENCE: 367

Phe Leu Pro Ser Asp Phe Phe Pro Ser Val
1               5                   10

<210> SEQ ID NO 368
<211> LENGTH: 11
```

```
<212> TYPE: PRT
<213> ORGANISM: Human Immunodeficiency Virus (HIV-1)

<400> SEQUENCE: 368

Arg Leu Arg Asp Leu Leu Leu Ile Val Thr Arg
1               5                   10

<210> SEQ ID NO 369
<211> LENGTH: 10
<212> TYPE: PRT
<213> ORGANISM: Human Immunodeficiency Virus (HIV-1)

<400> SEQUENCE: 369

Gln Val Pro Leu Arg Pro Met Thr Tyr Lys
1               5                   10

<210> SEQ ID NO 370
<211> LENGTH: 10
<212> TYPE: PRT
<213> ORGANISM: Human Immunodeficiency Virus (HIV-1)

<400> SEQUENCE: 370

Thr Val Tyr Tyr Gly Val Pro Val Trp Lys
1               5                   10

<210> SEQ ID NO 371
<211> LENGTH: 9
<212> TYPE: PRT
<213> ORGANISM: Human Immunodeficiency Virus (HIV-1)

<400> SEQUENCE: 371

Arg Leu Arg Pro Gly Gly Lys Lys Lys
1               5

<210> SEQ ID NO 372
<211> LENGTH: 9
<212> TYPE: PRT
<213> ORGANISM: Influenza Virus

<400> SEQUENCE: 372

Ile Leu Arg Gly Ser Val Ala His Lys
1               5

<210> SEQ ID NO 373
<211> LENGTH: 9
<212> TYPE: PRT
<213> ORGANISM: Epstein-Barr Virus

<400> SEQUENCE: 373

Arg Leu Arg Ala Glu Ala Gly Val Lys
1               5

<210> SEQ ID NO 374
<211> LENGTH: 11
<212> TYPE: PRT
<213> ORGANISM: Human Immunodeficiency Virus (HIV-1)

<400> SEQUENCE: 374

Arg Leu Arg Asp Leu Leu Leu Ile Val Thr Arg
1               5                   10

<210> SEQ ID NO 375
<211> LENGTH: 9
<212> TYPE: PRT
<213> ORGANISM: Human Immunodeficiency Virus (HIV-1)
```

```
<400> SEQUENCE: 375

Val Tyr Tyr Gly Val Pro Val Trp Lys
1               5

<210> SEQ ID NO 376
<211> LENGTH: 9
<212> TYPE: PRT
<213> ORGANISM: Hepatitis C Virus

<400> SEQUENCE: 376

Arg Val Cys Glu Lys Met Ala Leu Tyr
1               5

<210> SEQ ID NO 377
<211> LENGTH: 9
<212> TYPE: PRT
<213> ORGANISM: Influenza A Virus

<400> SEQUENCE: 377

Val Ser Asp Gly Gly Pro Asn Leu Tyr
1               5

<210> SEQ ID NO 378
<211> LENGTH: 9
<212> TYPE: PRT
<213> ORGANISM: Influenza A Virus

<400> SEQUENCE: 378

Cys Thr Glu Leu Lys Leu Ser Asp Tyr
1               5

<210> SEQ ID NO 379
<211> LENGTH: 9
<212> TYPE: PRT
<213> ORGANISM: Hepatitis B Virus
<220> FEATURE:
<221> NAME/KEY: VARIANT
<222> LOCATION: 4, 8
<223> OTHER INFORMATION: Xaa = Any Amino Acid

<400> SEQUENCE: 379

Ser Thr Asx Xaa Gln Ser Gly Xaa Gln
1               5

<210> SEQ ID NO 380
<211> LENGTH: 9
<212> TYPE: PRT
<213> ORGANISM: Human Immunodeficiency Virus (HIV-1)

<400> SEQUENCE: 380

Ile Leu Lys Glu Pro Val His Gly Val
1               5

<210> SEQ ID NO 381
<211> LENGTH: 10
<212> TYPE: PRT
<213> ORGANISM: Influenza Virus

<400> SEQUENCE: 381

Leu Leu Gly Phe Val Phe Thr Leu Thr Val
1               5                   10

<210> SEQ ID NO 382
<211> LENGTH: 10
<212> TYPE: PRT
<213> ORGANISM: Human T-Cell Lymphotropic Virus (HTLV-1)
```

<400> SEQUENCE: 382

Leu Leu Phe Gly Tyr Pro Val Tyr Val Val
1               5                   10

<210> SEQ ID NO 383
<211> LENGTH: 10
<212> TYPE: PRT
<213> ORGANISM: Hepatitis B Virus

<400> SEQUENCE: 383

Gly Leu Ser Pro Thr Val Trp Leu Ser Val
1               5                   10

<210> SEQ ID NO 384
<211> LENGTH: 9
<212> TYPE: PRT
<213> ORGANISM: Hepatitis B Virus

<400> SEQUENCE: 384

Trp Leu Ser Leu Leu Val Pro Phe Val
1               5

<210> SEQ ID NO 385
<211> LENGTH: 10
<212> TYPE: PRT
<213> ORGANISM: Hepatitis B Virus

<400> SEQUENCE: 385

Phe Leu Pro Ser Asp Phe Phe Pro Ser Val
1               5                   10

<210> SEQ ID NO 386
<211> LENGTH: 8
<212> TYPE: PRT
<213> ORGANISM: Epstein-Barr Virus

<400> SEQUENCE: 386

Cys Leu Gly Leu Leu Thr Met Val
1               5

<210> SEQ ID NO 387
<211> LENGTH: 11
<212> TYPE: PRT
<213> ORGANISM: Human Cytomegalovirus (HCMV)

<400> SEQUENCE: 387

Phe Leu Ala Gly Asn Ser Ala Tyr Glu Tyr Val
1               5                   10

<210> SEQ ID NO 388
<211> LENGTH: 10
<212> TYPE: PRT
<213> ORGANISM: Influenza Virus

<400> SEQUENCE: 388

Lys Leu Gly Glu Phe Tyr Asn Gln Met Met
1               5                   10

<210> SEQ ID NO 389
<211> LENGTH: 10
<212> TYPE: PRT
<213> ORGANISM: Hepatitis C Virus (HCV-1)

<400> SEQUENCE: 389

Lys Leu Val Ala Leu Gly Ile Asn Ala Val
1               5                   10

<210> SEQ ID NO 390
<211> LENGTH: 9
<212> TYPE: PRT
<213> ORGANISM: Hepatitis C Virus (HCV)

<400> SEQUENCE: 390

Asp Leu Met Gly Tyr Ile Pro Leu Val
1               5

<210> SEQ ID NO 391
<211> LENGTH: 9
<212> TYPE: PRT
<213> ORGANISM: Human Papilloma Virus (HPV)

<400> SEQUENCE: 391

Arg Leu Val Thr Leu Lys Asp Ile Val
1               5

<210> SEQ ID NO 392
<211> LENGTH: 10
<212> TYPE: PRT
<213> ORGANISM: Human Immunodeficiency Virus

<400> SEQUENCE: 392

Ala Phe His Ile Ile Val Ala Arg Glu Leu
1               5                   10

<210> SEQ ID NO 393
<211> LENGTH: 10
<212> TYPE: PRT
<213> ORGANISM: Influenza Virus

<400> SEQUENCE: 393

Lys Ala Gly Glu Phe Tyr Asn Gln Met Met
1               5                   10

<210> SEQ ID NO 394
<211> LENGTH: 9
<212> TYPE: PRT
<213> ORGANISM: Epstein-Barr Virus

<400> SEQUENCE: 394

Asn Ile Ala Glu Gly Leu Arg Ala Leu
1               5

<210> SEQ ID NO 395
<211> LENGTH: 9
<212> TYPE: PRT
<213> ORGANISM: Epstein-Barr Virus

<400> SEQUENCE: 395

Asn Leu Arg Arg Gly Thr Ala Leu Ala
1               5

<210> SEQ ID NO 396
<211> LENGTH: 9
<212> TYPE: PRT
<213> ORGANISM: Epstein-Barr Virus

<400> SEQUENCE: 396

Ala Leu Ala Ile Pro Gln Cys Arg Leu
1               5

```
<210> SEQ ID NO 397
<211> LENGTH: 9
<212> TYPE: PRT
<213> ORGANISM: Epstein-Barr Virus

<400> SEQUENCE: 397

Val Leu Lys Asp Ala Ile Lys Asp Leu
1               5

<210> SEQ ID NO 398
<211> LENGTH: 9
<212> TYPE: PRT
<213> ORGANISM: Epstein-Barr Virus

<400> SEQUENCE: 398

Phe Met Val Phe Leu Gln Thr His Ile
1               5

<210> SEQ ID NO 399
<211> LENGTH: 9
<212> TYPE: PRT
<213> ORGANISM: Epstein-Barr Virus

<400> SEQUENCE: 399

His Leu Ile Val Asp Thr Asp Ser Leu
1               5

<210> SEQ ID NO 400
<211> LENGTH: 9
<212> TYPE: PRT
<213> ORGANISM: Epstein-Barr Virus

<400> SEQUENCE: 400

Ser Leu Gly Asn Pro Ser Leu Ser Val
1               5

<210> SEQ ID NO 401
<211> LENGTH: 9
<212> TYPE: PRT
<213> ORGANISM: Epstein-Barr Virus

<400> SEQUENCE: 401

Pro Leu Ala Ser Ala Met Arg Met Leu
1               5

<210> SEQ ID NO 402
<211> LENGTH: 9
<212> TYPE: PRT
<213> ORGANISM: Epstein-Barr Virus

<400> SEQUENCE: 402

Arg Met Leu Trp Met Ala Asn Tyr Ile
1               5

<210> SEQ ID NO 403
<211> LENGTH: 9
<212> TYPE: PRT
<213> ORGANISM: Epstein-Barr Virus

<400> SEQUENCE: 403

Met Leu Trp Met Ala Asn Tyr Ile Val
1               5

<210> SEQ ID NO 404
<211> LENGTH: 9
```

```
<212> TYPE: PRT
<213> ORGANISM: Epstein-Barr Virus

<400> SEQUENCE: 404

Ile Leu Pro Gln Gly Pro Gln Thr Ala
1               5

<210> SEQ ID NO 405
<211> LENGTH: 10
<212> TYPE: PRT
<213> ORGANISM: Epstein-Barr Virus

<400> SEQUENCE: 405

Pro Leu Arg Pro Thr Ala Pro Thr Thr Ile
1               5                   10

<210> SEQ ID NO 406
<211> LENGTH: 9
<212> TYPE: PRT
<213> ORGANISM: Epstein-Barr Virus

<400> SEQUENCE: 406

Pro Leu Pro Pro Ala Thr Leu Thr Val
1               5

<210> SEQ ID NO 407
<211> LENGTH: 9
<212> TYPE: PRT
<213> ORGANISM: Epstein-Barr Virus

<400> SEQUENCE: 407

Arg Met His Leu Pro Val Leu His Val
1               5

<210> SEQ ID NO 408
<211> LENGTH: 9
<212> TYPE: PRT
<213> ORGANISM: Epstein-Barr Virus

<400> SEQUENCE: 408

Pro Met Pro Leu Pro Pro Ser Gln Leu
1               5

<210> SEQ ID NO 409
<211> LENGTH: 9
<212> TYPE: PRT
<213> ORGANISM: Epstein-Barr Virus

<400> SEQUENCE: 409

Gln Leu Pro Pro Pro Ala Ala Pro Ala
1               5

<210> SEQ ID NO 410
<211> LENGTH: 9
<212> TYPE: PRT
<213> ORGANISM: Epstein-Barr Virus

<400> SEQUENCE: 410

Ser Met Pro Glu Leu Ser Pro Val Leu
1               5

<210> SEQ ID NO 411
<211> LENGTH: 9
<212> TYPE: PRT
<213> ORGANISM: Epstein-Barr Virus
```

```
<400> SEQUENCE: 411

Asp Leu Asp Glu Ser Trp Asp Tyr Leu
1               5

<210> SEQ ID NO 412
<211> LENGTH: 10
<212> TYPE: PRT
<213> ORGANISM: Epstein-Barr Virus

<400> SEQUENCE: 412

Pro Leu Pro Cys Val Leu Trp Pro Val Val
1               5                   10

<210> SEQ ID NO 413
<211> LENGTH: 9
<212> TYPE: PRT
<213> ORGANISM: Epstein-Barr Virus

<400> SEQUENCE: 413

Ser Leu Glu Glu Cys Asp Ser Glu Leu
1               5

<210> SEQ ID NO 414
<211> LENGTH: 9
<212> TYPE: PRT
<213> ORGANISM: Epstein-Barr Virus

<400> SEQUENCE: 414

Glu Ile Lys Arg Tyr Lys Asn Arg Val
1               5

<210> SEQ ID NO 415
<211> LENGTH: 10
<212> TYPE: PRT
<213> ORGANISM: Epstein-Barr Virus

<400> SEQUENCE: 415

Gln Leu Leu Gln Phe Ile Tyr Arg Glu Val
1               5                   10

<210> SEQ ID NO 416
<211> LENGTH: 9
<212> TYPE: PRT
<213> ORGANISM: Epstein-Barr Virus

<400> SEQUENCE: 416

Leu Leu Gln His Tyr Arg Glu Val Ala
1               5

<210> SEQ ID NO 417
<211> LENGTH: 9
<212> TYPE: PRT
<213> ORGANISM: Epstein-Barr Virus

<400> SEQUENCE: 417

Leu Leu Lys Gln Met Cys Pro Ser Leu
1               5

<210> SEQ ID NO 418
<211> LENGTH: 9
<212> TYPE: PRT
<213> ORGANISM: Epstein-Barr Virus

<400> SEQUENCE: 418

Ser Ile Ile Pro Arg Thr Pro Asp Val
```

1 5

<210> SEQ ID NO 419
<211> LENGTH: 9
<212> TYPE: PRT
<213> ORGANISM: Influenza A Virus

<400> SEQUENCE: 419

Ala Ile Met Asp Lys Asn Ile Ile Leu
1 5

<210> SEQ ID NO 420
<211> LENGTH: 10
<212> TYPE: PRT
<213> ORGANISM: Influenza A Virus

<400> SEQUENCE: 420

Ile Met Asp Lys Asn Ile Ile Leu Lys Ala
1 5 10

<210> SEQ ID NO 421
<211> LENGTH: 10
<212> TYPE: PRT
<213> ORGANISM: Hepatitis C Virus

<400> SEQUENCE: 421

Leu Leu Ala Leu Leu Ser Cys Leu Thr Val
1 5 10

<210> SEQ ID NO 422
<211> LENGTH: 8
<212> TYPE: PRT
<213> ORGANISM: Hepatitis C Virus

<400> SEQUENCE: 422

Ile Leu His Thr Pro Gly Cys Val
1 5

<210> SEQ ID NO 423
<211> LENGTH: 10
<212> TYPE: PRT
<213> ORGANISM: Hepatitis C Virus

<400> SEQUENCE: 423

Gln Leu Arg Arg His Ile Asp Leu Leu Val
1 5 10

<210> SEQ ID NO 424
<211> LENGTH: 9
<212> TYPE: PRT
<213> ORGANISM: Hepatitis C Virus

<400> SEQUENCE: 424

Asp Leu Cys Gly Ser Val Phe Leu Val
1 5

<210> SEQ ID NO 425
<211> LENGTH: 9
<212> TYPE: PRT
<213> ORGANISM: Hepatitis C Virus

<400> SEQUENCE: 425

Ser Met Val Gly Asn Trp Ala Lys Val
1 5

```
<210> SEQ ID NO 426
<211> LENGTH: 9
<212> TYPE: PRT
<213> ORGANISM: Hepatitis C Virus

<400> SEQUENCE: 426

His Leu His Gln Asn Ile Val Asp Val
1               5

<210> SEQ ID NO 427
<211> LENGTH: 9
<212> TYPE: PRT
<213> ORGANISM: Hepatitis C Virus

<400> SEQUENCE: 427

Phe Leu Leu Leu Ala Asp Ala Arg Val
1               5

<210> SEQ ID NO 428
<211> LENGTH: 13
<212> TYPE: PRT
<213> ORGANISM: Hepatitis C Virus

<400> SEQUENCE: 428

Gly Leu Arg Asp Leu Ala Val Ala Val Glu Pro Val Val
1               5                   10

<210> SEQ ID NO 429
<211> LENGTH: 11
<212> TYPE: PRT
<213> ORGANISM: Hepatitis C Virus

<400> SEQUENCE: 429

Ser Leu Leu Ala Pro Gly Ala Lys Gln Asn Val
1               5                   10

<210> SEQ ID NO 430
<211> LENGTH: 10
<212> TYPE: PRT
<213> ORGANISM: Hepatitis C Virus

<400> SEQUENCE: 430

Leu Leu Ala Pro Gly Ala Lys Gln Asn Val
1               5                   10

<210> SEQ ID NO 431
<211> LENGTH: 9
<212> TYPE: PRT
<213> ORGANISM: Hepatitis B Virus

<400> SEQUENCE: 431

Phe Leu Leu Ser Leu Gly Ile His Leu
1               5

<210> SEQ ID NO 432
<211> LENGTH: 9
<212> TYPE: PRT
<213> ORGANISM: Hepatitis B Virus

<400> SEQUENCE: 432

Ser Leu Tyr Ala Asp Ser Pro Ser Val
1               5

<210> SEQ ID NO 433
<211> LENGTH: 9
<212> TYPE: PRT
```

-continued

<213> ORGANISM: Hepatitis B Virus

<400> SEQUENCE: 433

Gly Leu Ser Arg Tyr Val Ala Arg Leu
1               5

<210> SEQ ID NO 434
<211> LENGTH: 9
<212> TYPE: PRT
<213> ORGANISM: Human Immunodeficiency Virus (HIV-1)

<400> SEQUENCE: 434

Lys Leu Thr Pro Leu Cys Val Thr Leu
1               5

<210> SEQ ID NO 435
<211> LENGTH: 10
<212> TYPE: PRT
<213> ORGANISM: Human Immunodeficiency Virus (HIV-1)

<400> SEQUENCE: 435

Ser Leu Leu Asn Ala Thr Asp Ile Ala Val
1               5                   10

<210> SEQ ID NO 436
<211> LENGTH: 10
<212> TYPE: PRT
<213> ORGANISM: Hepatitis C Virus (HCV)

<400> SEQUENCE: 436

Leu Leu Phe Asn Ile Leu Gly Gly Trp Val
1               5                   10

<210> SEQ ID NO 437
<211> LENGTH: 10
<212> TYPE: PRT
<213> ORGANISM: Hepatitis B Virus (HBV)

<400> SEQUENCE: 437

Leu Leu Val Pro Phe Val Gln Trp Phe Trp
1               5                   10

<210> SEQ ID NO 438
<211> LENGTH: 9
<212> TYPE: PRT
<213> ORGANISM: Hepatitis B Virus (HBV)

<400> SEQUENCE: 438

Ala Leu Met Pro Leu Tyr Ala Cys Ile
1               5

<210> SEQ ID NO 439
<211> LENGTH: 9
<212> TYPE: PRT
<213> ORGANISM: Hepatitis C Virus (HCV)

<400> SEQUENCE: 439

Tyr Leu Val Ala Tyr Gln Ala Thr Val
1               5

<210> SEQ ID NO 440
<211> LENGTH: 10
<212> TYPE: PRT
<213> ORGANISM: Hepatitis C Virus (HCV)

<400> SEQUENCE: 440

Tyr Leu Leu Pro Arg Arg Gly Pro Arg Leu
1               5                   10

<210> SEQ ID NO 441
<211> LENGTH: 10
<212> TYPE: PRT
<213> ORGANISM: Hepatitis B Virus (HBV)

<400> SEQUENCE: 441

Leu Leu Pro Ile Phe Phe Cys Leu Trp Val
1               5                   10

<210> SEQ ID NO 442
<211> LENGTH: 9
<212> TYPE: PRT
<213> ORGANISM: Hepatitis B Virus (HBV)

<400> SEQUENCE: 442

Tyr Met Asp Asp Val Val Leu Gly Ala
1               5

<210> SEQ ID NO 443
<211> LENGTH: 9
<212> TYPE: PRT
<213> ORGANISM: Human Papilloma Virus

<400> SEQUENCE: 443

Gly Thr Leu Gly Ile Val Cys Pro Ile
1               5

<210> SEQ ID NO 444
<211> LENGTH: 10
<212> TYPE: PRT
<213> ORGANISM: Hepatitis C Virus (HCV)

<400> SEQUENCE: 444

Leu Leu Ala Leu Leu Ser Cys Leu Thr Ile
1               5                   10

<210> SEQ ID NO 445
<211> LENGTH: 9
<212> TYPE: PRT
<213> ORGANISM: Human Papilloma Virus

<400> SEQUENCE: 445

Met Leu Asp Leu Gln Pro Glu Thr Thr
1               5

<210> SEQ ID NO 446
<211> LENGTH: 9
<212> TYPE: PRT
<213> ORGANISM: Hepatitis C Virus (HCV)

<400> SEQUENCE: 446

Ser Leu Met Ala Phe Thr Ala Ala Val
1               5

<210> SEQ ID NO 447
<211> LENGTH: 9
<212> TYPE: PRT
<213> ORGANISM: Hepatitis C Virus (HCV)

<400> SEQUENCE: 447

Cys Ile Asn Gly Val Cys Trp Thr Val
1               5

```
<210> SEQ ID NO 448
<211> LENGTH: 9
<212> TYPE: PRT
<213> ORGANISM: Hepatitis C Virus (HCV)

<400> SEQUENCE: 448

Leu Leu Cys Pro Ala Gly His Ala Val
1               5

<210> SEQ ID NO 449
<211> LENGTH: 9
<212> TYPE: PRT
<213> ORGANISM: Hepatitis C Virus (HCV)

<400> SEQUENCE: 449

Ile Leu Asp Ser Phe Asp Pro Leu Val
1               5

<210> SEQ ID NO 450
<211> LENGTH: 9
<212> TYPE: PRT
<213> ORGANISM: Hepatitis B Virus (HBV)

<400> SEQUENCE: 450

Leu Leu Leu Cys Leu Ile Phe Leu Leu
1               5

<210> SEQ ID NO 451
<211> LENGTH: 10
<212> TYPE: PRT
<213> ORGANISM: Hepatitis B Virus (HBV)

<400> SEQUENCE: 451

Leu Ile Asp Tyr Gln Gly Met Leu Pro Val
1               5                   10

<210> SEQ ID NO 452
<211> LENGTH: 10
<212> TYPE: PRT
<213> ORGANISM: Hepatitis B Virus (HBV)

<400> SEQUENCE: 452

Ser Ile Val Ser Pro Phe Ile Pro Leu Leu
1               5                   10

<210> SEQ ID NO 453
<211> LENGTH: 9
<212> TYPE: PRT
<213> ORGANISM: Hepatitis B Virus (HBV)

<400> SEQUENCE: 453

Phe Leu Leu Thr Arg Ile Leu Thr Ile
1               5

<210> SEQ ID NO 454
<211> LENGTH: 9
<212> TYPE: PRT
<213> ORGANISM: Hepatitis C Virus (HCV)

<400> SEQUENCE: 454

Ile Leu Ala Gly Tyr Gly Ala Gly Val
1               5

<210> SEQ ID NO 455
```

```
<211> LENGTH: 9
<212> TYPE: PRT
<213> ORGANISM: Hepatitis C Virus (HCV)

<400> SEQUENCE: 455

Gly Leu Gln Asp Cys Thr Met Leu Val
1               5

<210> SEQ ID NO 456
<211> LENGTH: 10
<212> TYPE: PRT
<213> ORGANISM: Hepatitis C Virus (HCV)

<400> SEQUENCE: 456

Thr Gly Ala Pro Val Thr Tyr Ser Thr Tyr
1               5                   10

<210> SEQ ID NO 457
<211> LENGTH: 10
<212> TYPE: PRT
<213> ORGANISM: Human Immunodeficiency Virus

<400> SEQUENCE: 457

Val Ile Tyr Gln Tyr Met Asp Asp Leu Val
1               5                   10

<210> SEQ ID NO 458
<211> LENGTH: 9
<212> TYPE: PRT
<213> ORGANISM: Herpes Simplex Virus

<400> SEQUENCE: 458

Gly Ile Gly Ile Gly Val Leu Ala Ala
1               5

<210> SEQ ID NO 459
<211> LENGTH: 9
<212> TYPE: PRT
<213> ORGANISM: Herpes Simplex Virus

<400> SEQUENCE: 459

Gly Ala Gly Ile Gly Val Ala Val Leu
1               5

<210> SEQ ID NO 460
<211> LENGTH: 9
<212> TYPE: PRT
<213> ORGANISM: Pseudorabies Virus

<400> SEQUENCE: 460

Ile Ala Gly Ile Gly Ile Leu Ala Ile
1               5

<210> SEQ ID NO 461
<211> LENGTH: 9
<212> TYPE: PRT
<213> ORGANISM: Human Immunodeficiency Virus (HIV-1)

<400> SEQUENCE: 461

Ser Leu Tyr Asn Thr Val Ala Thr Leu
1               5

<210> SEQ ID NO 462
<211> LENGTH: 10
<212> TYPE: PRT
<213> ORGANISM: Human Immunodeficiency Virus (HIV-1)
```

<400> SEQUENCE: 462

Arg Gly Pro Gly Arg Ala Phe Val Thr Ile
1               5                   10

<210> SEQ ID NO 463
<211> LENGTH: 9
<212> TYPE: PRT
<213> ORGANISM: Hepatitis C Virus (HCV)

<400> SEQUENCE: 463

His Met Trp Asn Phe Ile Ser Gly Ile
1               5

<210> SEQ ID NO 464
<211> LENGTH: 10
<212> TYPE: PRT
<213> ORGANISM: Human Cytomegalovirus (HCMV)

<400> SEQUENCE: 464

Asn Leu Val Pro Met Val Ala Thr Val Gln
1               5                   10

<210> SEQ ID NO 465
<211> LENGTH: 9
<212> TYPE: PRT
<213> ORGANISM: Human Papilloma Virus

<400> SEQUENCE: 465

Gly Leu His Cys Tyr Glu Gln Leu Val
1               5

<210> SEQ ID NO 466
<211> LENGTH: 9
<212> TYPE: PRT
<213> ORGANISM: Human Papilloma Virus

<400> SEQUENCE: 466

Pro Leu Lys Gln His Phe Gln Ile Val
1               5

<210> SEQ ID NO 467
<211> LENGTH: 10
<212> TYPE: PRT
<213> ORGANISM: Epstein-Barr Virus

<400> SEQUENCE: 467

Leu Leu Asp Phe Val Arg Phe Met Gly Val
1               5                   10

<210> SEQ ID NO 468
<211> LENGTH: 9
<212> TYPE: PRT
<213> ORGANISM: Influenza Virus (Alaska Strain)

<400> SEQUENCE: 468

Ala Ile Met Glu Lys Asn Ile Met Leu
1               5

<210> SEQ ID NO 469
<211> LENGTH: 10
<212> TYPE: PRT
<213> ORGANISM: Human Papilloma Virus

<400> SEQUENCE: 469

```
Tyr Met Leu Asp Leu Gln Pro Glu Thr Thr
 1               5                  10

<210> SEQ ID NO 470
<211> LENGTH: 9
<212> TYPE: PRT
<213> ORGANISM: Human Papilloma Virus

<400> SEQUENCE: 470

Leu Leu Met Gly Thr Leu Gly Ile Val
 1               5

<210> SEQ ID NO 471
<211> LENGTH: 8
<212> TYPE: PRT
<213> ORGANISM: Human Papilloma Virus

<400> SEQUENCE: 471

Thr Leu Gly Ile Val Cys Pro Ile
 1               5

<210> SEQ ID NO 472
<211> LENGTH: 9
<212> TYPE: PRT
<213> ORGANISM: Human Immunodeficiency Virus (HIV-1)

<400> SEQUENCE: 472

Thr Leu Thr Ser Cys Asn Thr Ser Val
 1               5

<210> SEQ ID NO 473
<211> LENGTH: 9
<212> TYPE: PRT
<213> ORGANISM: Human Papilloma Virus

<400> SEQUENCE: 473

Lys Leu Pro Gln Leu Cys Thr Glu Leu
 1               5
```